United States Patent
Hwang et al.

(10) Patent No.: US 9,960,359 B2
(45) Date of Patent: May 1, 2018

(54) ARYLAMINE-BASED COMPOUND AND ORGANIC LIGHT EMITTING DIODE COMPRISING THE SAME

(71) Applicant: SAMSUNG DISPLAY CO., LTD., Yongin, Gyeonggi-Do (KR)

(72) Inventors: Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin (KR)

(*) Notice: Subject to any disclaimer, the term of this patent is extended or adjusted under 35 U.S.C. 154(b) by 592 days.

(21) Appl. No.: 14/061,733

(22) Filed: Oct. 23, 2013

(65) Prior Publication Data
US 2014/0361259 A1   Dec. 11, 2014

(30) Foreign Application Priority Data
Jun. 3, 2013   (KR) ................ 10-2013-0063693

(51) Int. Cl.
  *H01L 51/50*   (2006.01)
  *H01L 51/00*   (2006.01)
  (Continued)

(52) U.S. Cl.
  CPC .......... *H01L 51/006* (2013.01); *C07D 209/08* (2013.01); *C07D 209/56* (2013.01);
  (Continued)

(58) Field of Classification Search
  None
  See application file for complete search history.

(56) References Cited

U.S. PATENT DOCUMENTS

| 4,521,605 A | 6/1985 | Okazaki et al. |
| 5,635,308 A | 6/1997 | Inoue et al. |
| (Continued) | | |

FOREIGN PATENT DOCUMENTS

| JP | 8-12600 A | 1/1996 |
| JP | 2000-3782 A | 1/2000 |
| (Continued) | | |

*Primary Examiner* — Gregory D Clark
(74) *Attorney, Agent, or Firm* — Lewis Roca Rothgerber Christie LLP

(57) ABSTRACT

An arylamine-based compound is represented by Formula 1 below. The arylamine-based compound is included in an organic light emitting diode.

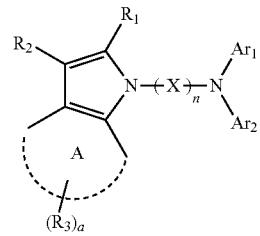

Formula 1

14 Claims, 1 Drawing Sheet

(51) Int. Cl.
  *C07D 401/10* (2006.01)
  *C07D 401/12* (2006.01)
  *C07D 405/04* (2006.01)
  *C07D 409/04* (2006.01)
  *C07D 409/12* (2006.01)
  *C07D 409/14* (2006.01)
  *C07D 471/04* (2006.01)
  *C07D 471/14* (2006.01)
  *C07D 487/04* (2006.01)
  *C07D 491/048* (2006.01)
  *C07D 495/04* (2006.01)
  *C07D 209/08* (2006.01)
  *C07D 209/56* (2006.01)
  *C07D 209/60* (2006.01)
  *C07D 209/94* (2006.01)
  *C07F 7/08* (2006.01)

(52) U.S. Cl.
  CPC ......... *C07D 209/60* (2013.01); *C07D 209/94* (2013.01); *C07D 401/10* (2013.01); *C07D 401/12* (2013.01); *C07D 405/04* (2013.01); *C07D 409/04* (2013.01); *C07D 409/12* (2013.01); *C07D 409/14* (2013.01); *C07D 471/04* (2013.01); *C07D 471/14* (2013.01); *C07D 487/04* (2013.01); *C07D 491/048* (2013.01); *C07D 495/04* (2013.01); *C07F 7/0812* (2013.01); *H01L 51/0059* (2013.01); *H01L 51/0061* (2013.01); *H01L 51/0072* (2013.01); *H01L 51/0094* (2013.01); *H01L 51/0052* (2013.01); *H01L 51/0058* (2013.01); *H01L 51/0074* (2013.01); *H01L 51/5064* (2013.01)

(56) References Cited

U.S. PATENT DOCUMENTS

| | | |
|---|---|---|
| 5,972,247 A | 10/1999 | Shi et al. |
| 6,451,461 B2 | 9/2002 | Lee et al. |
| 6,465,115 B2 | 10/2002 | Shi et al. |
| 6,596,415 B2 | 7/2003 | Shi et al. |
| 6,660,410 B2 | 12/2003 | Hosokawa |
| 6,670,054 B1 | 12/2003 | Hu et al. |
| 6,979,414 B2 | 12/2005 | Hosokawa |
| 2007/0018569 A1* | 1/2007 | Kawamura ........... C07C 211/61 313/504 |
| 2008/0014464 A1* | 1/2008 | Kawamura ........... C09K 11/06 428/690 |
| 2010/0033088 A1* | 2/2010 | Hwang ............... C07D 209/08 313/504 |
| 2011/0049484 A1 | 3/2011 | Kim et al. |
| 2011/0049490 A1* | 3/2011 | Kim ..................... C07D 209/60 257/40 |
| 2011/0297919 A1 | 12/2011 | Kwak et al. |
| 2012/0292606 A1 | 11/2012 | Kato |

FOREIGN PATENT DOCUMENTS

| | | | |
|---|---|---|---|
| JP | 2010-135689 | * 6/2010 | ............. H01L 51/50 |
| KR | 10-0346984 B1 | 7/2002 | |
| KR | 10-2011-0023088 A | 3/2011 | |
| KR | 10-2011-0132806 A | 12/2011 | |
| KR | 10-2012-0083241 A | 7/2012 | |
| KR | 10-2012-0101620 A | 9/2012 | |
| KR | 10-2012-0104172 A | 9/2012 | |

* cited by examiner

ARYLAMINE-BASED COMPOUND AND ORGANIC LIGHT EMITTING DIODE COMPRISING THE SAME

CROSS-REFERENCE TO RELATED APPLICATION

This application claims priority to and the benefit of Korean Patent Application No. 10-2013-0063693, filed on 3 Jun. 2013, in the Korean Intellectual Property Office, the disclosure of which is incorporated herein in its entirety by reference.

BACKGROUND

1. Field

The following disclosure relates to an arylamine-based compound and an organic light emitting diode including the arylamine-based compound.

2. Description of the Related Art

Organic light-emitting devices (OLEDs) are self-emitting devices that have advantages such as wide viewing angles, excellent contrast, quick response time, and excellent brightness, good driving voltage, or desired response speed characteristics, and can provide multicolored images.

A typical OLED has a structure including a substrate, and an anode, a hole transporting layer (HTL), an emission layer (EML), an electron transporting layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. Carriers such as the holes and electrons recombine in the EML to generate excitons. When the excitons drop from an excited state to a ground state, light is emitted.

SUMMARY

Aspects of the present invention are directed toward a high definition organic light emitting diode.

According to an embodiment of the present invention, an arylamine-based compound is represented by Formula 1 below:

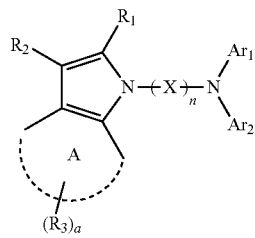

Formula 1

In Formula 1, ring A is selected from a $C_6$-$C_{20}$ aromatic ring or a $C_2$-$C_{20}$ heteroaromatic ring;

each X is independently selected from: a substituted or unsubstituted $C_6$-$C_{30}$ arylene group and a substituted or unsubstituted $C_2$-$C_{30}$ heteroarylene group, and the two or more of the Xs may be connected to each other to form a substituted or unsubstituted saturated ring or a substituted or unsubstituted unsaturated ring;

n is an integer of 1 to 5;

each of $Ar_1$ and $Ar_2$ is independently selected from a substituted or unsubstituted $C_6$-$C_{30}$ aryl group or a substituted or unsubstituted $C_2$-$C_{30}$ heteroaryl group;

each of $R_1$, $R_2$ and each of $R_3$ is independently selected from: a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or a substituted or unsubstituted $C_2$-$C_{30}$ heteroaryl group;

a is an integer of 0 to 4 but, when a is an integer of 2 or more, two or more $R_3$s may be the same or different.

According to another embodiment of the present invention, an organic light emitting diode includes: a first electrode; a second electrode facing the first electrode; and an organic layer between the first electrode and the second electrode, wherein the organic layer includes an emission layer and at least one of the arylamine-based compounds.

BRIEF DESCRIPTION OF THE DRAWINGS

The above and other features and enhancements of the present invention will become more apparent by describing in more detail example embodiments thereof with reference to the attached drawings in which.

DETAILED DESCRIPTION

Figure 1:
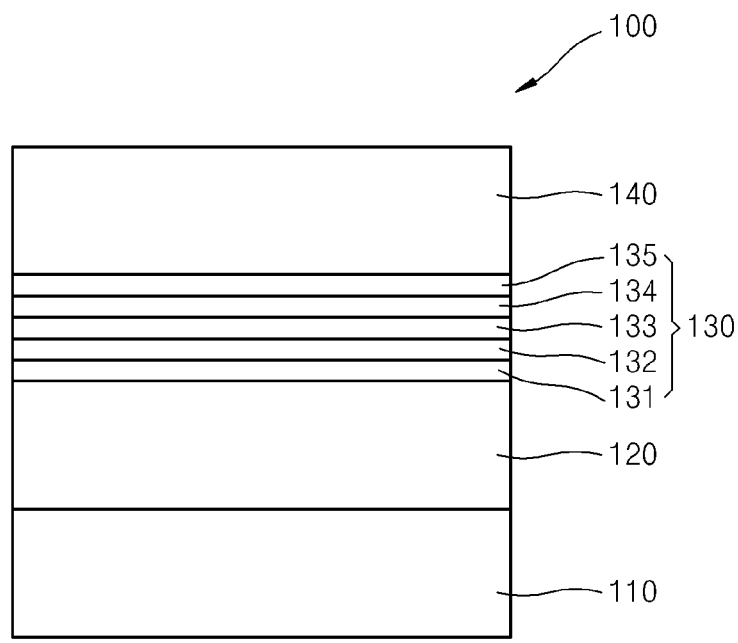
FIG. 1 is a schematic view illustrating a structure of an organic light emitting diode according to an embodiment.

The arylamine-based compound is represented by Formula 1 below:

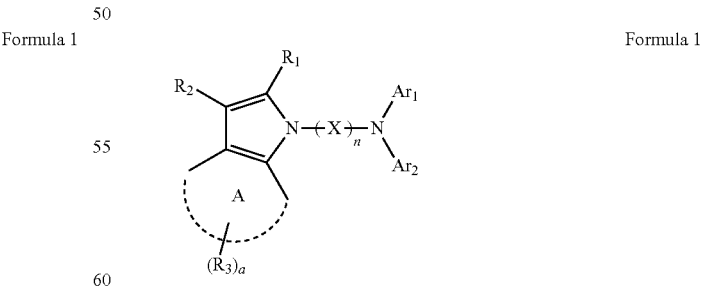

Formula 1

In Formula 1, ring A is selected from a $C_6$-$C_{20}$ aromatic ring or a $C_2$-$C_{20}$ heteroaromatic ring.

For example, in Formula 1 above, ring A may be selected from: phenyl, naphthylene, anthracene, fluorene, a spiro-fluorenylene group, phenanthrene, triphenylene, pyrene, chrysene, naphthacene, perylene, pyrrole, imidazole, pyrazole, pyridine, pyrazine, pyrimidine, pyridazine, isoindole, indole, quinoline, isoquinoline, benzoquinoline, naphthyridine, quinoxaline, quinazoline, cinnoline, carbazole, phenanthridine, acridine, phenanthroline, phenazine, benzoxazole, benzoimidazole, furan, benzofuran, thiophene, benzothiophene, thiazole, isothiazole, benzothiazole, isoxazole, oxazole, triazole, tetrazole, oxadiazole, triazine, benzoxazole, dibenzofuran, dibenzothiophene, or benzocarbazole, but is not limited thereto.

In another embodiment, in Formula 1 above, ring A may be selected from: phenyl, naphthylene, anthracene, fluorene, phenanthrene, triphenylene, pyrene, chrysene, perylene, pyridine, pyrazine, pyrimidine, quinoline, isoquinoline, benzoquinoline, carbazole, acridine, phenanthroline, phenazine, benzofuran, benzothiophene, dibenzofuran, dibenzothiophene or benzocarbazole, but is not limited thereto.

In another embodiment, in Formula 1, ring A may be selected from: benzene, naphthylene, fluorene, phenanthrene, pyrene, chrysene, perylene, pyridine, pyrazine, pyrimidine, quinoline, isoquinoline, benzoquinoline, carbazole, phenanthroline, dibenzofuran or dibenzothiophene, but is not limited thereto.

In another embodiment, in Formula 1, ring A may be any one of Formulae 2a to 2o, but the ring is not limited thereto:

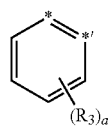
<2a>

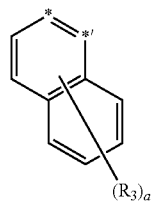
<2b>

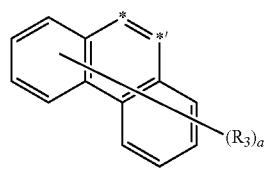
<2c>

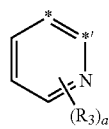
<2d>

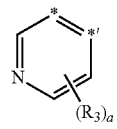
<2e>

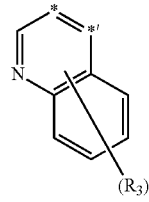
<2f>

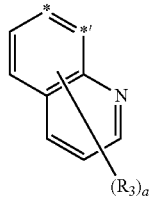
<2g>

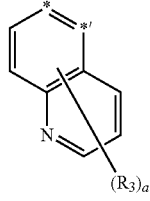
<2h>

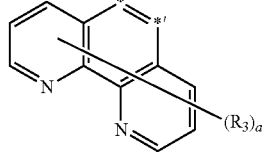
<2i>

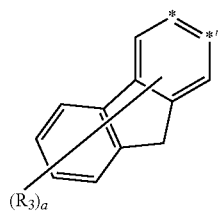
<2j>

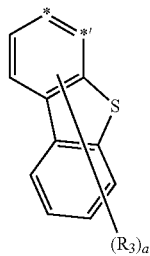
<2k>

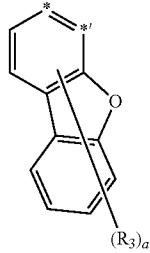
<2l>

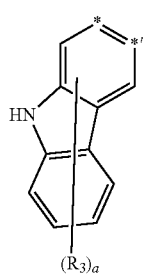
<2m>

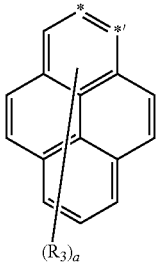

<2n>

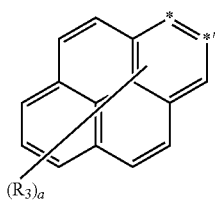

<2o>

In Formulae 2a to 2o, * and *' are each a carbon atom of Formulae 2a to 2o, * corresponds to carbon number 4 of a pyrrole ring in Formula 1, and *' is a carbon number 5 of the pyrrole ring in Formula 1.

In Formula 1, each X is independently selected from a substituted or unsubstituted $C_6$-$C_{30}$ arylene group or a substituted or unsubstituted $C_2$-$C_{30}$ heteroarylene group.

For example, in Formula 1 above, each X is independently selected from: a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted cinnolinylene group, a substituted or unsubstituted carbazolylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzooxazolylene group, a substituted or unsubstituted benzoimidazolylene group, a substituted or unsubstituted furanylene group, a substituted or unsubstituted benzofuranylene group, a substituted or unsubstituted thiophenylene group, a substituted or unsubstituted benzothienylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene, a substituted or unsubstituted oxadiazolylene group, a substituted or unsubstituted triazinylene group, a substituted or unsubstituted benzooxazolylene group, a substituted or unsubstituted dibenzofuranylene group, a substituted or unsubstituted dibenzothienylene group, or a substituted or unsubstituted benzocarbazolylene group, but X is not limited thereto.

In another embodiment, in Formula 1, each X may be independently selected from:
i) a phenylene group, a naphthylene group, an anthracenylene group, a fluorenylene group, and a pyridinylene group; or
ii) a phenylene group, a naphthylene group, an anthracenylene group, a fluorenylene group and a pyridinylene group, each substituted with at least one of:
a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or a $C_1$-$C_{10}$ alkyl group;
a $C_1$-$C_{10}$ alkyl group substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, or a phosphoric acid group or a salt thereof;
a $C_6$-$C_{16}$ aryl group or a $C_2$-$C_{16}$ heteroaryl group; or
a $C_6$-$C_{16}$ aryl group or a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, or a $C_2$-$C_{16}$ heteroaryl group; but X is not limited thereto.

In another embodiment, in Formula 1 above, each X may be independently selected from:
i) a phenylene group, a naphthylene group, a fluorenylene group, or a pyridinylene group; or
ii) a phenylene group, a naphthylene group, a fluorenylene group, or a pyridinylene group, each substituted with at least one of a deuterium atom, a fluorine atom, a cyano group, a nitro group, a methyl group, an ethyl group, an n-propyl group, or an iso-propyl group, but X is not limited thereto.

In another embodiment, in Formula 1, each X is independently selected from:
i) a phenylene group, a naphthylene group, a fluorenylene group, or a pyridinylene group; or ii) a phenylene group or a fluorenylene group, each substituted with a methyl group, but X is not limited thereto.

In Formula 1, n denotes a number of groups represented by Xs, wherein n is an integer of 1 to 5. When n is an integer of 2 or more, an n number of groups represented by Xs may be the same or different, but not limited thereto. The two or more groups represented by Xs may be connected to each other to form optionally, a substituted or unsubstituted saturated ring or a substituted or unsubstituted unsaturated ring. When the two or more groups represented by Xs are connected to each other, the two or more groups represented by Xs may be connected by a linker selected from: —O—, —S—, or —Si($Q_1$)($Q_2$)-, wherein, $Q_1$ and $Q_2$ are each independently a methyl group, an ethyl group, an n-propyl group, an iso-propyl group, an n-butyl group, a sec-butyl group, an iso-butyl group, or a tert-butyl group, but the linker is not limited thereto.

For example, in Formula 1, n may be an integer of 1 to 3, but n is not limited thereto.

For example, in Formula 1, $(X)_n$ may be any one of Formulae 3a to 3n below, but is not limited thereto:

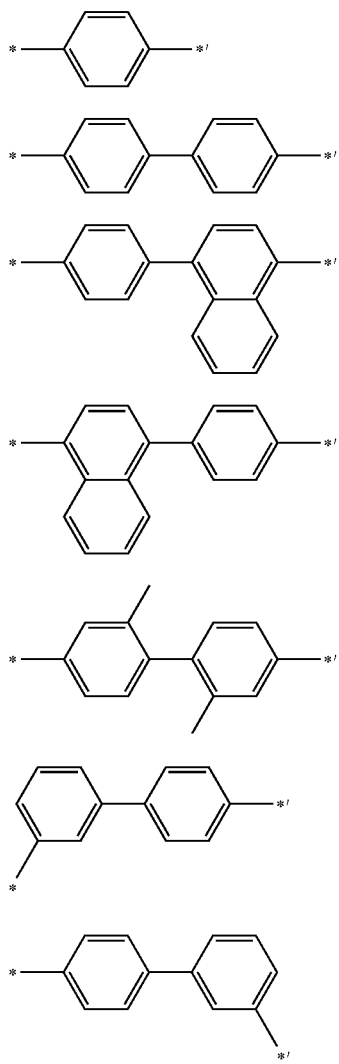

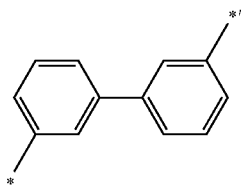

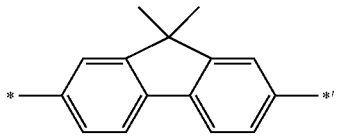

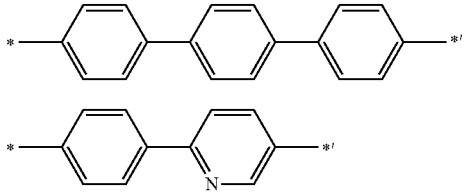

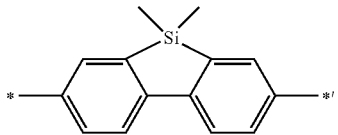

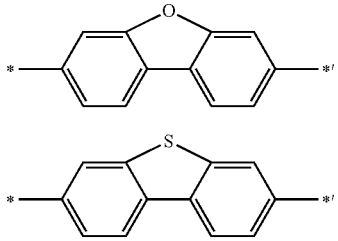

In Formulae 3a to 3n, * is a binding site to the nitrogen atom of a pyrrole ring in Formula 1 and *' is a binding site to the other nitrogen atom.

In Formula 1, each of $Ar_1$ and $Ar_2$ is independently selected from a substituted or unsubstituted $C_6$-$C_{30}$ aryl group or a substituted or unsubstituted $C_2$-$C_{30}$ heteroaryl group.

For example, in Formula 1, each of $Ar_1$ and $Ar_2$ is independently selected from: a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothienyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, a substituted or unsubstituted dibenzothienyl group, benzocarbazolyl group, a benzosilolyl group or a dibenzosilolyl group, but is not limited thereto.

In another embodiment, in Formula 1, each of $Ar_1$ and $Ar_2$ is independently at least one selected from:

i) a phenyl group, a naphthyl group, an anthryl group, a fluorenyl group, a benzofuranyl group, a benzothienyl group, a benzosilolyl group, a dibenzofuranyl group, a dibenzothienyl group, or a dibenzosilolyl group; or ii) a phenyl group, a naphthyl group, an anthryl group, a fluorenyl group, a benzofuranyl group, a benzothienyl group, a benzosilolyl group, a dibenzofuranyl group, a dibenzothienyl group, or a dibenzosilolyl group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or —$Si(Q_3)(Q_4)(Q_5)$ wherein $Q_3$ to $Q_5$ are each independently a $C_1$-$C_{10}$ alkyl group;

a $C_1$-$C_{10}$ alkyl group substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or —$Si(Q_3)(Q_4)(Q_5)$ wherein $Q_3$ to $Q_5$ are each independently a $C_1$-$C_{10}$ alkyl group;

a $C_6$-$C_{16}$ aryl group or a $C_2$-$C_{16}$ heteroaryl group; or a $C_6$-$C_{16}$ aryl group or a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, a $C_2$-$C_{16}$ heteroaryl group, or —$Si(Q_3)(Q_4)(Q_5)$ wherein $Q_3$ to $Q_5$ are each independently a $C_1$-$C_{10}$ alkyl group, but are not limited thereto.

In another embodiment, in Formula 1, each of $Ar_1$ and $Ar_2$ is independently selected from:

i) a phenyl group, a naphthyl group, a fluorenyl group, a dibenzothienyl group or a dibenzosilolyl group; or ii) a phenyl group, a naphthyl group, a fluorenyl group, a dibenzothienyl group, or a dibenzosilolyl group substituted with at least one of a deuterium atom, a fluorine atom, a cyano group, a nitro group, a methyl group, an ethyl group, an n-propyl group, an iso-propyl group, an n-butyl group, a sec-butyl group, an iso-butyl group, a tert-butyl group, or —$Si(Q_3)(Q_4)(Q_5)$ wherein $Q_3$ to $Q_5$ are each independently a methyl group, an ethyl group, n-propyl group, iso-propyl group, n-butyl group, sec-butyl group, iso-butyl group, or a tert-butyl group;

a methyl group, an ethyl group, an n-propyl group, an iso-propyl group, an n-butyl group, a sec-butyl group, an iso-butyl group, or a tert-butyl group, each substituted with at least one of a deuterium atom, a fluorine atom, a cyano group, a nitro group, or —$Si(Q_3)(Q_4)(Q_5)$ wherein $Q_3$ to $Q_5$ are each independently a methyl group, an ethyl group, n-propyl group, iso-propyl group, n-butyl group, sec-butyl group, iso-butyl group, or a tert-butyl group;

a phenyl group, a naphthyl group, an anthracenyl group, a fluorenyl group, a benzothienyl group, a dibenzothienyl group, a pyridyl group, a pyrimidyl group, a triazinyl group, or a carbazolyl group; or a phenyl group, a naphthyl group, an anthracenyl group, a fluorenyl group, a benzothienyl group, a dibenzothienyl group, a pyridyl group, a pyrimidyl group, a triazinyl group, or a carbazolyl group, each substituted with a deuterium atom, a fluorine atom, a cyano group, a nitro group, a methyl group, an ethyl group, an n-propyl group, an iso-propyl group, an n-butyl group, a sec-butyl group, an iso-butyl group, a tert-butyl group, a phenyl group, a naphthyl group, an anthracenyl group, a fluorenyl group, a benzothienyl group, a dibenzothienyl group, a pyridyl group, a pyrimidyl group, a triazinyl group, a carbazolyl group, or —$Si(Q_3)(Q_4)(Q_5)$ wherein $Q_3$ to $Q_5$ are each independently a methyl group, an ethyl group, n-propyl group, iso-propyl group, n-butyl group, sec-butyl group, iso-butyl group, or a tert-butyl group; but are not limited thereto.

In another embodiment, in Formula 1, each of $Ar_1$ and $Ar_2$ is independently selected from:

i) a phenyl group, a naphthyl group, a fluorenyl group, a dibenzothienyl group, or a dibenzosilolyl group; or ii) a phenyl group, a naphthyl group, a fluorenyl group, a dibenzothienyl group, or a dibenzosilolyl group, each substituted with at least one of a deuterium atom, a fluorine atom, a cyano group, a nitro group, —$Si(CH_3)_3$, or a methyl group;

a methyl group substituted with at least one of a deuterium atom, a fluorine atom, a cyano group, a nitro group or —$Si(CH_3)_3$;

a phenyl group, a fluorenyl group, a dibenzothienyl group, or a pyridyl group; or a phenyl group, a fluorenyl group, a dibenzothienyl group, or a pyridyl group, each substituted with at least one of a deuterium atom, a fluorine atom, a cyano group, a nitro group, —Si(CH₃)₃, a methyl group, or a phenyl group; but is not limited thereto.

In another embodiment, in Formula 1, each of $Ar_1$ and $Ar_2$ is independently any one of Formulae 4a to 4s, but is not limited thereto:

<4a>
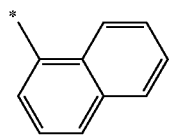

<4b>
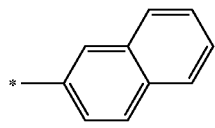

<4c>
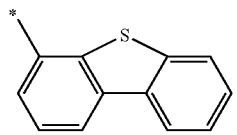

<4d>
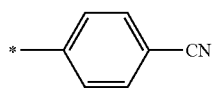

<4e>
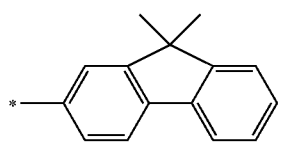

<4f>
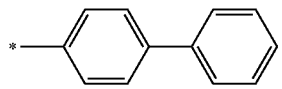

<4g>
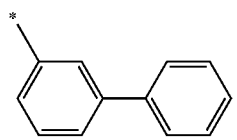

<4h>
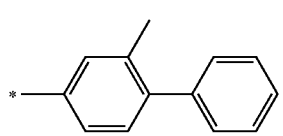

<4i>
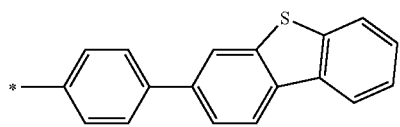

<4j>
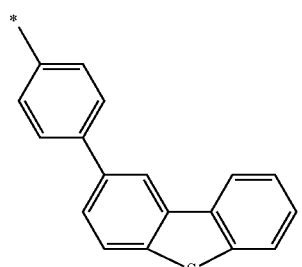

<4k>
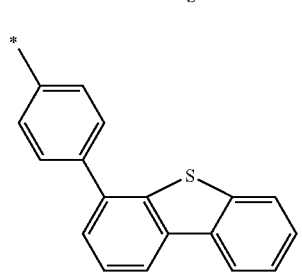

<4l>
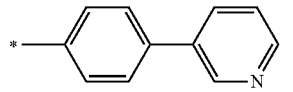

<4m>
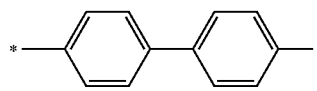

<4n>
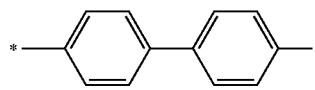

<4o>
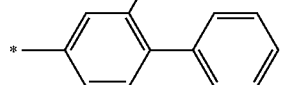

<4p>
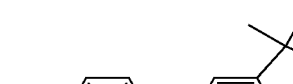

<4q>
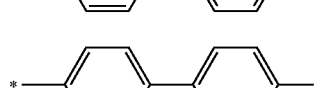

<4r>
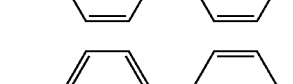

<4s>
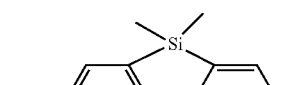

In Formulae 4a to 4s, * is a binding site to the nitrogen atom.

In Formula 1 above, each of $R_1$, $R_2$ and each of $R_3$ is independently selected from: a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or a substituted or unsubstituted $C_2$-$C_{30}$ heteroaryl group.

For example, in Formula 1, each of $R_1$, $R_2$ and each of $R_3$ may be independently selected from: a hydrogen atom, a deuterium atom, a halogen atom, a cyano group, or a nitro group; a methyl group, an ethyl group, an n-propyl group, an iso-propyl group, an n-butyl group, a sec-butyl group, an iso-butyl group, or a tert-butyl group; or a phenyl group, a naphthyl group, an anthracenyl group, a fluorenyl group, a pyridyl group, a pyrimidyl group, a triazinyl group, or a carbazolyl group; but is not limited thereto.

In another embodiment, in Formula 1, each of $R_1$, $R_2$ and each of $R_3$ is independently selected from: a methyl group, an ethyl group, an n-propyl group, an iso-propyl group, an n-butyl group, a sec-butyl group, an iso-butyl group, or a tert-butyl group; or a phenyl group, a naphthyl group, an anthracenyl group, or a fluorenyl group; but is not limited thereto.

In another embodiment, in Formula 1, each of $R_1$, $R_2$ and each of $R_3$ may be independently selected from a methyl group or a phenyl group, but is not limited thereto.

In Formula 1, a represents a number of groups represented by $R_3$s, wherein a is an integer of 0 to 4. When a is an integer of 2 or more, the two or more groups represented by $R_3$s may be the same or different, but is not limited thereto.

For example, in Formula 1, a may be an integer of 0 to 2, but is not limited thereto.

In an embodiment, Formula 1 may be represented by any one of Formulae 1a to 1d below, but is not limited thereto:

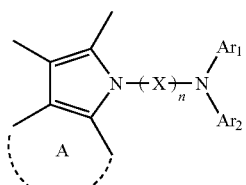

Formula 1a

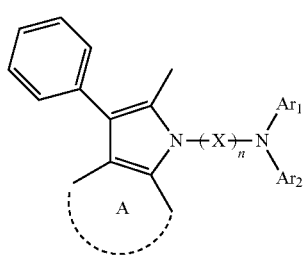

Formula 1b

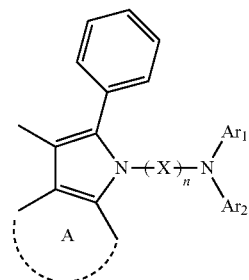

Formula 1c

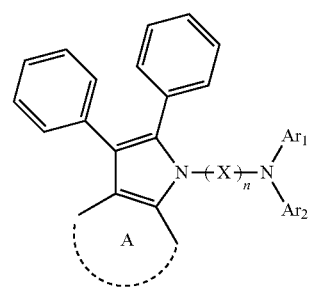

Formula 1d

In Formulae 1a to 1d, ring A is any one of Formulae 2a to 2o below:

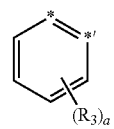

<2a>

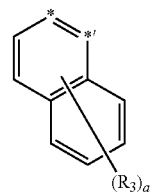

<2b>

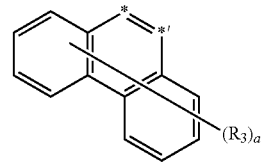

<2c>

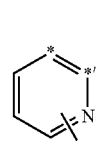

<2d>

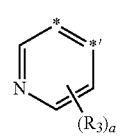

<2e>

-continued
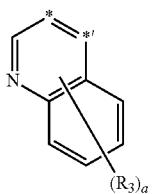
<2f>
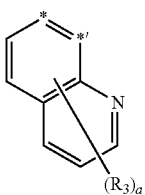
<2g>
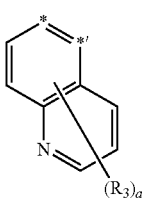
<2h>
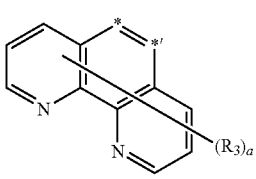
<2i>
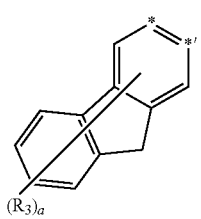
<2j>
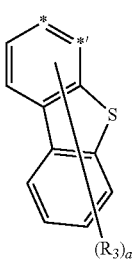
<2k>
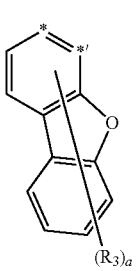
<2l>
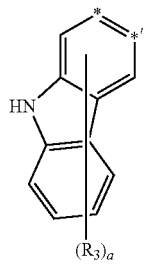
<2m>
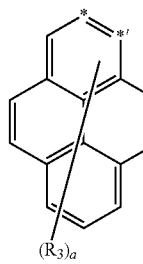
<2n>
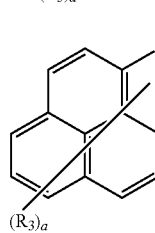
<2o>
In Formulae 2a to 2o, * corresponds to a carbon number 4 of a pyrrole ring in Formula 1, *' corresponds to carbon number 5 of pyrrole ring in Formula 1; and
a moiety represented by "$(X)_n$" is any one of Formulae 3a to 3n below:
<3a>
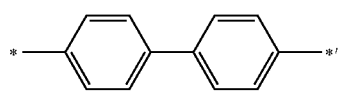
<3b>
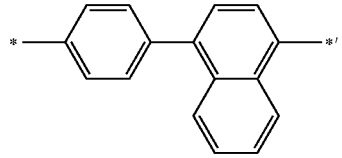
<3c>
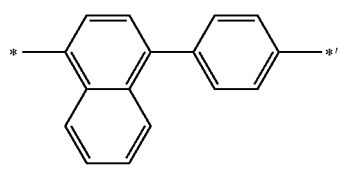
<3d>

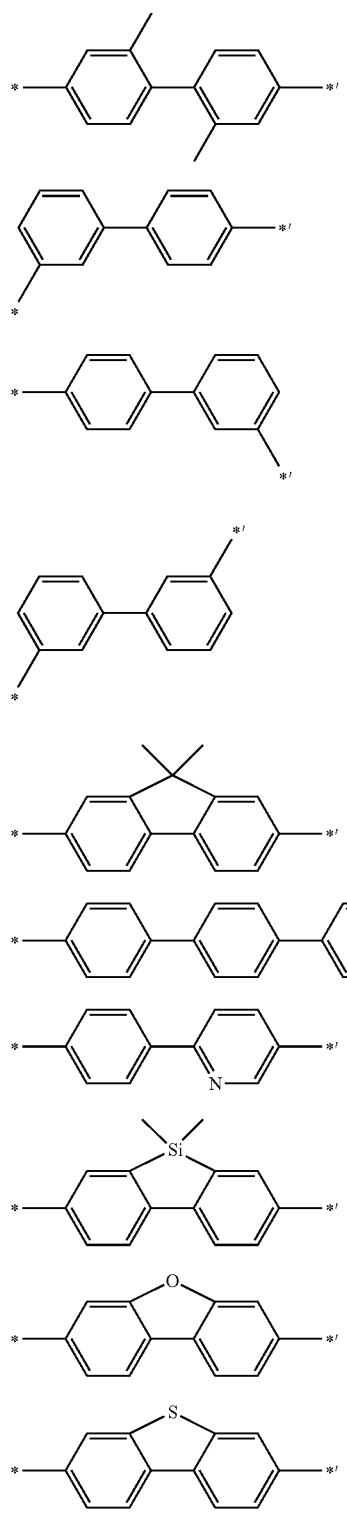
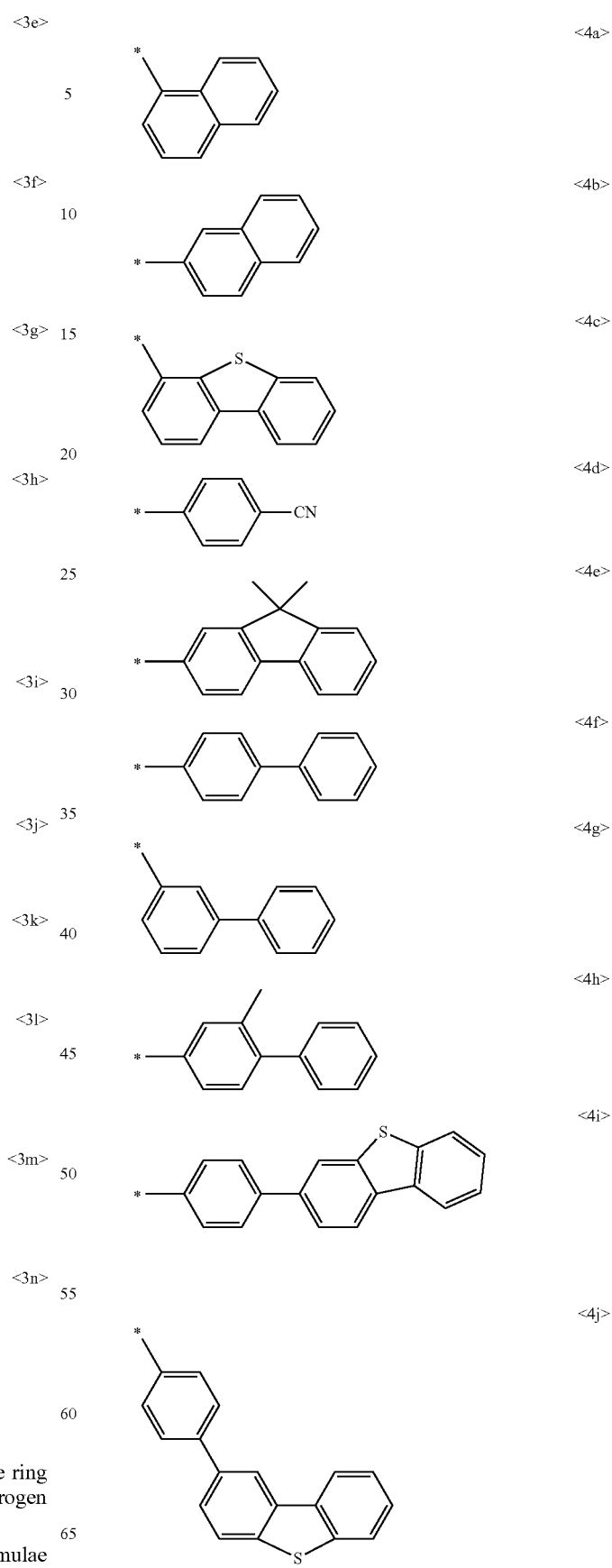
In Formulae 3a to 3n,
* is a binding site to the nitrogen atom in a pyrrole ring of Formula 1 and *' is a binding site to the other nitrogen atom;
each of $Ar_1$ and $Ar_2$ is independently any one of Formulae 4a to 4s below:

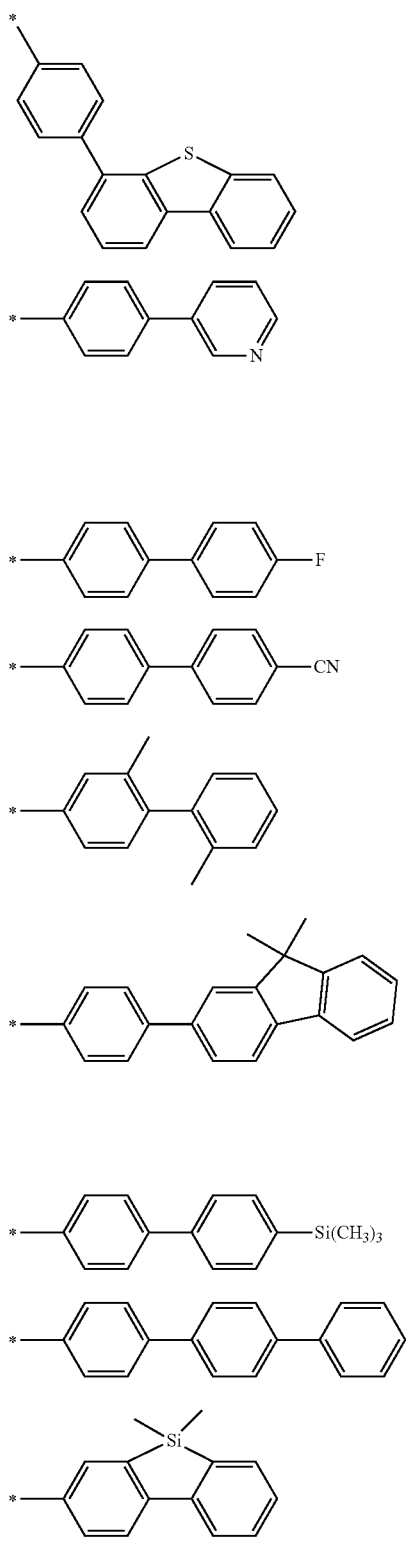
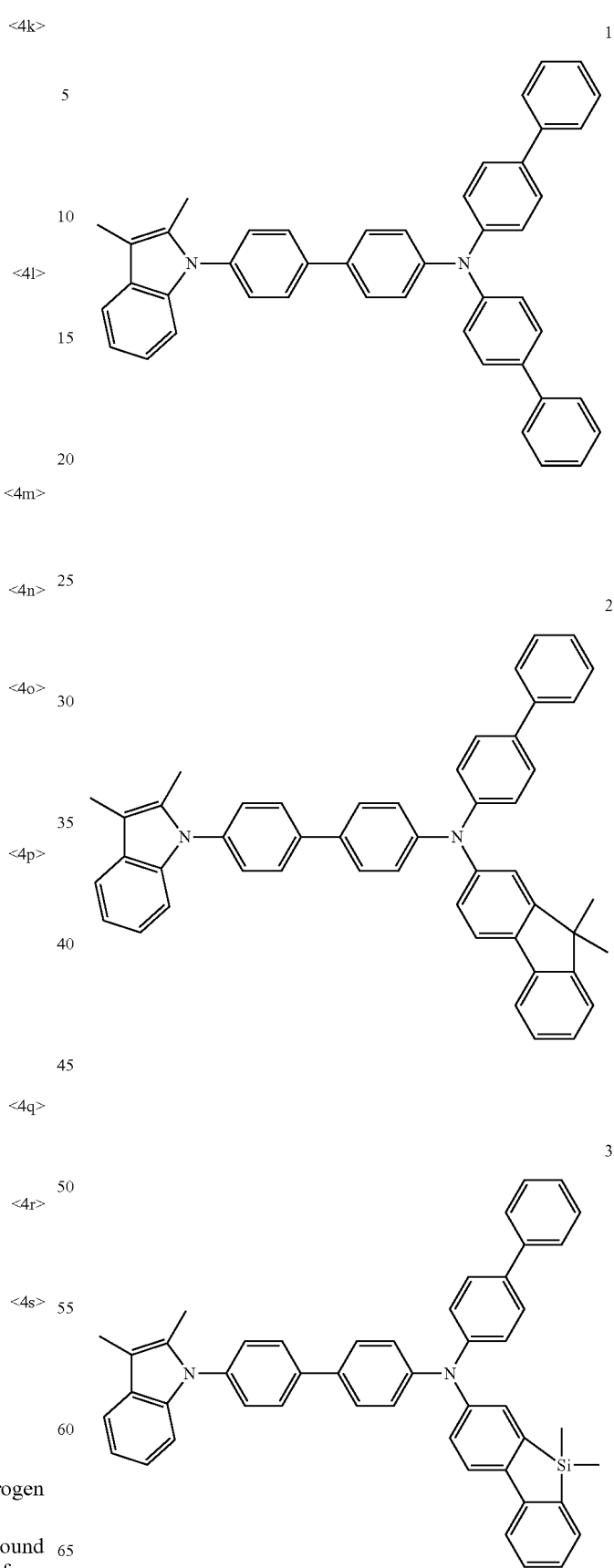
In Formulae 4a to 4s, * is a binding site to the nitrogen atom.
In another embodiment, the arylamine-based compound represented by Formula 1 above may be selected from Compounds 1 to 84 below, but are not limited thereto:

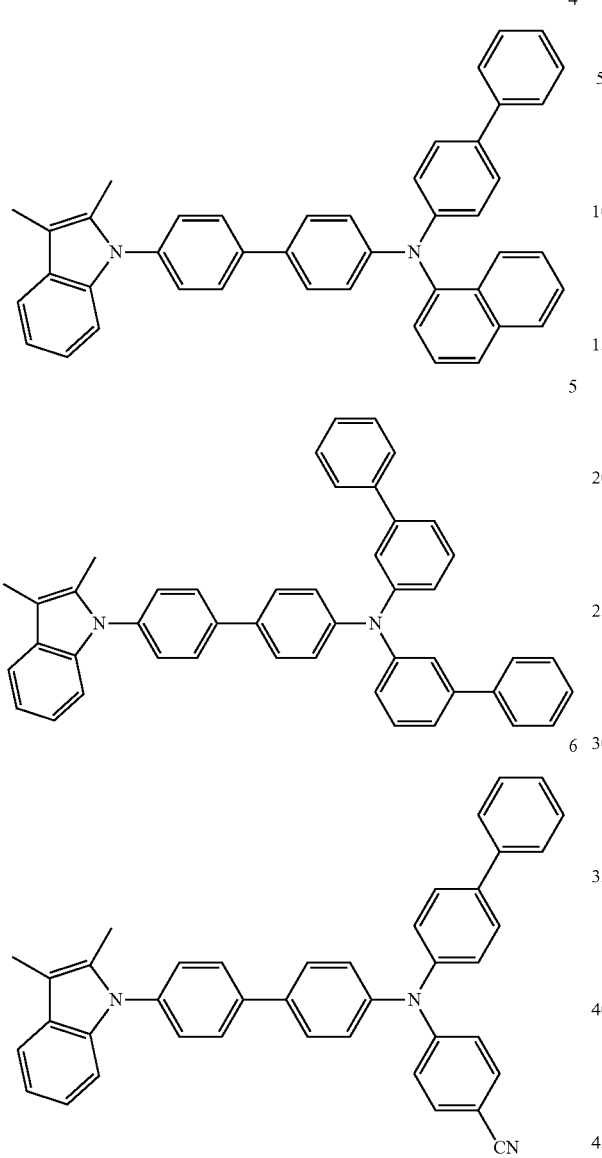
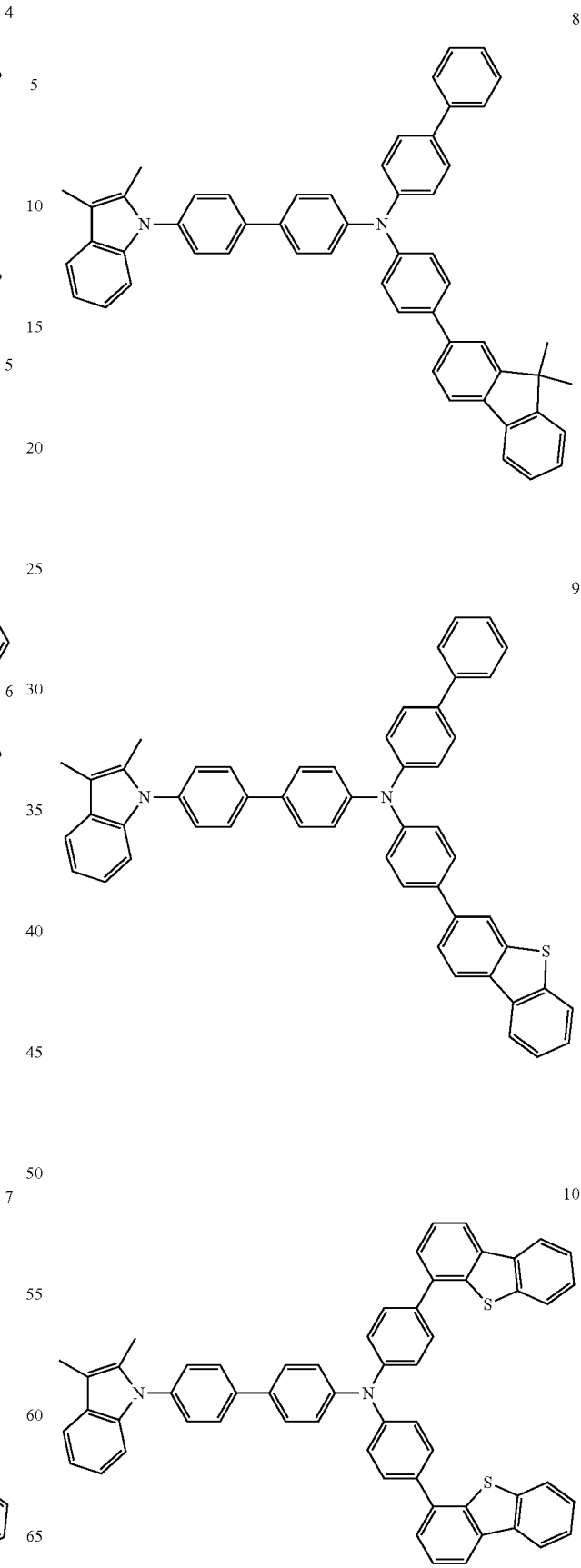

11
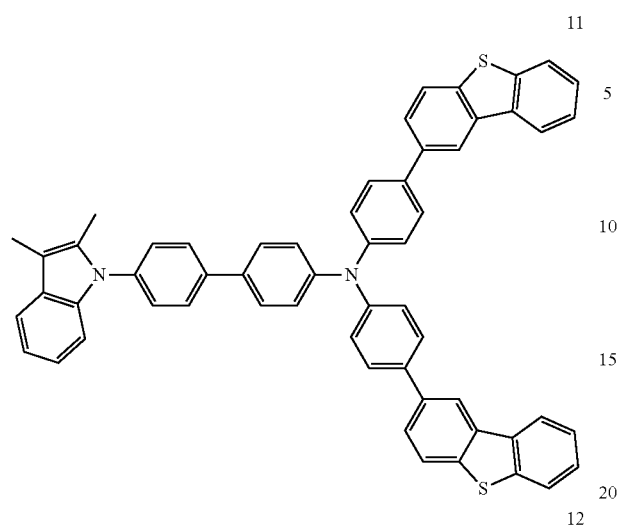
12
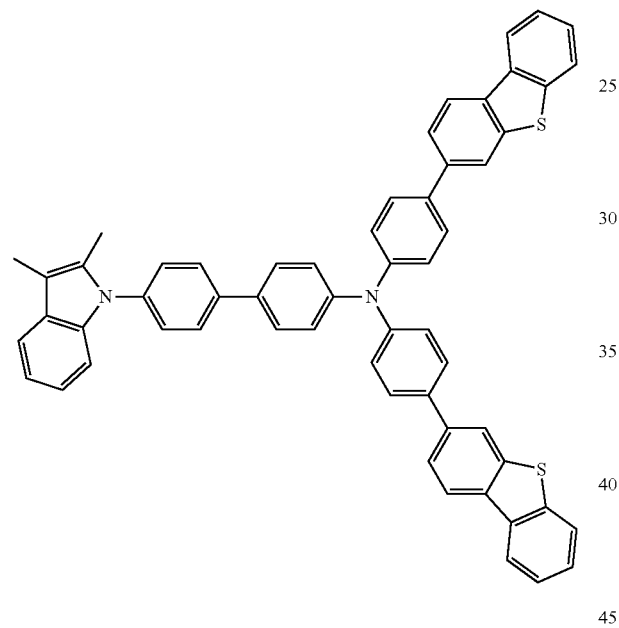
13
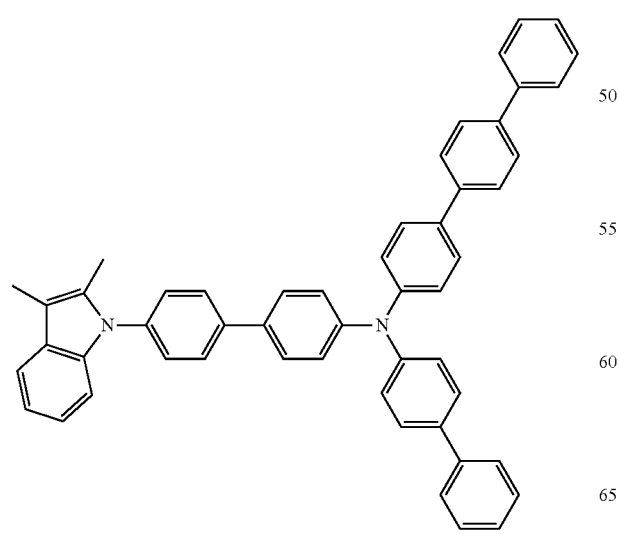
14
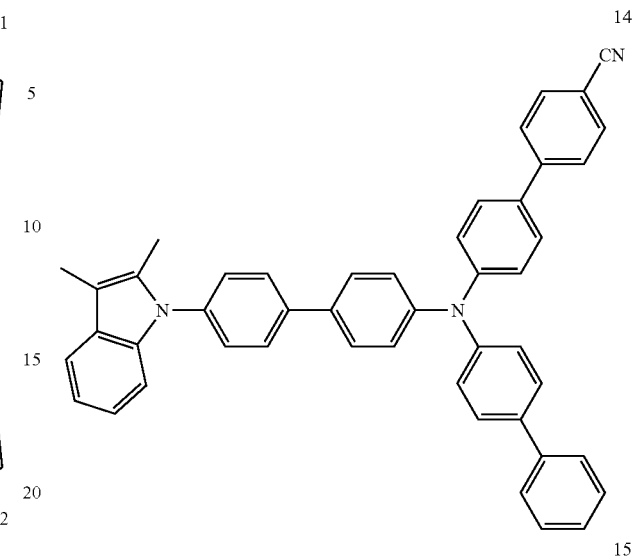
15
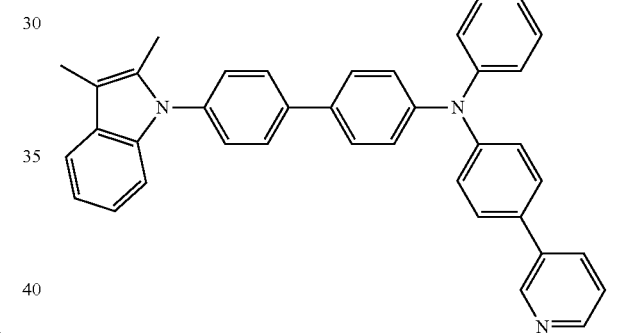
16
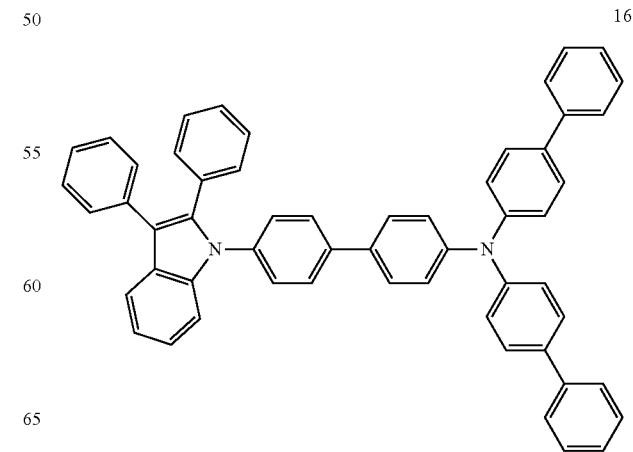

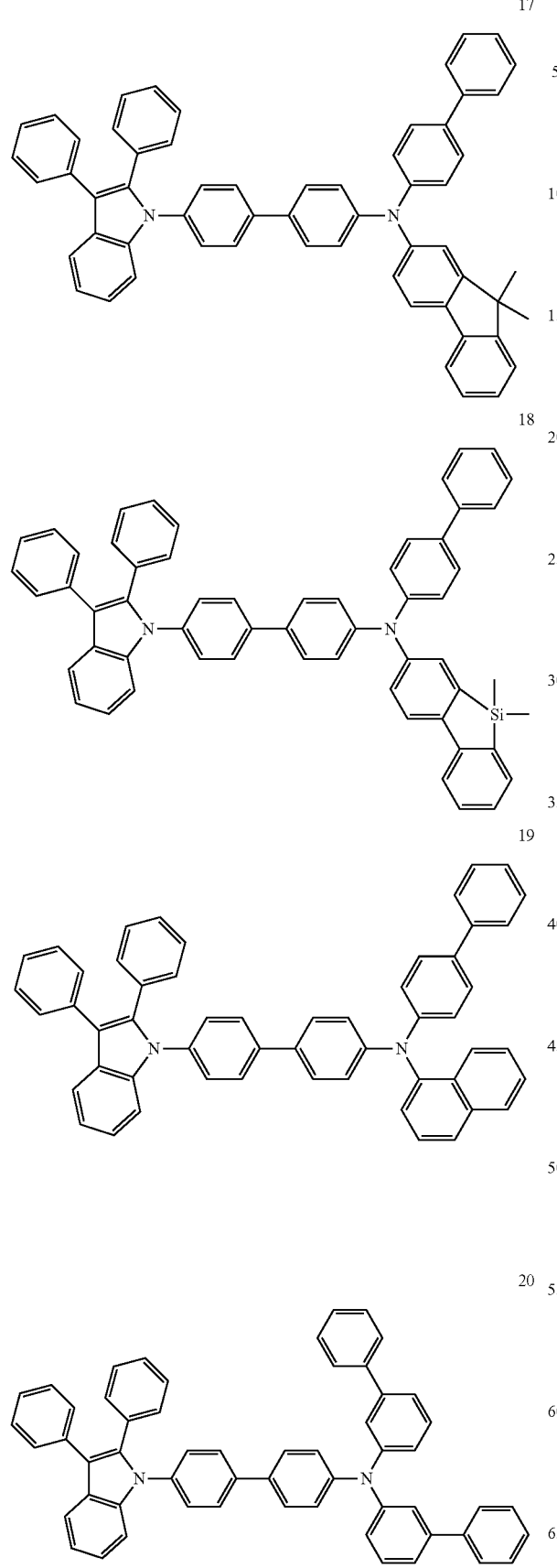
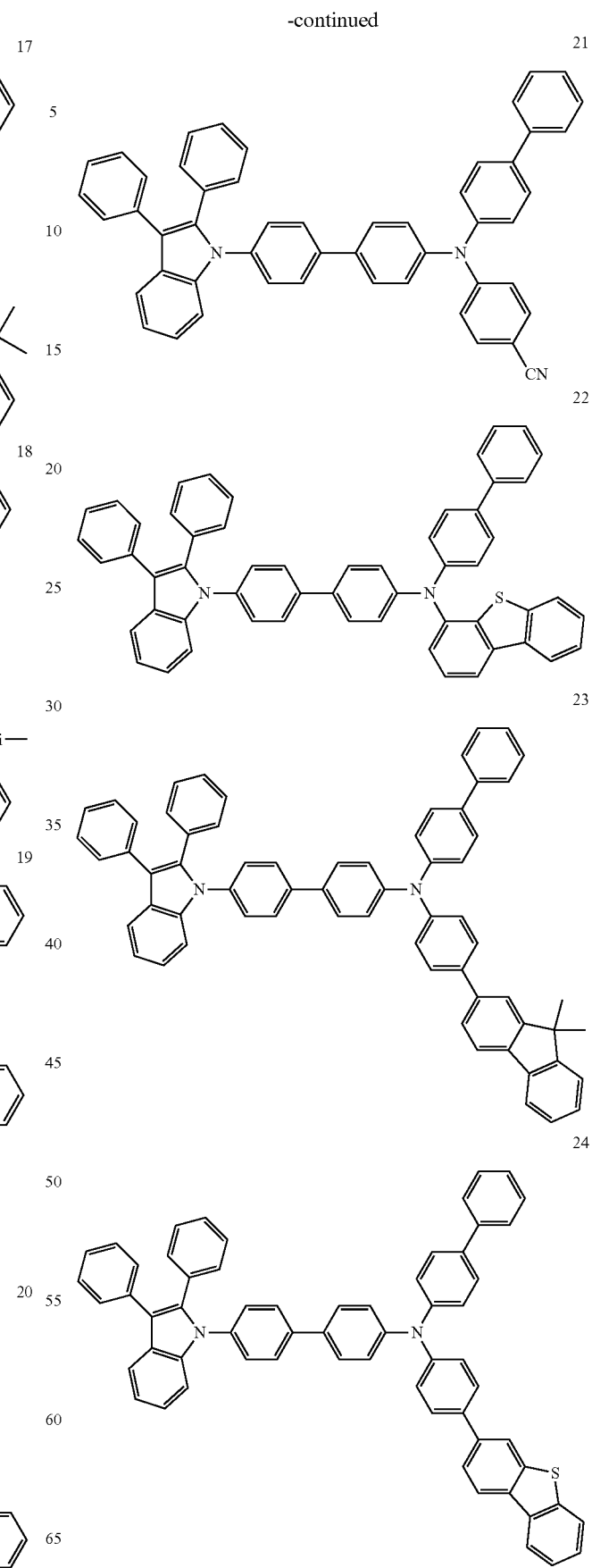

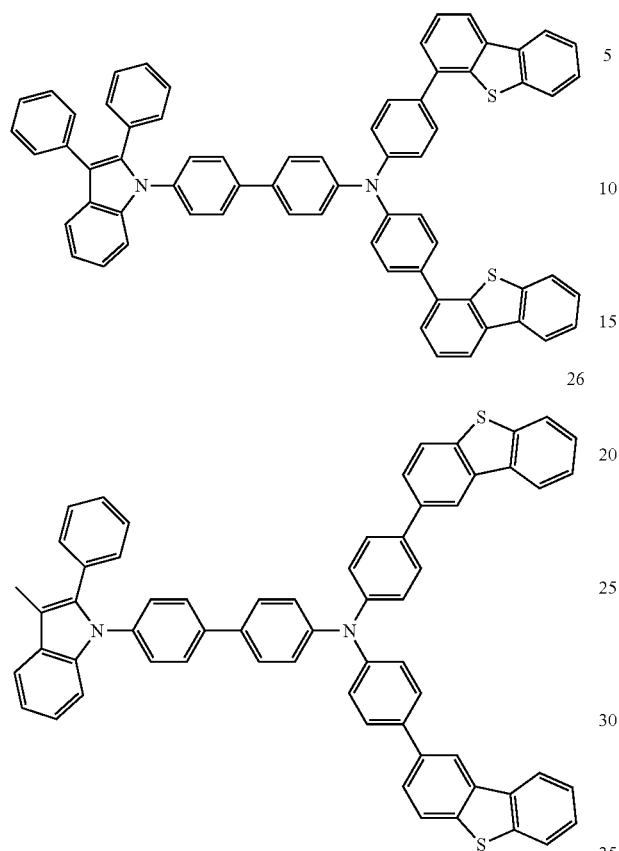
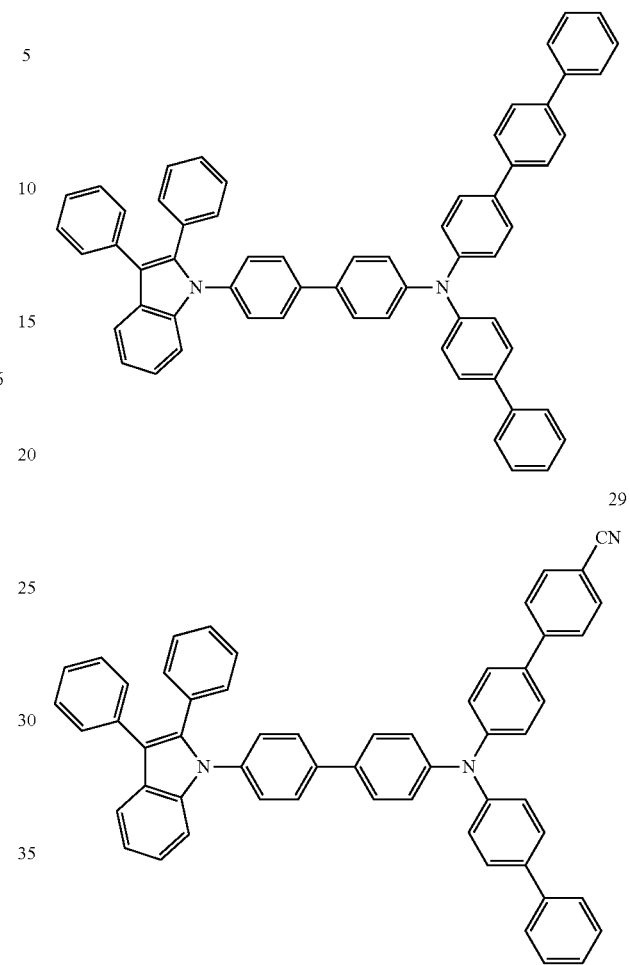
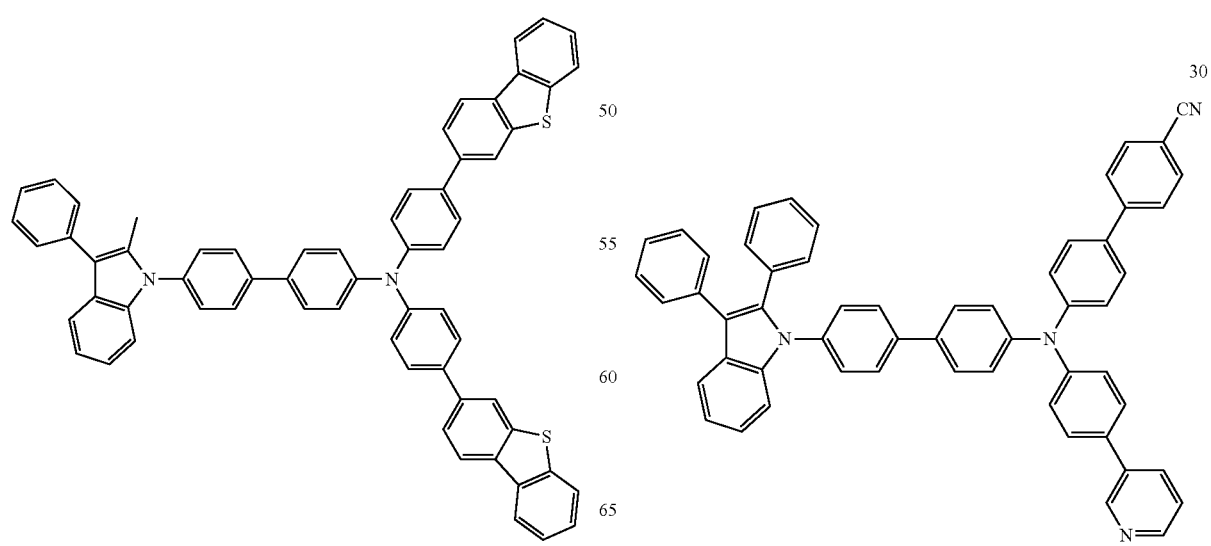

31 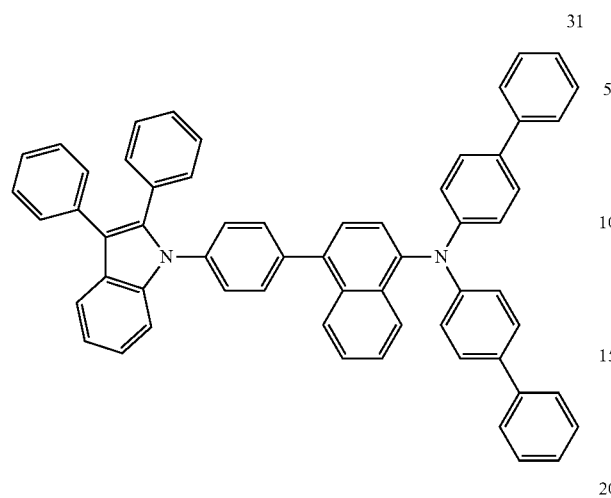
34 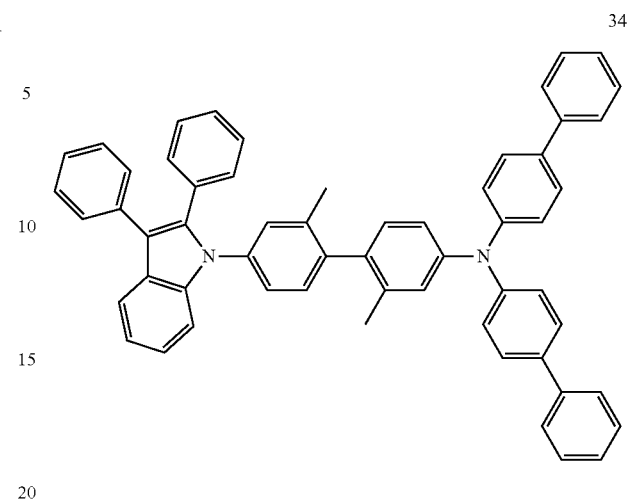
32 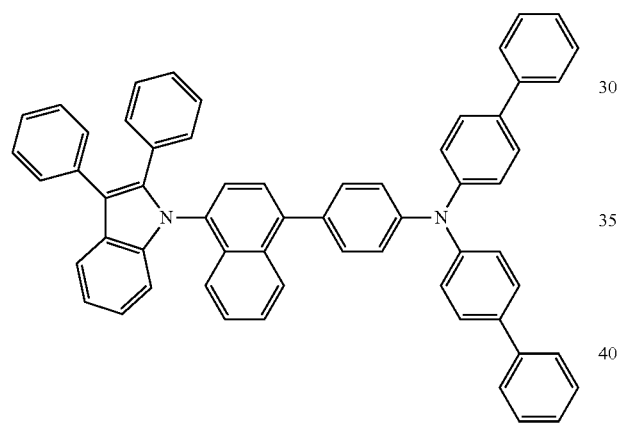
35 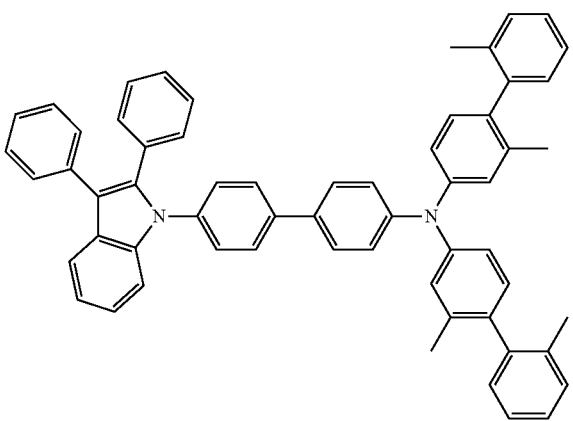
33 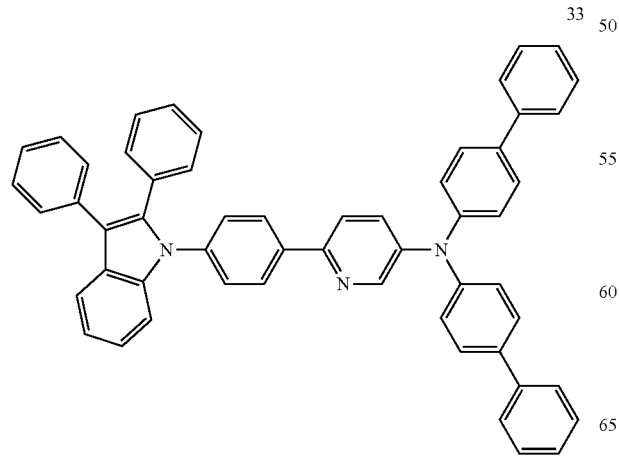
36 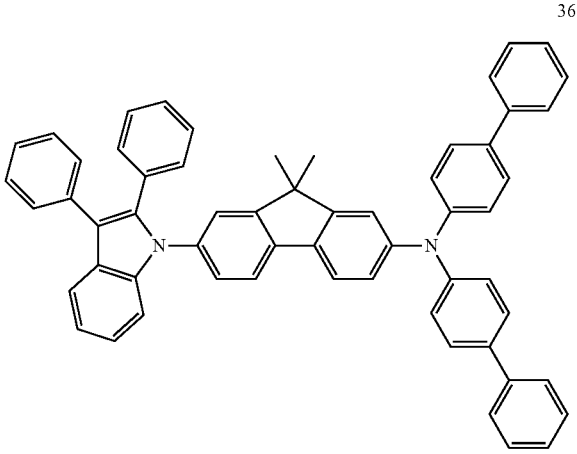

-continued
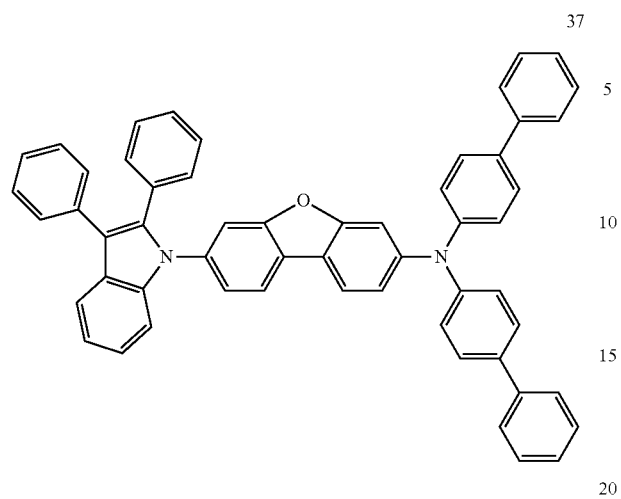
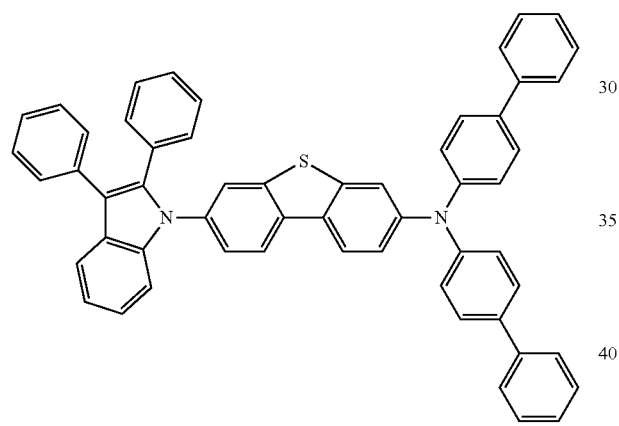
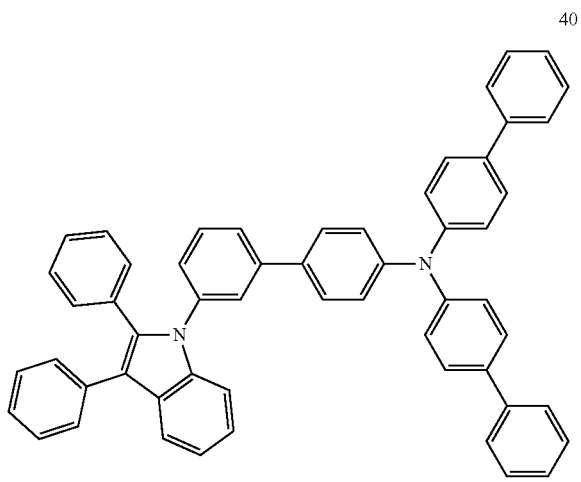
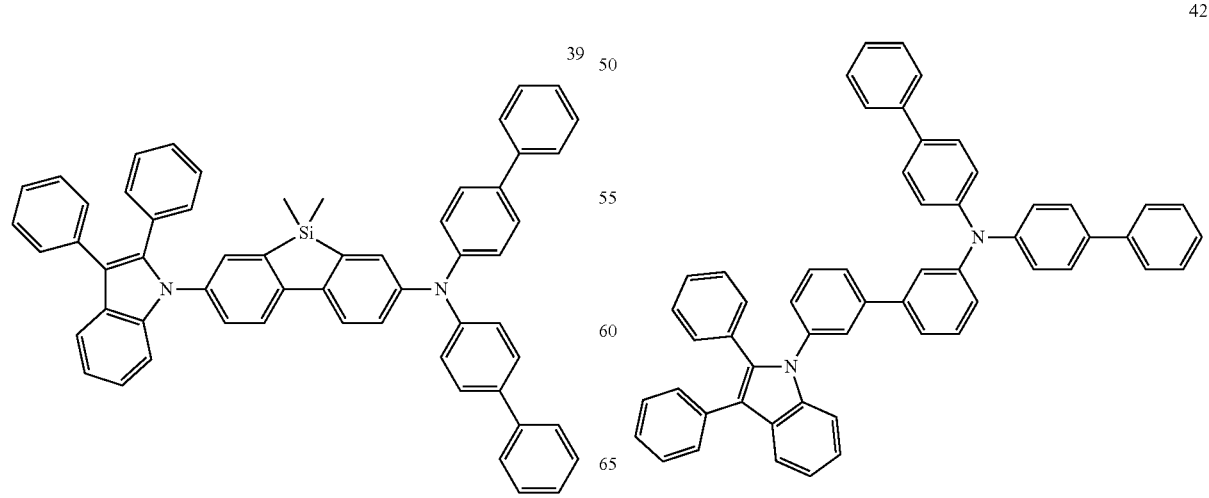

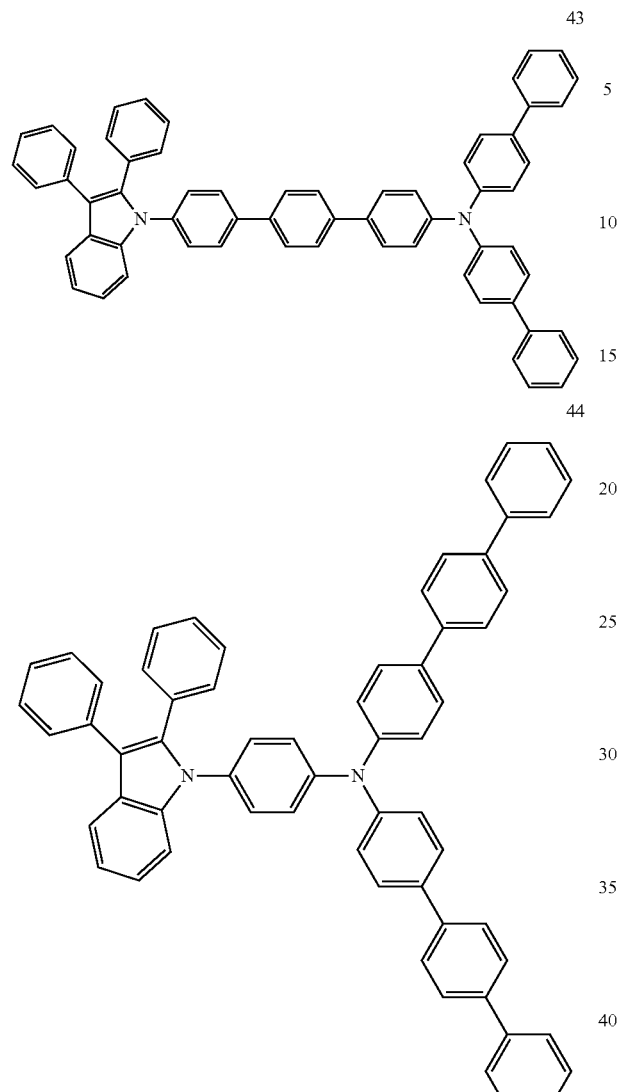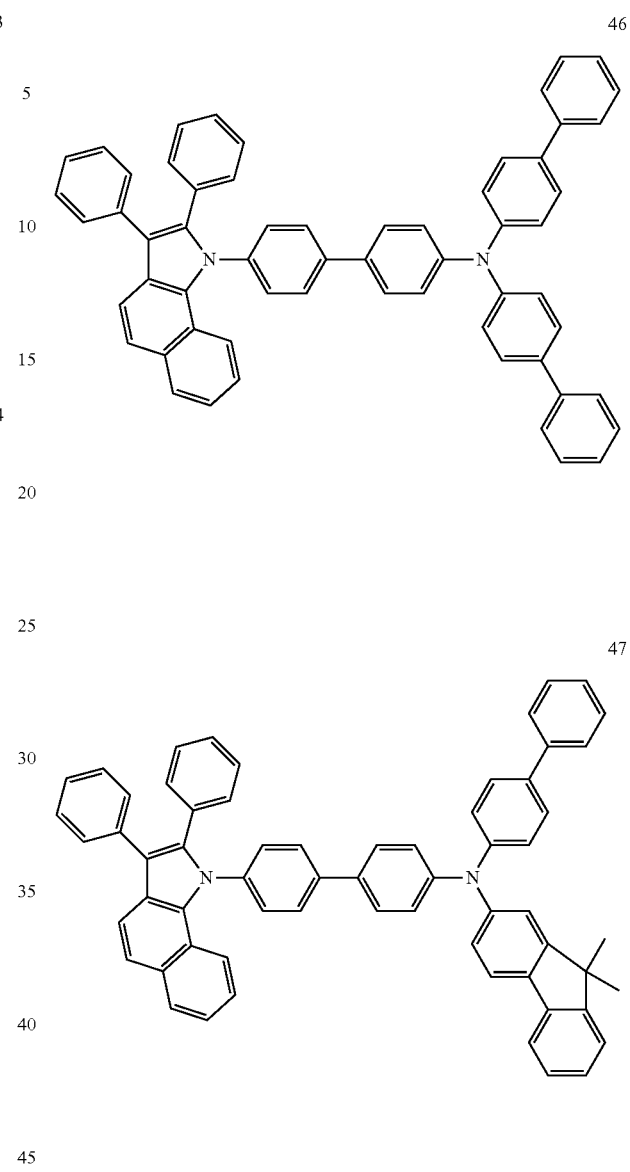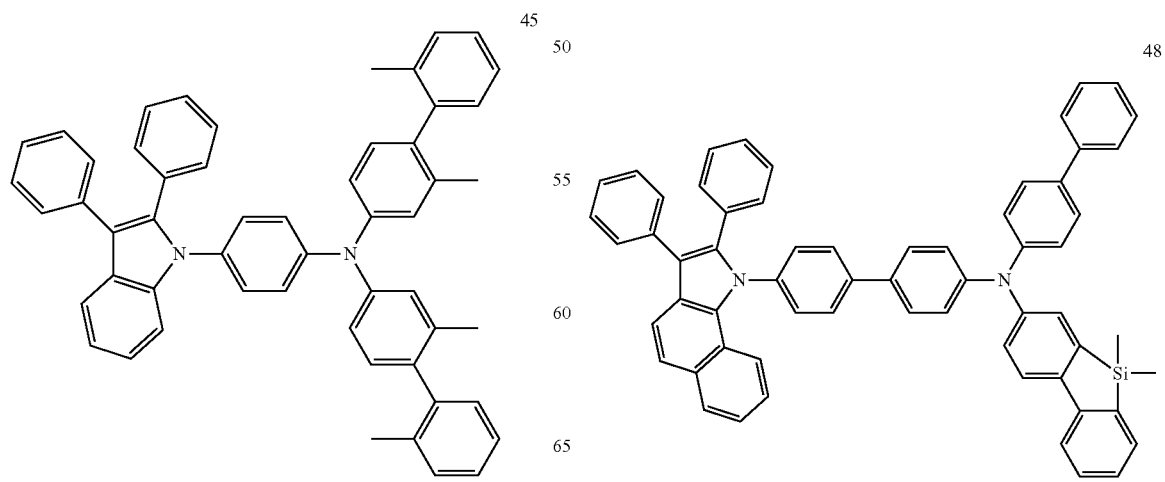

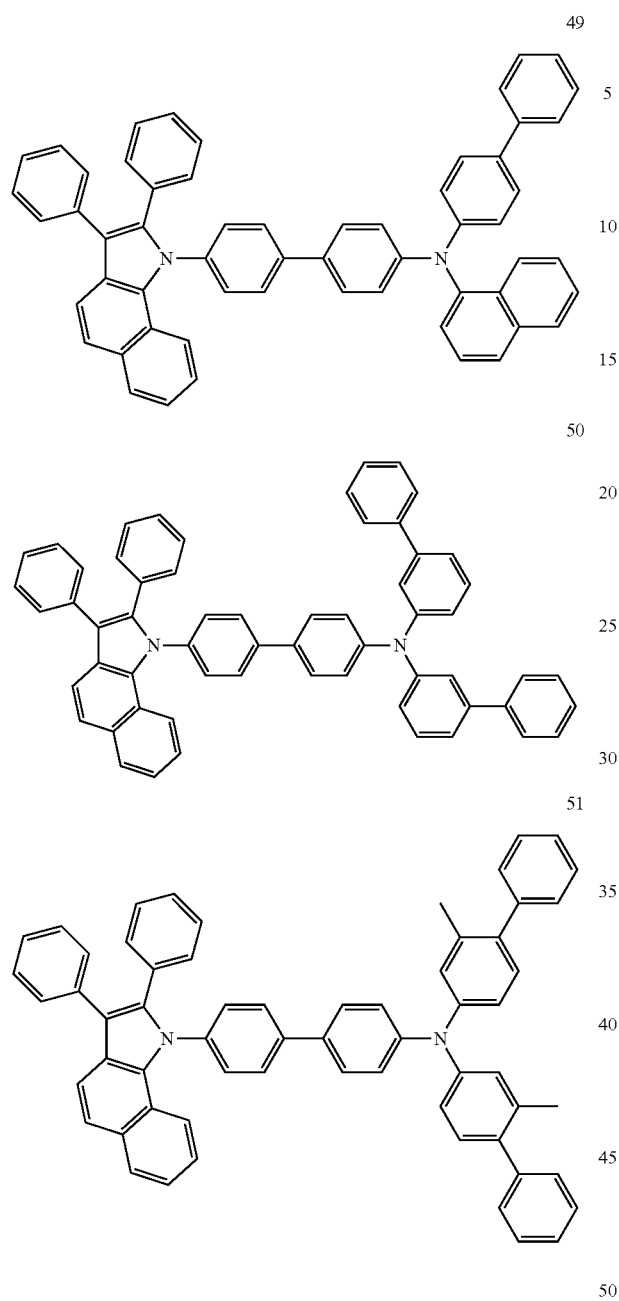
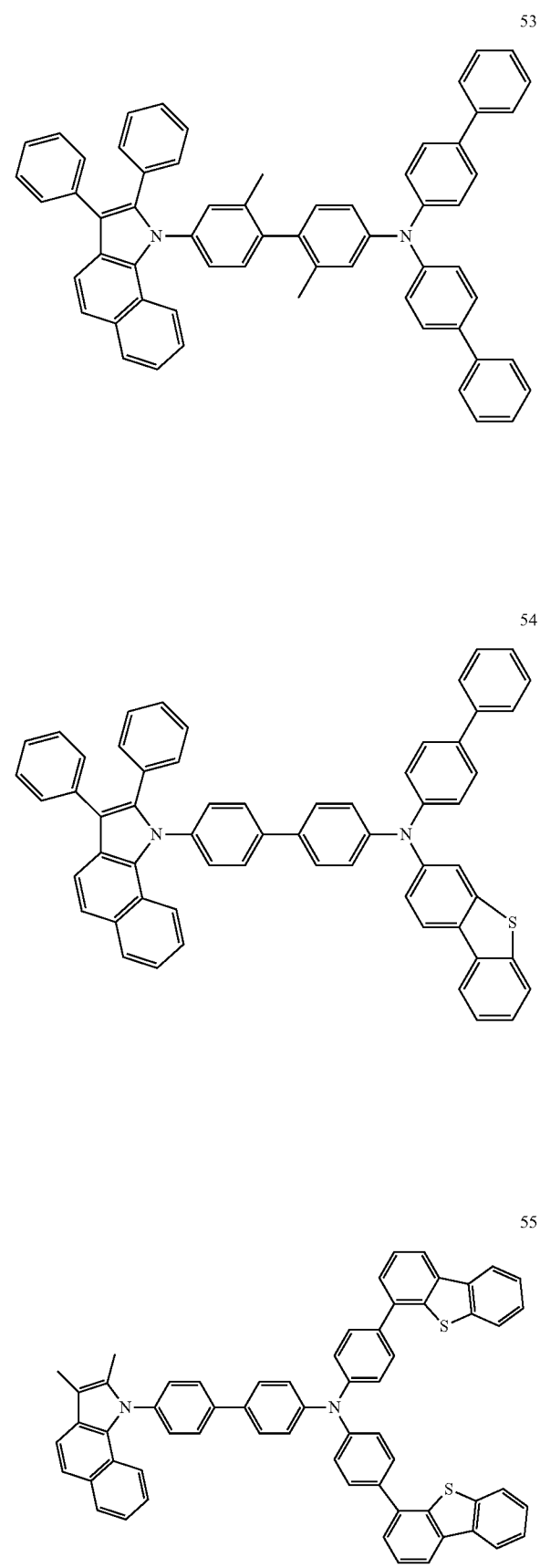

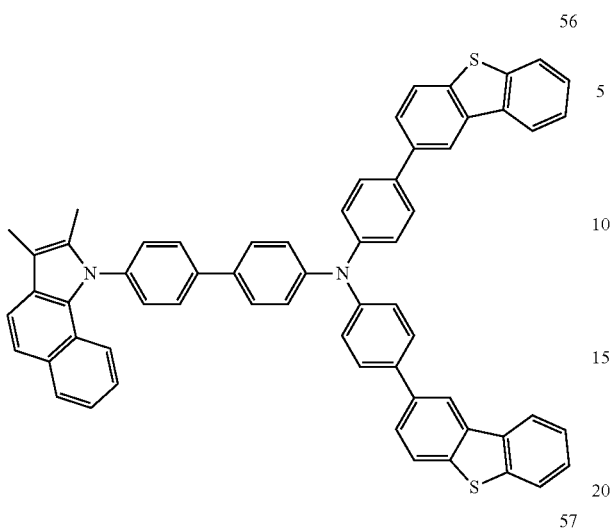
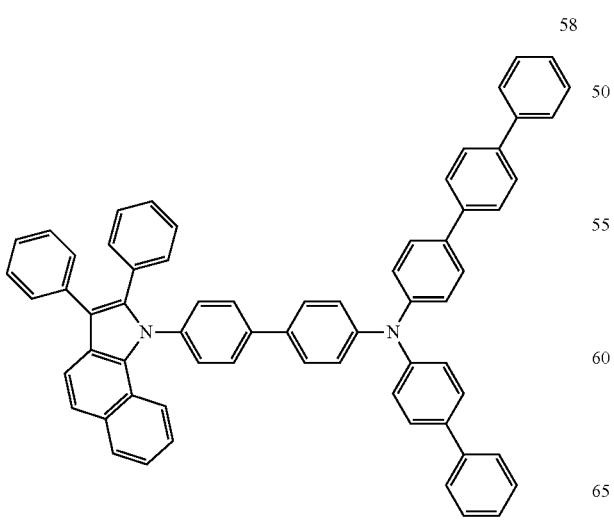
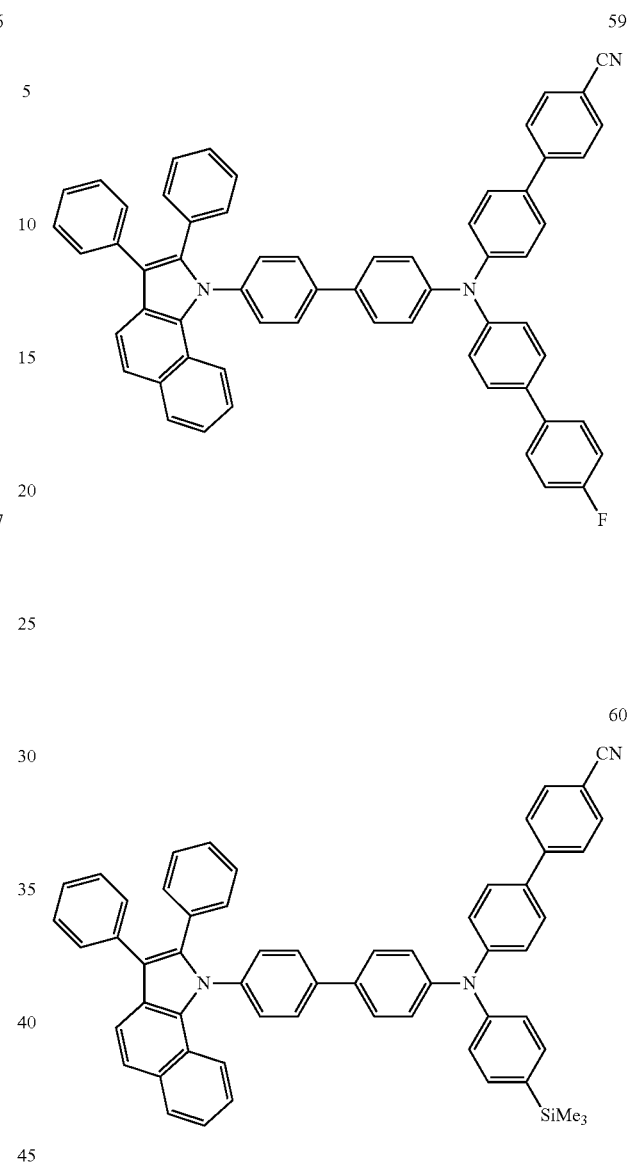
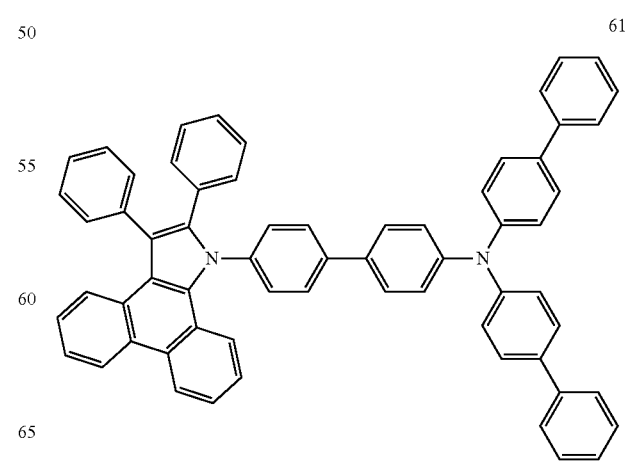

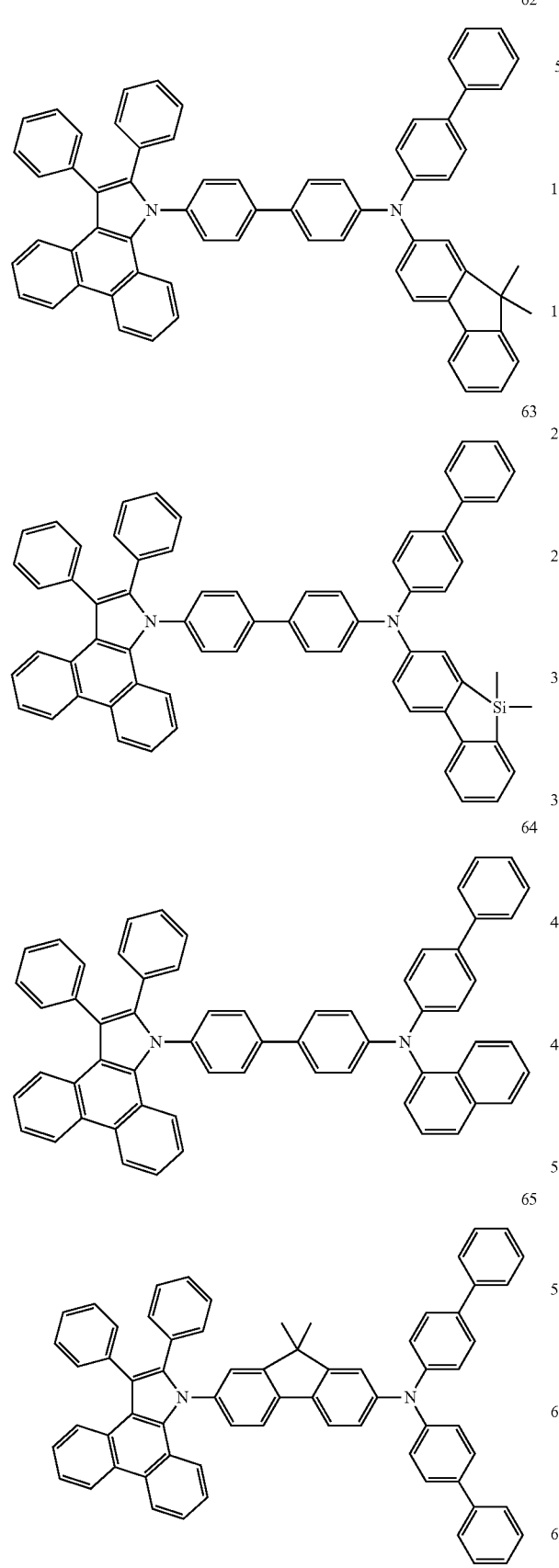
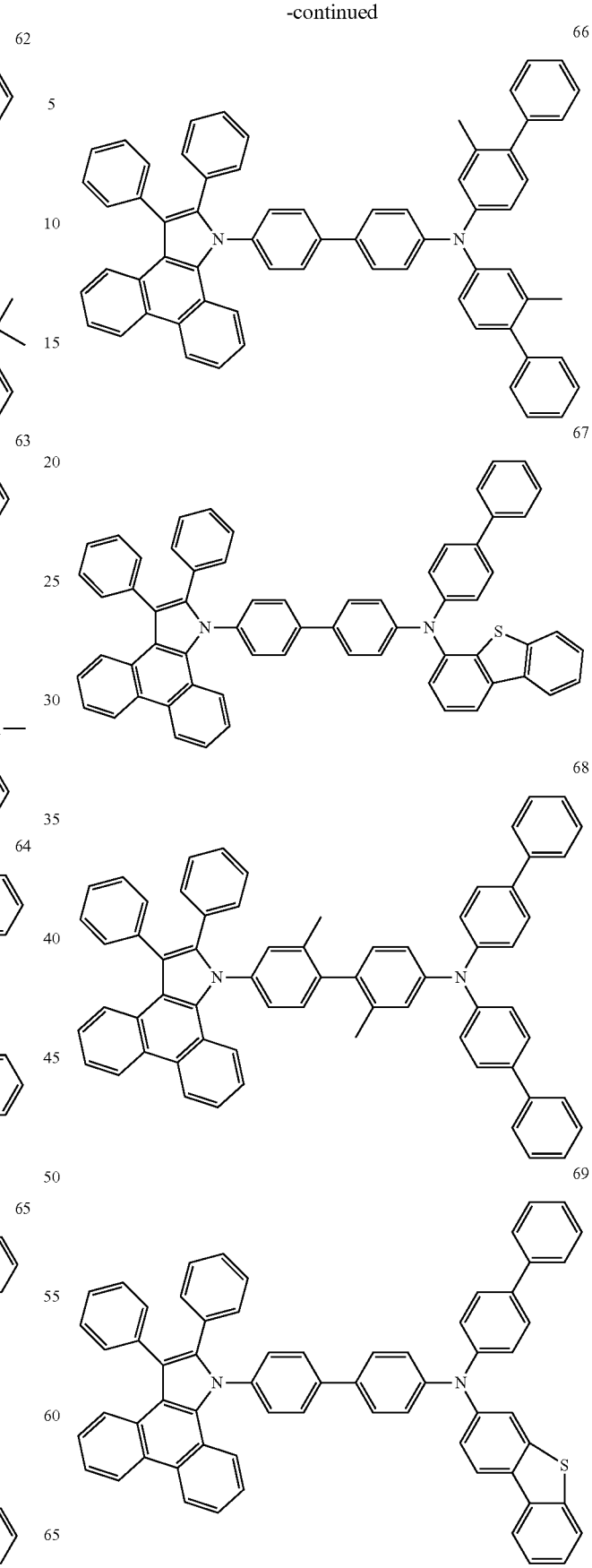

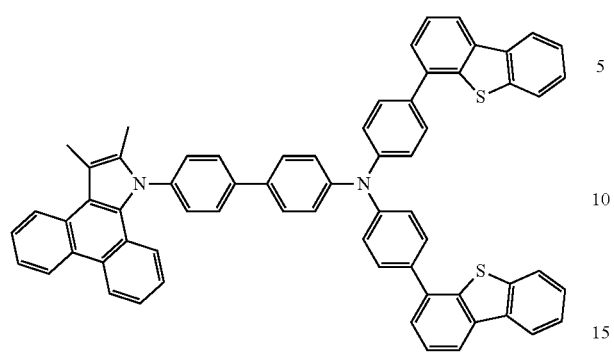
70
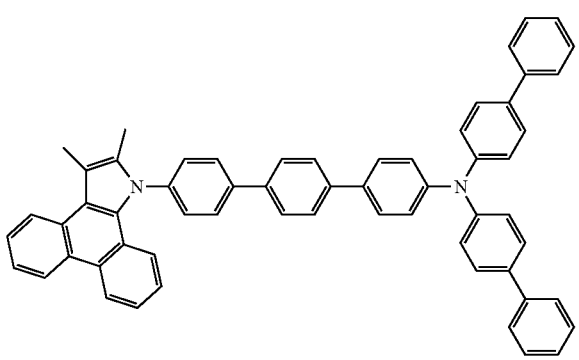
73
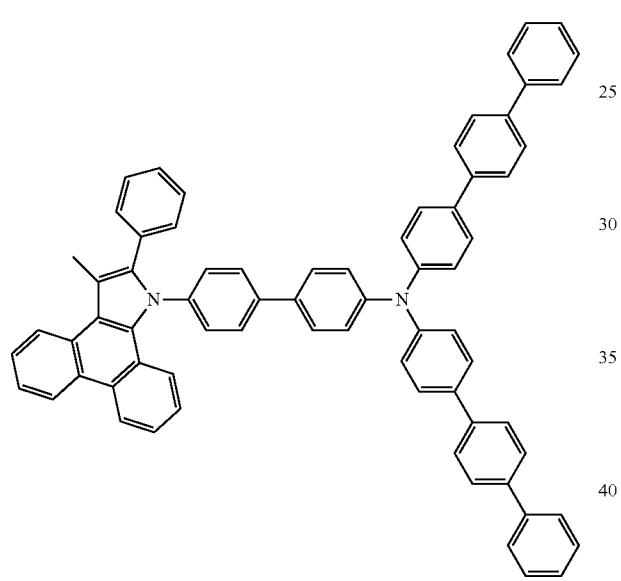
71
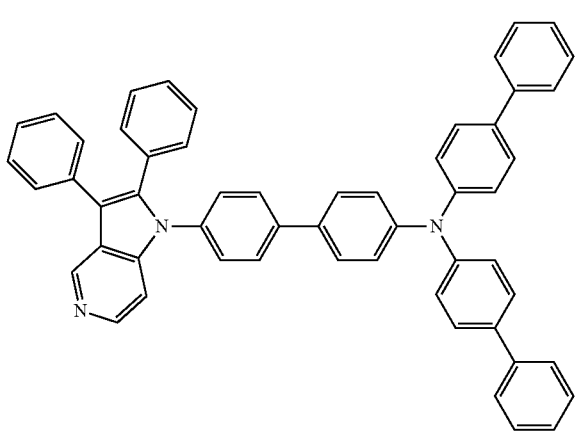
74
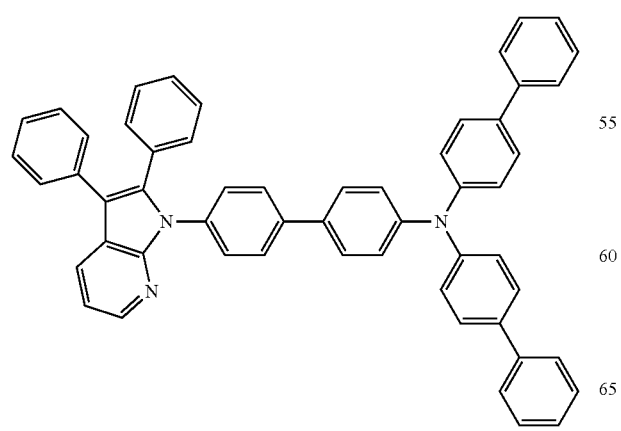
72
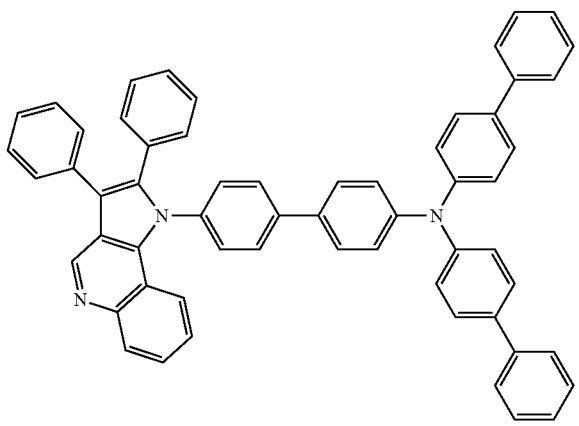
75

76
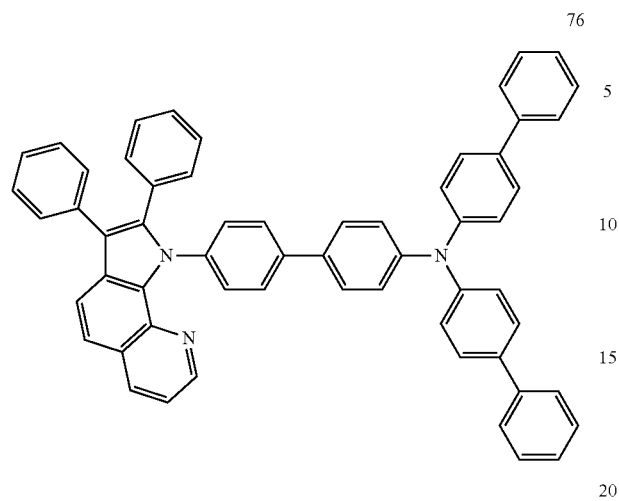
77
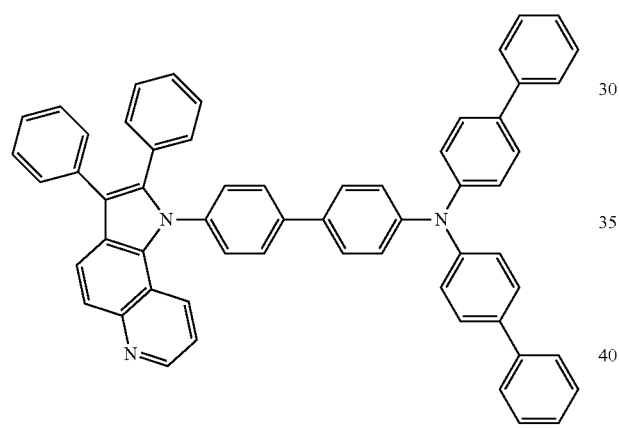
78
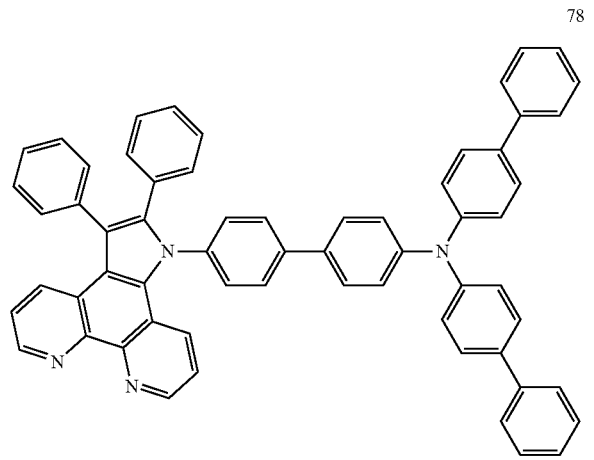
79
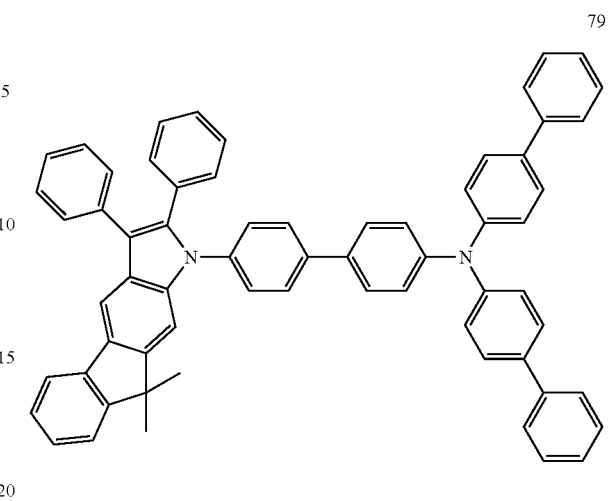
80
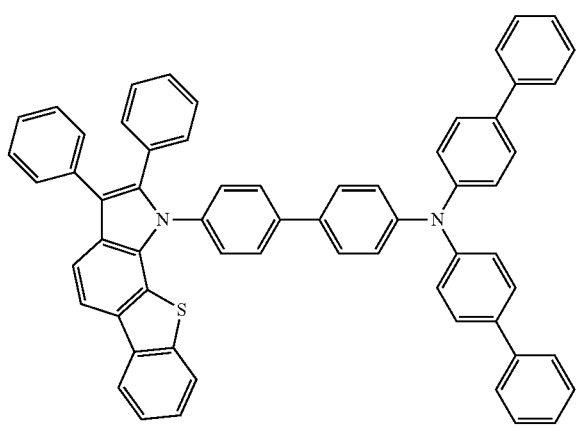
81
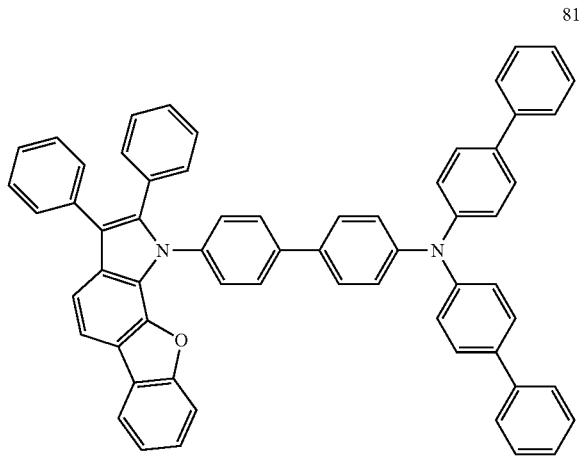

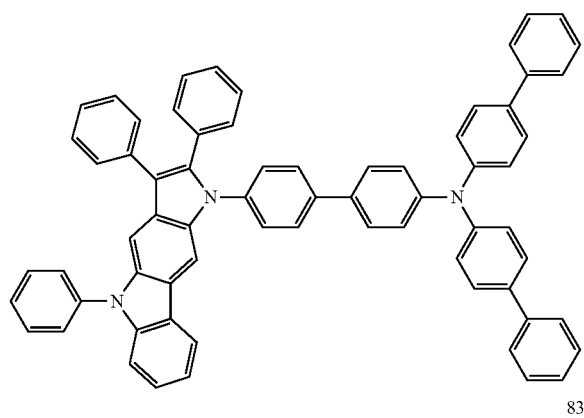

82

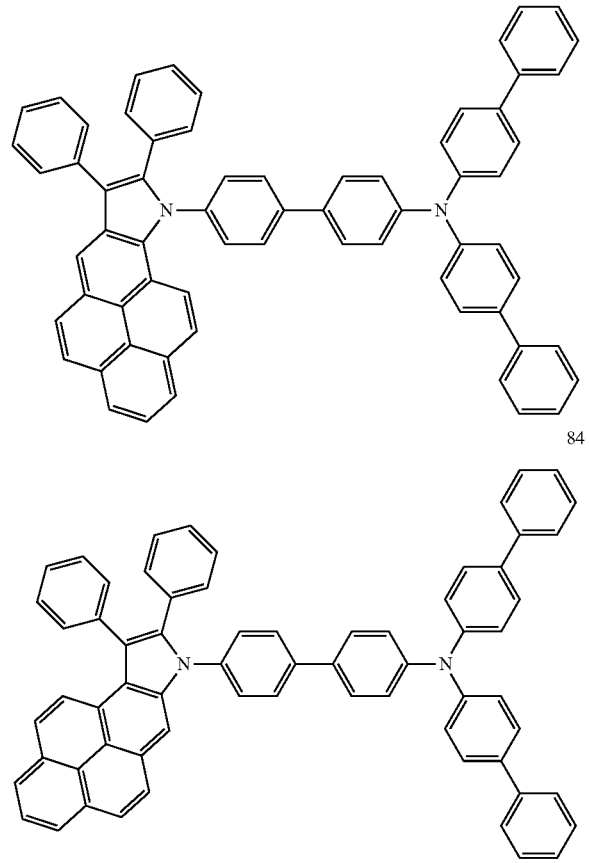

83

84

In another embodiment, at least one substituent of the substituted $C_6$-$C_{60}$ arylene group, the substituted $C_2$-$C_{60}$ heteroarylene group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_2$-$C_{10}$ cycloalkenyl group, the substituted $C_2$-$C_{10}$ heterocycloalkenyl group, the substituted $C_6$-$C_{60}$ aryl group, and the substituted $C_2$-$C_{60}$ heteroaryl group may be selected from:

a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, or a phosphoric acid group or a salt thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethyl fluorenyl group, a diphenyl fluorenyl group, a carbazolyl group, a phenyl carbazolyl group, a pyridyl group, a pyrimidyl group, a pyrazinyl group, a pyridazinyl group, a triazinyl group, a quinolyl group, or an isoquinolyl group; or —Si($Q_{13}$)($Q_{14}$)($Q_{15}$), wherein, $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group; but is not limited thereto.

HOMO energy level of an arylamine-based compound represented by Formula 1 above is relatively low, but higher than that of a host material of an emission layer. Also, triplet energy of the arylamine-based compound having the above Formula 1 is greater than that of the emission material. Accordingly, when the arylamine-based compound represented by Formula 1 above is used as a hole transporting material, a hole transport barrier is lowered to reduce a driving voltage. Also, the arylamine-based compound represented by Formula 1 above has greater energy than that of the emission material, which may prevent diffusion of excitons produced in the emission layer to increase the efficiency of an organic light emitting diode.

The arylamine-based compound represented by Formula 1 above has a structure in which a nitrogen atom of arylamine and a nitrogen atom of a nitrogen-containing heteroaryl group are connected to each other through a linker to have triplet energy greater than that of Compound A. Table 1 below shows results of calculated density functional theory (DFT) of various compounds by using Gaussian 09 (B3LYP/6-31*).

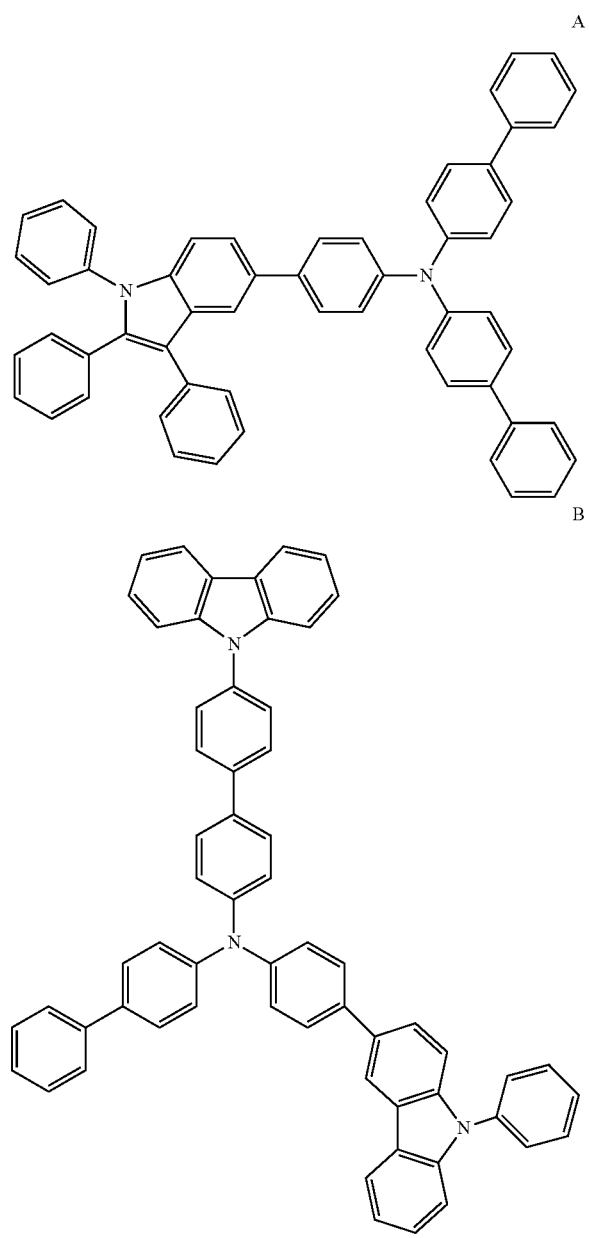 [SMILES: c1ccc(-c2ccc(N(c3ccc(-c4ccccc4)cc3)c3ccc(-c4ccc5c(c4)c(-c4ccccc4)c(-c4ccccc4)n5-c4ccccc4)cc3)cc2)cc1 ; c1ccc(-c2ccc(N(c3ccc(-c4ccc(-n5c6ccccc6c6ccccc65)cc4)cc3)c3ccc(-c4ccc5c(c4)c4ccccc4n5-c4ccccc4)cc3)cc2)cc1]

TABLE 1-continued

| Compound | HOMO (eV) | LUMO (eV) | Ground state energy (eV) | Triplet energy (eV) | Singlet energy (eV) |
|---|---|---|---|---|---|
| 77 | −5.03551 | −1.25718 | 3.77833 | 2.7175 | 3.1059 |
| 80 | −4.96258 | −1.13391 | 3.82867 | 2.6696 | 3.3374 |
| 81 | −4.91904 | −1.11649 | 3.80255 | 2.693 | 3.3237 |

Referring to Table 1 above, calculated triplet energy of Compound 16 is greater than calculated triplet energy of Compound A. Accordingly, the organic light emitting diode including an arylamine-based compound represented by Formula 1 above has better efficiency and lifespan characteristics than an organic light emitting diode including Compound A as a hole transporting layer.

Furthermore, referring to Table 1 above, substituents of an arylamine-based compound represented by Formula 1 above may be variously adjusted to variously adjust the magnitude of triplet energy. In more detail, substituents such as a methyl group or a phenyl group in a nitrogen-containing heteroaromatic ring of the arylamine-based compound having the Formula 1 above may be further substituted to suitably adjust HOMO and LUMO values. As a result, hole injection characteristic and mobility of the arylamine-based compound represented by Formula 1 above may be finely adjusted. Also, triplet energy level of the arylamine-based compound having the Formula 1 above may be adjusted to prevent diffusion of excitons produced in the emission layer (into other layers). Accordingly, an organic light emitting diode comprising the arylamine-based compound represented by Formula 1 above has improved efficiency and longer lifespan through a hole-electron balance.

The arylamine-based compound represented by Formula 1 above may be synthesized by using a suitable organic synthesis method. A method of synthesizing the arylamine-based compound represented by Formula 1 above may be inferred based on the Examples described below.

One or more of the arylamine-based compounds represented by Formula 1 above may be used to form an organic layer between a pair of electrodes in an organic light emitting diode. For example, one or more of the arylamine-based compounds represented by Formula 1 above may be used in a hole transporting layer.

Accordingly, provided is an organic light emitting diode including a first electrode; a second electrode disposed opposite to the first electrode; and an organic layer disposed between the first electrode and the second electrode, wherein the organic layer includes one or more of the arylamine-based compounds represented by Formula 1 above.

As used herein, the expression "(organic layer) includes one or more of the arylamine-based compounds represented by Formula 1 above" may be construed as "(organic layer) may include one arylamine-based compounds of Formula 1 or two or more of different arylamine-based compounds of Formula 1".

For example, the organic layer is an arylamine-based compound and may only include Compound 1. Here, Compound 1 may exist in the hole transporting layer of the organic light emitting diode. In another embodiment, the organic layer is the arylamine-based compound and may include Compound 1 and Compound 2. Here, Compound 1 and Compound 2 may exist in the same layer or different layers (for example, a hole transporting layer or a first hole transporting layer and a second hole transporting layer). In

TABLE 1

| Compound | HOMO (eV) | LUMO (eV) | Ground state energy (eV) | Triplet energy (eV) | Singlet energy (eV) |
|---|---|---|---|---|---|
| ADN | −5.097 | −1.63977 | 3.45723 | 1.6901 | 3.3925 |
| NPB | −4.70706 | −1.14833 | 3.55873 | 2.438 | 3.0395 |
| 2-TNATA | −4.39114 | −1.04656 | 3.34458 | 2.4428 | 2.7754 |
| A | −4.71659 | −0.90207 | 3.814525 | 2.6981 | 3.2524 |
| B | −4.82217 | −1.07377 | 3.7484 | 2.6618 | 3.1657 |
| 10 | −4.97428 | −1.15677 | 3.81751 | 2.7389 | 3.0588 |
| 16 | −4.92312 | −1.10234 | 3.82078 | 2.6976 | 3.3331 |
| 40 | −4.9351 | −1.04084 | 3.89426 | 2.7547 | 3.4038 |
| 51 | −4.93891 | −1.12139 | 3.81752 | 2.7244 | 3.0922 |
| 53 | −4.95414 | −0.95894 | 3.995203 | 2.7239 | 3.0796 |
| 56 | −4.9887 | −1.19459 | 3.79411 | 2.6861 | 3.1673 |
| 68 | −4.9585 | −0.91676 | 4.041741 | 2.7249 | 3.2464 |
| 69 | −5.00693 | −1.23677 | 3.77016 | 2.6638 | 3.2213 |
| 74 | −5.00585 | −1.22398 | 3.78187 | 2.6882 | 3.31 | more detail, Compound 1 may exist in the first hole transporting layer and Compound 2 may exist in the second hole transporting layer.

The organic layer may include at least one layer selected from: a hole injecting layer, a hole transporting layer, a functional layer having both hole injecting and hole transporting capabilities (hereinafter, "H-functional layer"), a buffer layer, or an electron blocking layer between the first electrode and the emission layer, and includes at least one layer selected from: a hole blocking layer, a hole transporting layer, or an electron injecting layer between the emission layer and the second electrode. A region including the at least one layer selected from: a hole injecting layer, a hole transporting layer, a functional layer having both hole injecting and hole transporting capabilities (hereinafter, "H-functional layer"), a buffer layer, or an electron blocking layer is referred to as a hole transporting region. The organic layer may further include an electron transporting region between the emission layer and the second electrode. The electron transporting region may include at least one of a hole blocking layer, an electron transporting layer, or an electron injecting layer As used herein, the "organic layer" refers to a single layer and/or a plurality of layers disposed between the first electrode and the second electrode.

One or more of the arylamine-based compounds may be included in the hole transporting region. The organic layer includes a hole transporting layer between the first electrode and the emission layer and one or more of the arylamine-based compounds represented by Formula 1 above may be included in the hole transporting layer.

In another embodiment, the organic layer includes a first hole transporting layer and a second hole transporting layer between the first electrode and the emission layer, wherein the second hole transporting layer is disposed between the first hole transporting layer and the emission layer, and the second hole transporting layer may include one or more of the arylamine-based compounds represented by Formula 1 above.

In another embodiment, the organic layer includes a first hole transporting layer and a second hole transporting layer between the first electrode and the emission layer, wherein the second hole transporting layer is disposed between the first hole transporting layer and the emission layer, and each of the first hole transporting layer and the second hole transporting layer includes one or more of the arylamine-based compounds represented by Formula 1 above, and the arylamine-compound included in the first hole transporting layer and the arylamine-based compound included in the second hole transporting layer may be different.

FIG. 1 is a schematic view of a structure of an organic light emitting diode 100 according to an embodiment of the present invention. Hereinafter, structure and a method of manufacturing the organic light emitting diode according to an embodiment of the present invention will be described with reference to FIG. 1.

The substrate 110 may be any substrate that is used in conventional organic light emitting diodes such as a glass substrate or a transparent plastic substrate having strong mechanical strength, thermal stability, transparency, surface smoothness, ease of handling, and water resistance.

The first electrode 120 may be formed on the substrate by depositing or sputtering a first electrode-forming material onto a surface of the substrate 110. When the first electrode 120 is an anode, a material having a high work function may be used as the first electrode-forming material to facilitate hole injection. The first electrode 120 may be a reflective electrode or a transmission electrode. Materials having excellent transparent and conductive capabilities such as indium tin oxide (ITO), indium zinc oxide (IZO), tin oxide ($SnO_2$), or zinc oxide (ZnO) may be used to form the first electrode 120. In other embodiments, magnesium (Mg), aluminum (Al), aluminum-lithium (Al—Li), calcium (Ca), magnesium-indium (Mg—In), magnesium-silver (Mg—Ag), or the like may be used to form the first electrode 120 as a reflective electrode.

The first electrode 120 may have a single layer or a multi-layer structure including two or more layers. For example, the first electrode 120 may have a three-layered structure of ITO/Ag/ITO, but is not limited thereto.

An organic layer 130 is disposed on the first electrode 120.

The organic layer 130 may include a hole injecting layer 131, a hole transporting layer 132, an H-functional layer, a buffer layer, an emission layer 133, an electron transporting layer 134, and an electron injecting layer 135.

The hole injecting layer (HIL) 131 may be formed on the first electrode 120 using vacuum deposition, spin coating, casting, Langmuir-Blodgett (LB) deposition, or the like.

When the HIL 131 is formed using vacuum deposition, vacuum deposition conditions may vary according to the compound that is used to form the HIL 131, and the desired structure and thermal properties of the HIL 131 to be formed. For example, vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL 131 is formed using spin coating, the coating conditions may vary according to the compound that is used to form the HIL 131, and the desired structure and thermal properties of the HIL 131 to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL 131 may be formed of any suitable hole injecting material, and non-limiting examples of suitable hole injecting material are N,N'-diphenyl-N,N'-bis-[4-(phenyl-m-tolylamino)-phenyl]-biphenyl-4,4'-diamine, (DNTPD), a phthalocyanine compound such as copper phthalocyanine, 4,4',4"-tris(3-methylphenylphenylamino)triphenylamine (m-MTDATA), N,N'-di(1-naphthyl-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS).

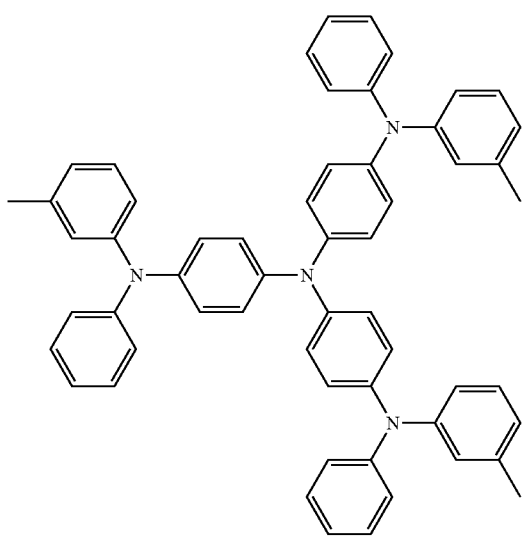

m-MTDATA

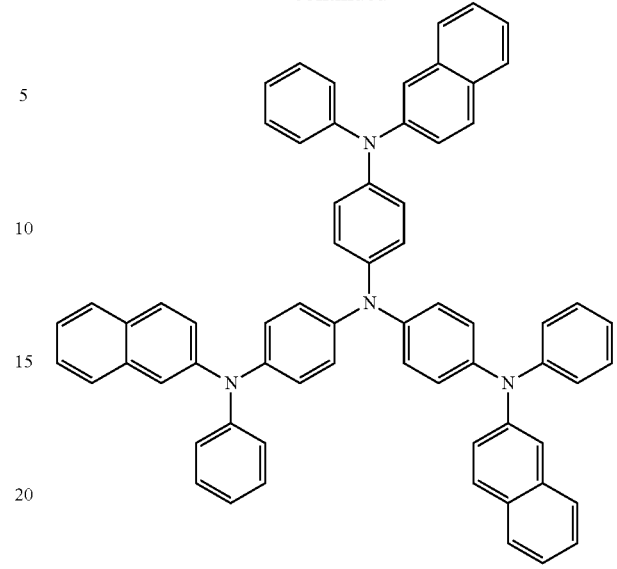

2-TNATA

The thickness of the HIL 131 may be from about 100 Å to about 10000 Å, and in some embodiments, may be from about 100 Å to about 1000 Å. In one embodiment, when the thickness of the HIL 131 is within these ranges, the HIL 131 has good hole injecting ability without a substantial increase in driving voltage.

The HIL 131 may further include a charge-generating material in addition to the above described hole injecting material to improve conductivity of the hole injecting layer. Non-limiting examples of suitable charge-generating material are quinone derivatives such as tetracyanoquinonedimethane (TCNQ), 2,3,5,6-tetrafluoro-tetracyano-1,4-benzoquinonedimethane (F4-TCNQ), or the like; metal oxides such as tungsten oxide, molybdenum oxide, or the like; and cyano-containing compounds such as Compound 100 below.

Compound 100

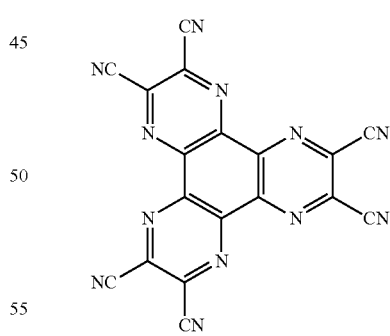

When the HIL 131 further includes a charge-generating material, the charge-generating material may be homogeneously dispersed or inhomogeneously distributed in the HIL 131.

Then, a hole transporting layer (HTL) 132 may be formed on the HIL 131 by using various methods such as vacuum deposition, spin coating, casting, or LB deposition. When the HTL 132 is formed using vacuum deposition or spin coating, the deposition and coating conditions may be similar to those for the formation of the HIL 131, though the

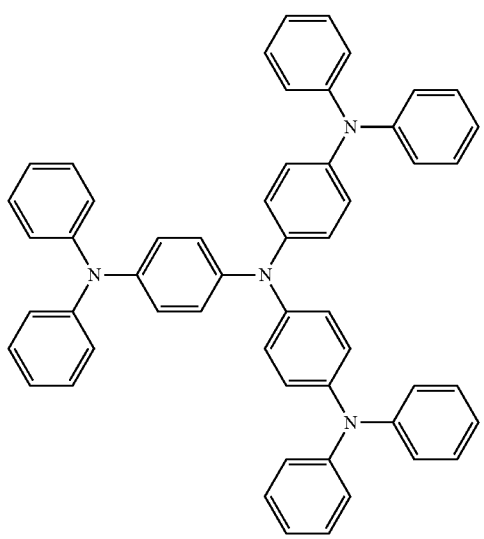

TDATA conditions for deposition and coating may vary according to the material that is used to form the HTL 132.

The HTL 132 may include at least one of the arylamine-based compounds represented by Formula 1.

The HTL 132 may further include a suitable hole transporting material in addition to the arylamine-based compound represented by Formula 1.

A suitable hole transporting material may be used as the hole transporting material, and non-limiting examples of the suitable hole transporting material include carbazole derivatives such as N-phenylcarbazole orpolyvinylcarbazole, N,N'-bis(3-methyl phenyl)-N,N'-diphenyl-[1,1-biphenyl]-4,4'-diamine (TPD), 4,4',4"-tris(N-carbazolyl)triphenylamine (TCTA), and N,N'-di(1-naphthyl-N,N'-diphenylbenzidine) (NPB).

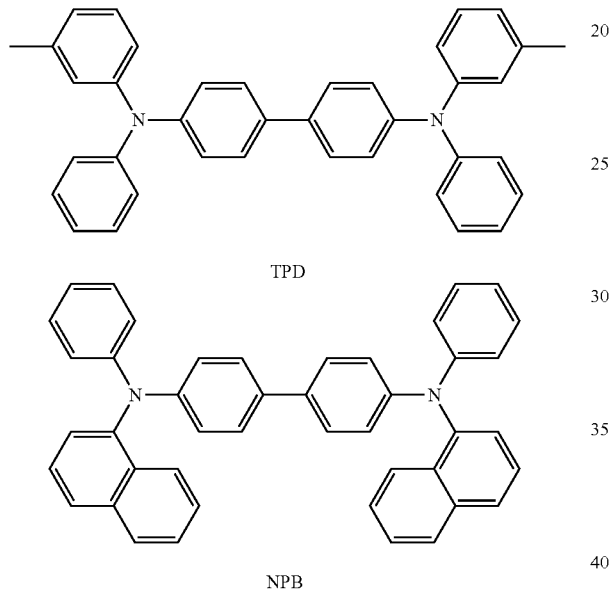

The thickness of the HTL 132 may be from about 50 Å to about 2000 Å, and in some embodiments, may be from about 100 Å to about 1500 Å. In one embodiment, when the thickness of the HTL 132 is within these ranges, the HTL 132 has good hole transporting ability without a substantial increase in driving voltage.

The H-functional layer (having both hole injecting and hole transporting capabilities) may contain at least one material from each group of the hole injecting layer materials and hole transporting layer materials. The thickness of the H-functional layer may be from about 500 Å to about 10,000 Å, and in some embodiments, may be from about 100 Å to about 1,000 Å. In one embodiment, when the thickness of the H-functional layer is within these ranges, the H-functional layer has good hole injecting and transporting abilities without a substantial increase in driving voltage.

In some embodiments, at least one of the HIL 131, HTL 132, and H-functional layer may include at least one compound of Formula 300 below and a compound of Formula 350 below:

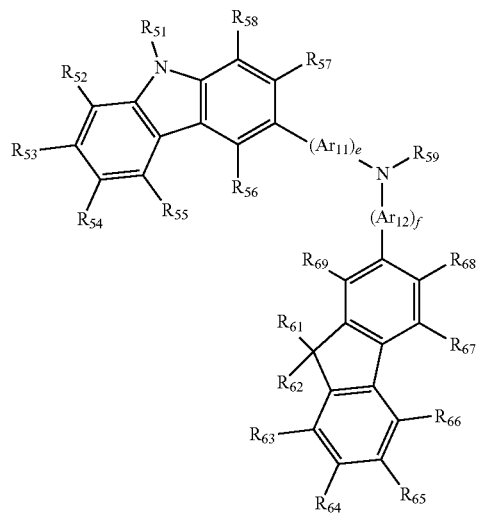

Formula 300

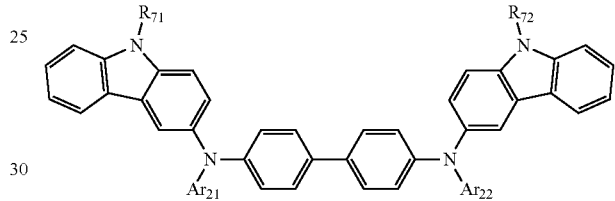

Formula 350

In Formulae 300 and 350 above, each of $Ar_{11}$, $Ar_{12}$, $Ar_{21}$, and $Ar_{22}$ is independently a substituted or unsubstituted $C_5$-$C_{60}$ arylene group. Detailed descriptions of the groups represented by $Ar_{11}$, $Ar_{12}$, $Ar_{21}$, and $Ar_{22}$ are referred to (the same as) in the detailed description of the group represented by X above.

In Formula 300, e and f are each independently an integer of 0 to 5, or 0, 1, or 2. For example, e may be 1 and f may be 0, but are not limited thereto.

In Formulae 300 and 350, each of $R_{51}$ to $R_{58}$, $R_{61}$ to $R_{69}$, $R_{71}$ and $R_{72}$ may be independently a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group.

For example, the groups represented by $R_{51}$ to $R_{58}$, $R_{61}$ to $R_{69}$, $R_{71}$ and $R_{72}$ may be each independently one of: a hydrogen atom; a deuterium atom; a halogen atom; a hydroxyl group; a cyano group; a nitro group; an amino group; an amidino group; a hydrazine group; a hydrazone group; a carboxylic acid group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, and a hexyl group); a $C_1$-$C_{10}$ alkoxy group (for example, a methoxy group, an ethoxy group, a propoxy group, a butoxy group, and a pentoxy group); a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; a phenyl group; a naphthyl group; an anthryl group; a fluorenyl group; a pyrenyl group; a phenyl group, a naphthyl group, an anthryl group, a fluorenyl group, and a pyrenyl group, each substituted with a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but is not limited thereto.

In Formula 300, a group represented by $R_{59}$ may be any one of: a phenyl group; a naphthyl group; an anthryl group; a biphenyl group; a pyridyl group; and a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment, the compound represented by Formula 300 may be represented by Formula 300A below, but is not limited thereto:

Formula 300A

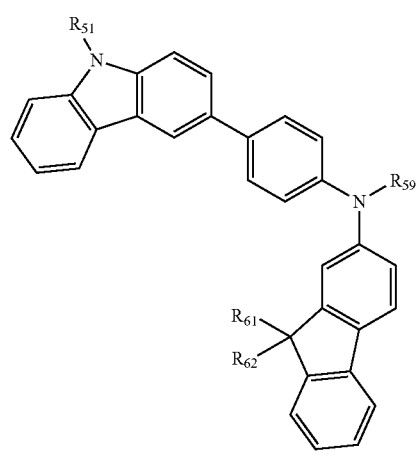

In Formula 300A, detailed descriptions of groups represented by $R_{51}$, $R_{61}$, $R_{62}$, and $R_{59}$ are referred to (the same as) the description of respective groups regarding Formulae 300 and 350 above.

For example, at least one layer of the HIL 131, HTL 132, and H-functional layer may include one or more of Compounds 301 to 320 below, but is not limited thereto:

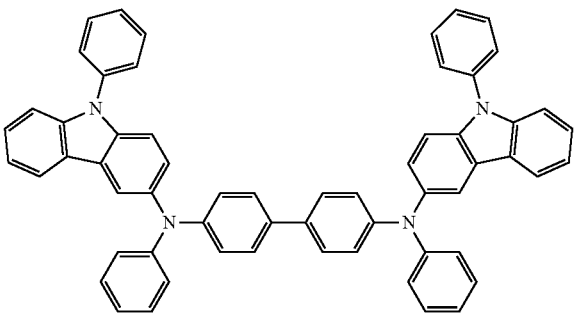

301

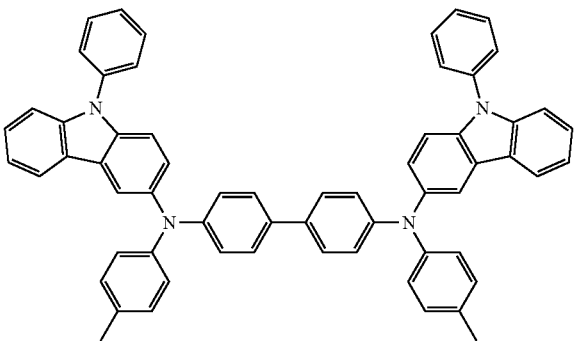

302

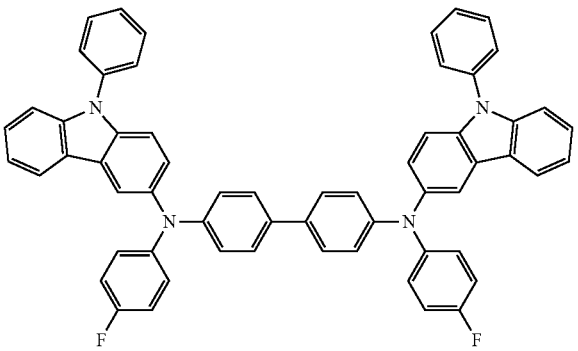

303

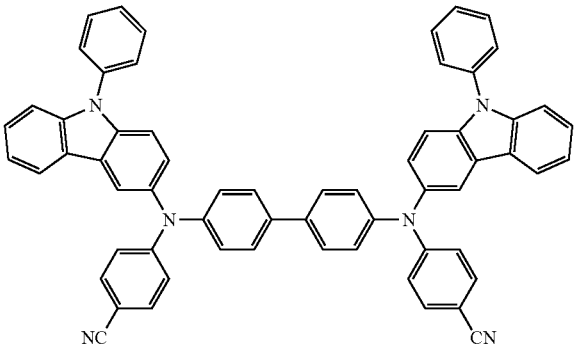

304

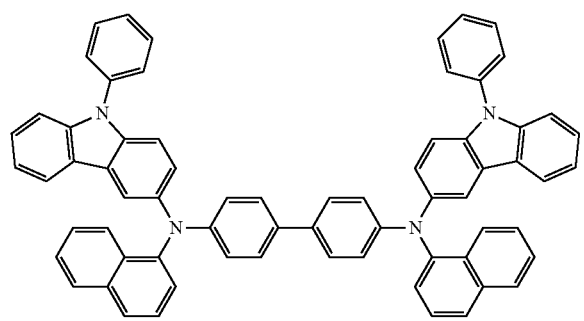
305
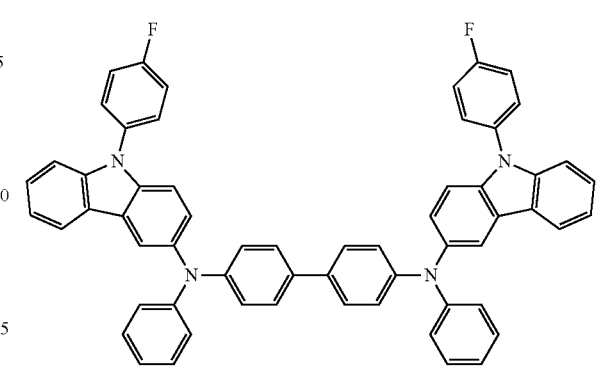
308
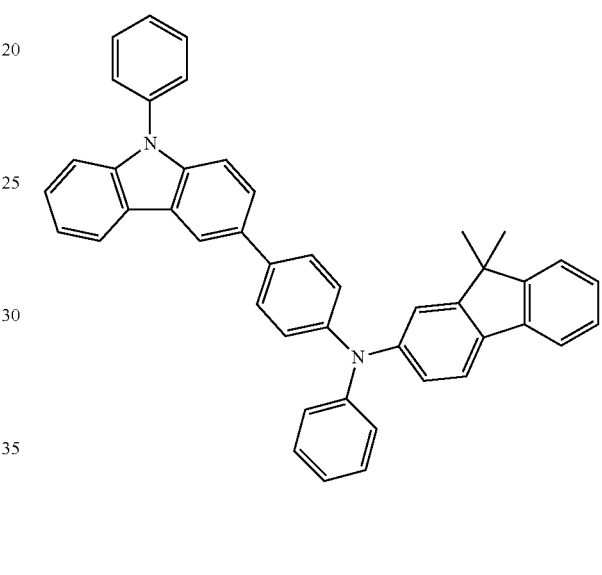
309
306
307
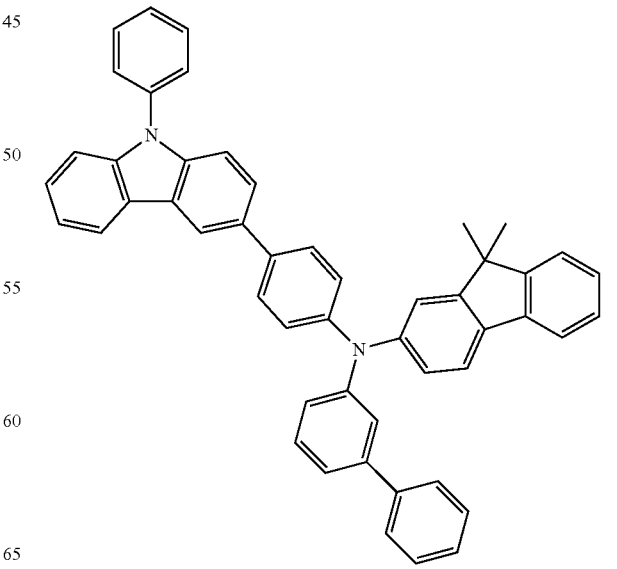
310

311
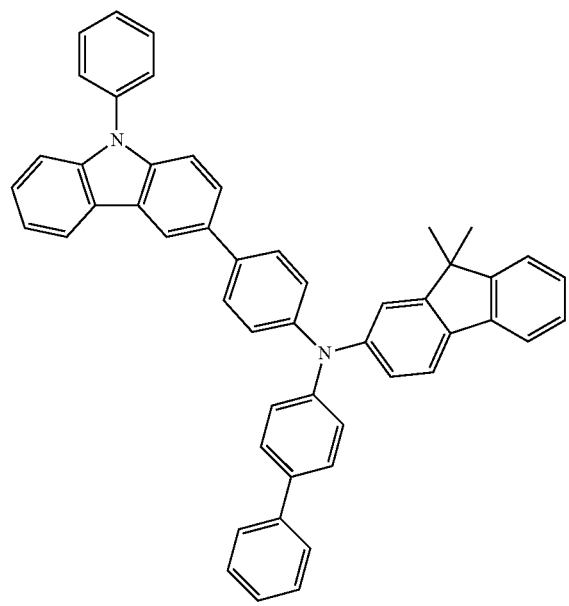
313
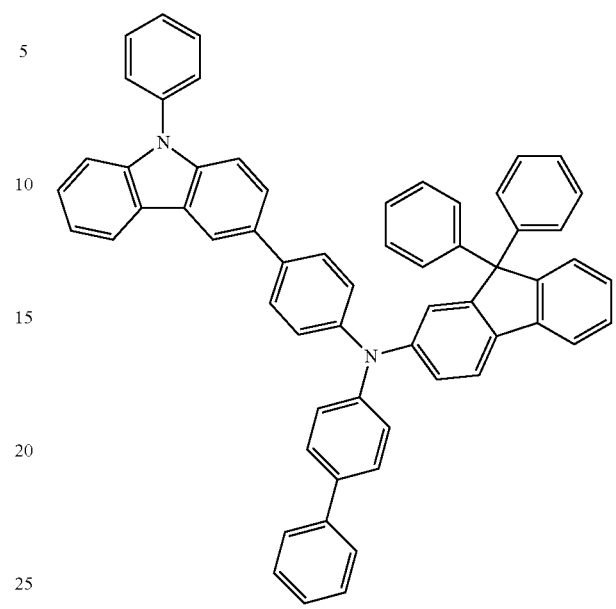
312
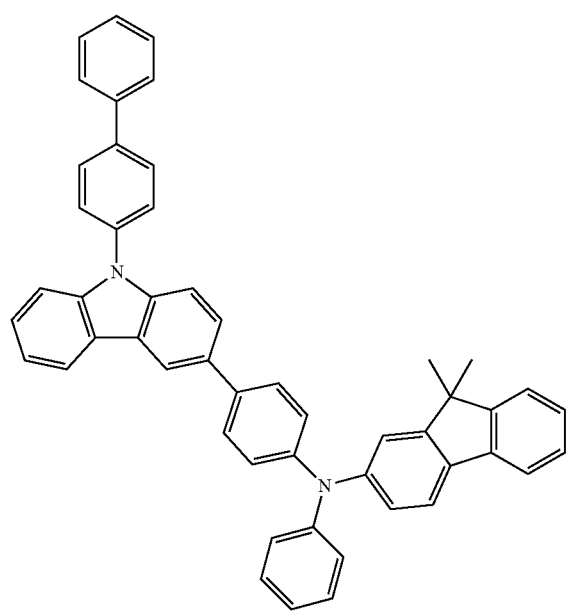
314
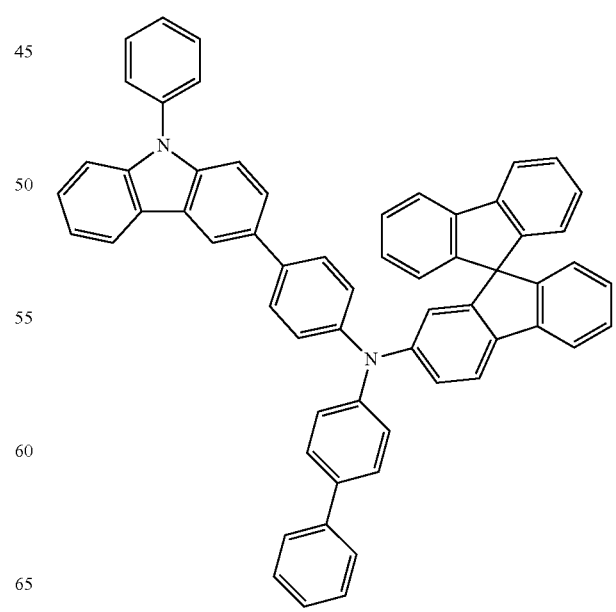

315
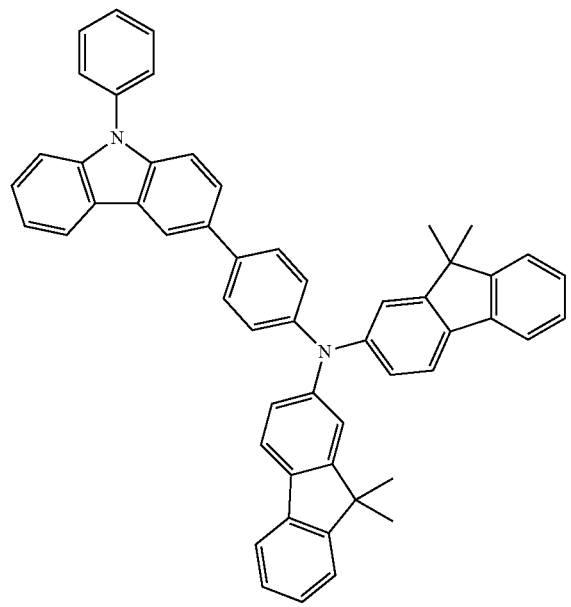
316
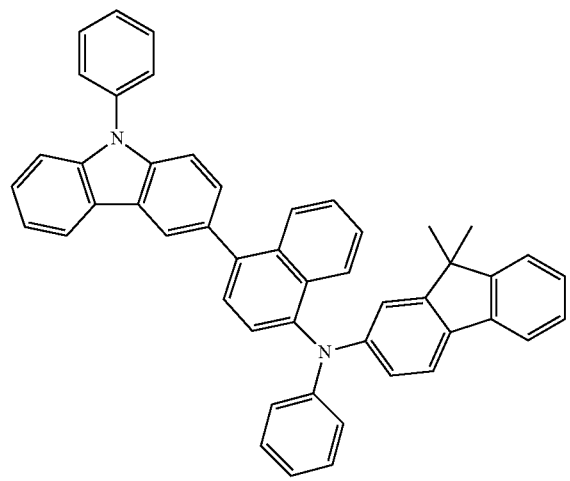
317
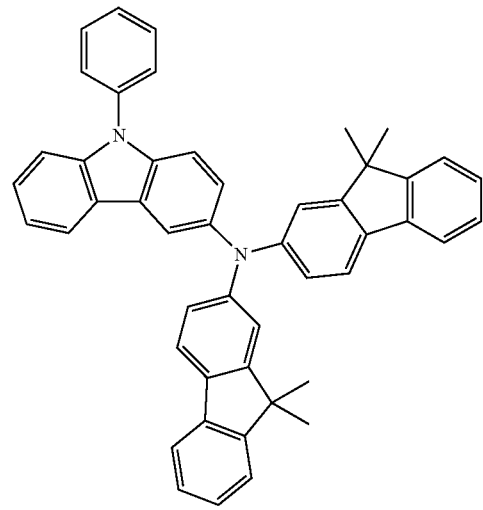
318
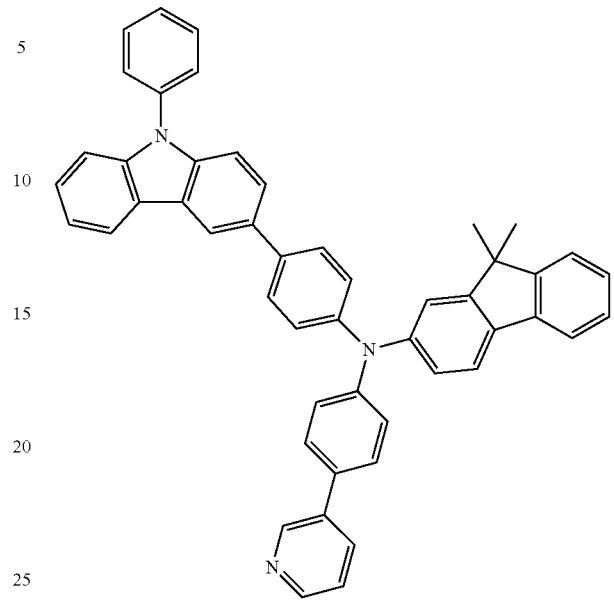
319
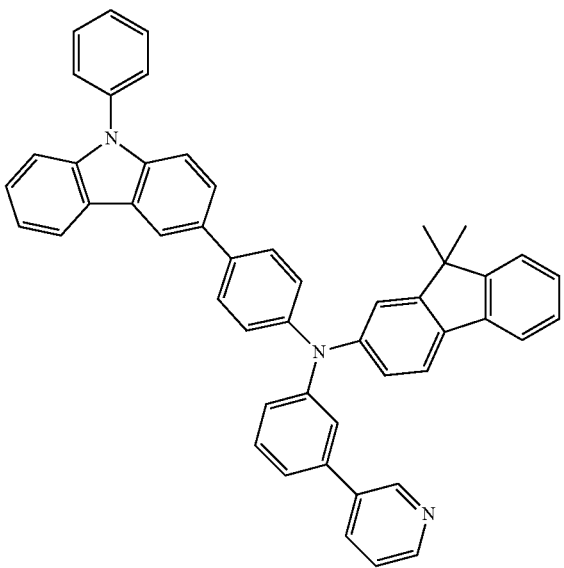

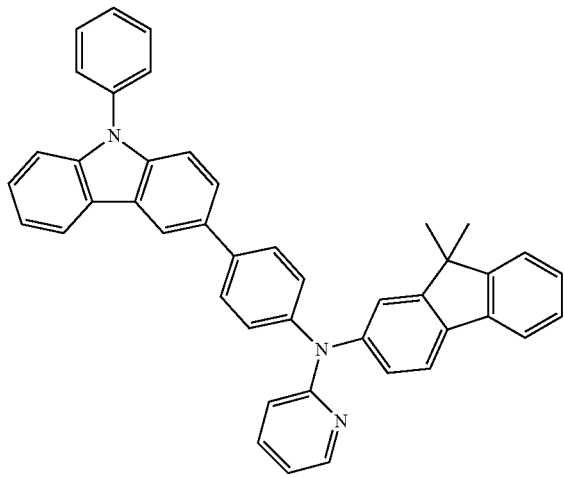

320

At least one of the HIL 131, HTL 132, and the H-functional layer may further include a charge-generating material for improved layer conductivity, in addition to a suitable hole injecting material, hole transporting material, and/or material having both hole injecting and hole transporting capabilities as described above.

The charge-generating material may be, for example, one of quinone derivatives, metal oxides, or cyano group containing compounds, but are not limited thereto. Non-limiting examples of the p-dopant are quinone derivatives such as tetracyanoquinonedimethane (TCNQ) or 2,3,5,6-tetrafluoro-tetracyano-1,4-benzoquinonedimethane (F4-TCNQ); metal oxides such as tungsten oxide or molybdenum oxide; and cyano group containing compounds such as Compound 200 below.

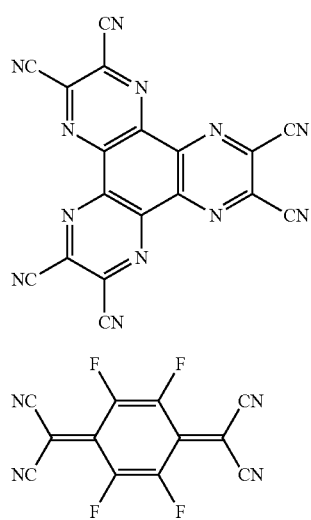

Compound 200

F4-TCNQ

When the HIL 131, HTL 132, or H-functional layer further includes a charge-generating material, the charge-generating material may be homogeneously dispersed or inhomogeneously distributed in the HIL 131, HTL 132, or H-functional layer.

A buffer layer may be disposed between at least one of the HIL 131, HTL 132, and H-functional layer, and the EML.

The buffer layer may compensate for an optical resonance distance of light according to a wavelength of the light emitted from the EML, and thus may increase efficiency. The buffer layer may include any hole injecting material or hole transporting material that are suitable. In some other embodiments, the buffer layer may include the same material as one of the materials included in the HIL 131, HTL 132, and H-functional layer that underlie the buffer layer.

Then, an emission layer (EML) 133 may be formed on the HTL 132, H-functional layer, or buffer layer by vacuum deposition, spin coating, casting, Langmuir-Blodget (LB) deposition, or the like. When the EML 133 is formed using vacuum deposition or spin coating, the deposition and coating conditions may be similar to those for the formation of the HIL 131, though the conditions for deposition and coating may vary according to the material that is used to form the EML 133.

The EML 133 may include a suitable light-emitting material. For example, the EML 133 may include a suitable host and a dopant.

Non-limiting examples of suitable host include $Alq_3$, 4,4'-N,N'-dicarbazole-biphenyl (CBP), poly(n-vinylcarbazole) (PVK), 9,10-di(naphthalene-2-yl)anthracene (DNA), TCTA, 1,3,5-tris(N-phenylbenzimidazole-2-yl)benzene (TPBI), 3-tertert-butyl-9,10-di(napth-2-yl)anthracene (TBADN), mCP, and OXD-7, but the host is not limited thereto.

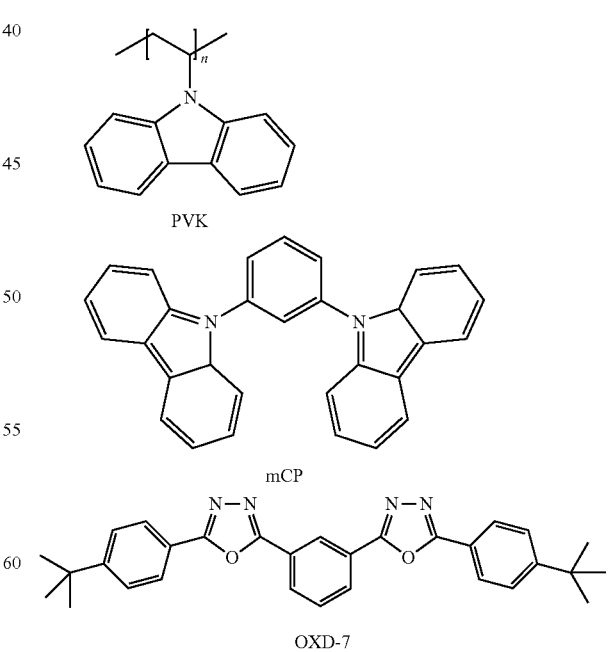

PVK mCP

OXD-7

In another embodiment, an anthracene-based compound represented by Formula 400 below may be used as the host:

Formula 400

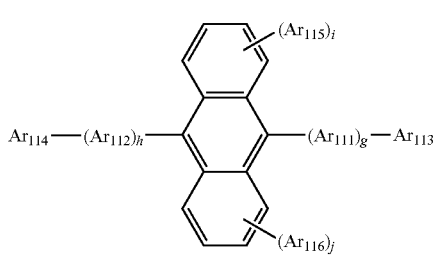

In Formula 400, each of Ar$_{111}$ and Ar$_{112}$ is independently a substituted or unsubstituted C$_5$-C$_{60}$ arylene group; each of Ar$_{113}$ to Ar$_{116}$ is independently a substituted or unsubstituted C$_1$-C$_{10}$ alkyl group or a substituted or unsubstituted C$_5$-C$_{60}$ aryl group; and g, h, i, and j are each independently an integer of 0 to 4.

For example, in Formula 400, each of Ar$_{111}$ and Ar$_{112}$ may be:
 a phenylene group, a naphthylene group, a phenanthrenylene group, or a pyrenylene group; or
 a phenylene group, a naphthylene group, a phenanthrenylene group, a fluorenyl group, or a pyrenylene group, each substituted with one or more of a phenyl group, a naphthyl group, or an anthryl group, but are not limited thereto.

In Formula 400 above, g, h, i, and j are each independently an integer of 0, 1, or 2.

In Formula 400, each of Ar$_{113}$ to Ar$_{116}$ is independently a C$_1$-C$_{10}$ alkyl group substituted with one or more of a phenyl group, a naphthyl group, or an anthryl group; a phenyl group; a naphthyl group; an anthryl group; a pyrenyl group; a phenanthrenyl group; or a fluorenyl group; a phenyl group, a naphthyl group, an anthryl group, a pyrenyl group, a phenanthrenyl group, or a fluorenyl group, each substituted with one or more of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a phenyl group, a naphthyl group, an anthryl group, a pyrenyl group, a phenanthrenyl group, or a fluorenyl group; and

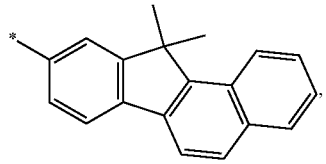 [SMILES: *c1ccc2c(c1)C(C)(C)c1c-2ccc2ccccc12]

but are not limited thereto.

For example, the anthracene-based compound represented by Formula 400 above may be one of the following compounds, but is not limited thereto:

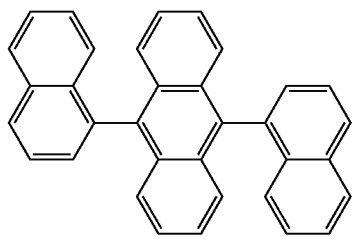

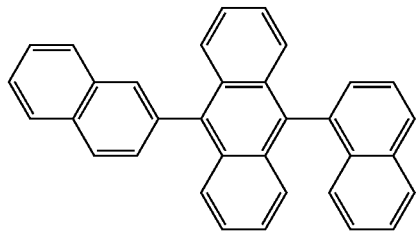

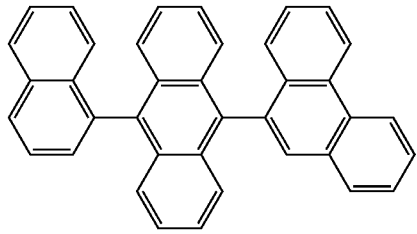

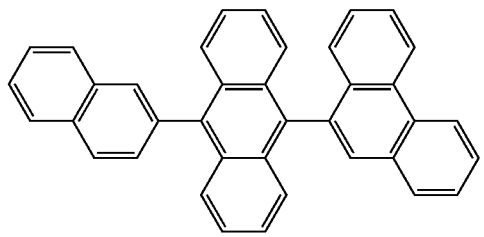

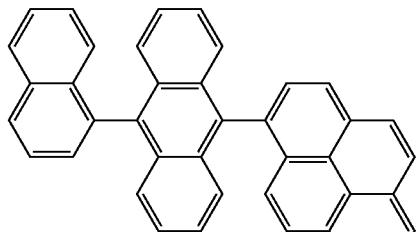

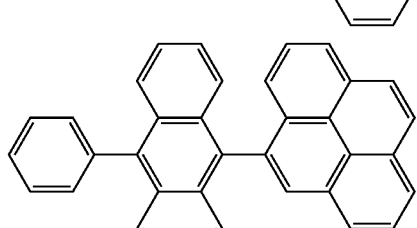

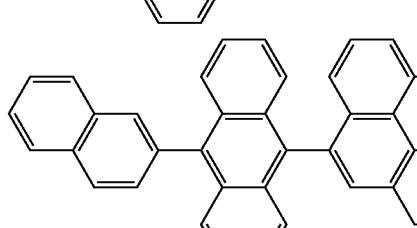

-continued
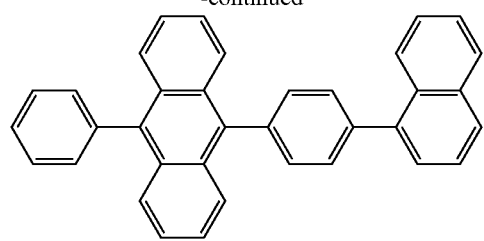
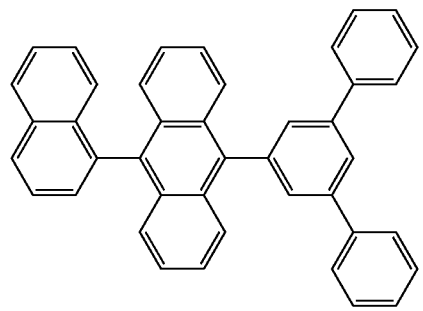
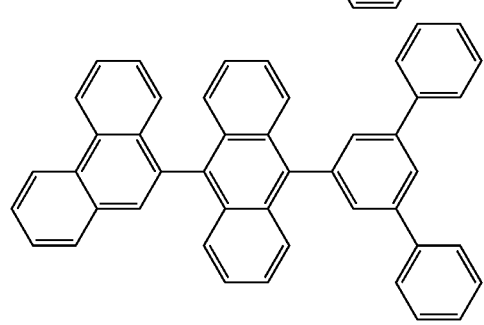
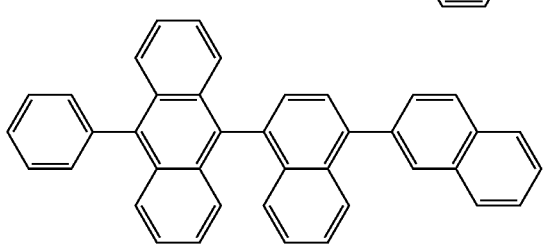
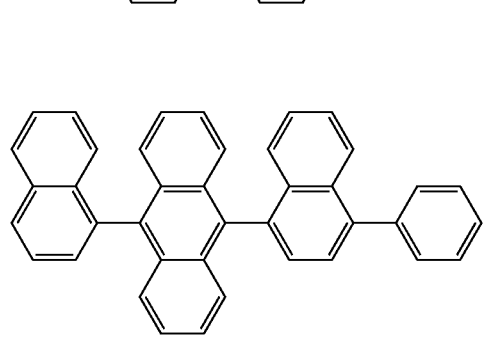
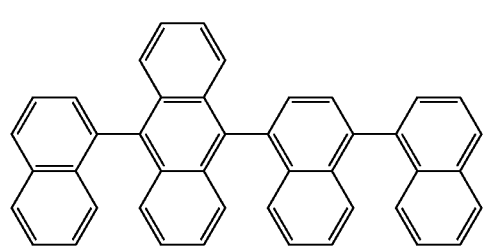
-continued
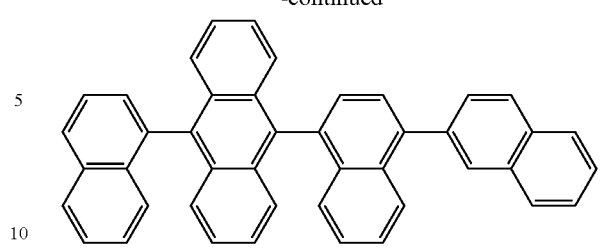
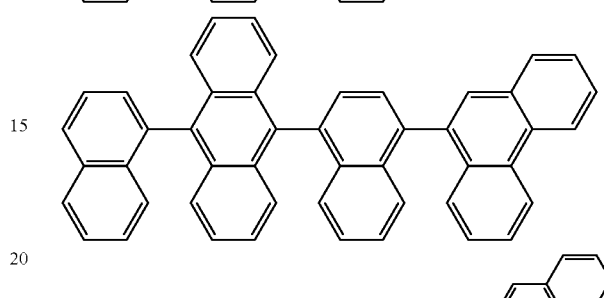
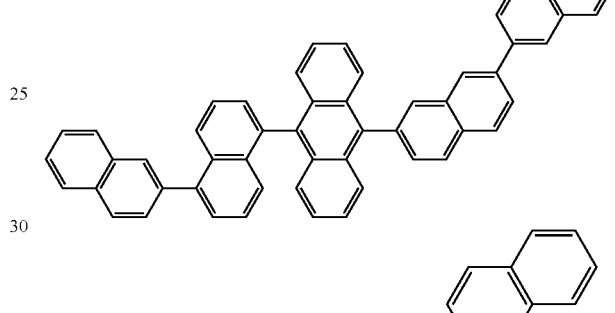
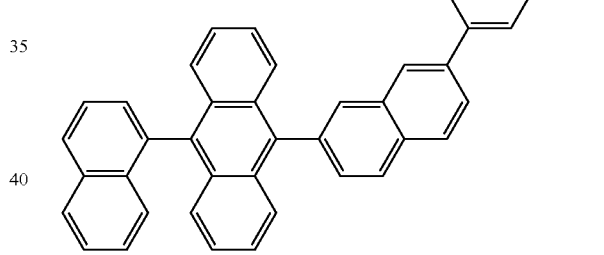
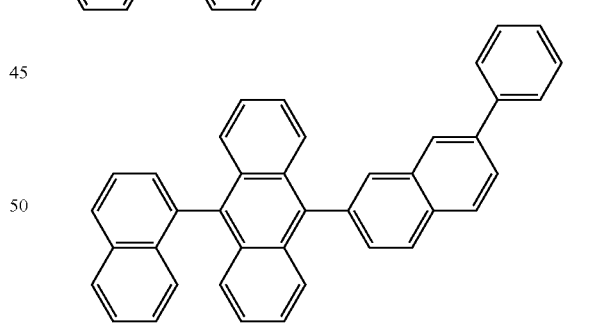
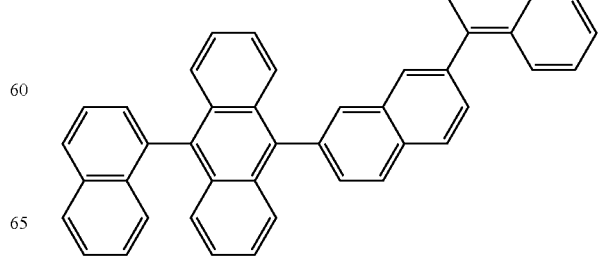

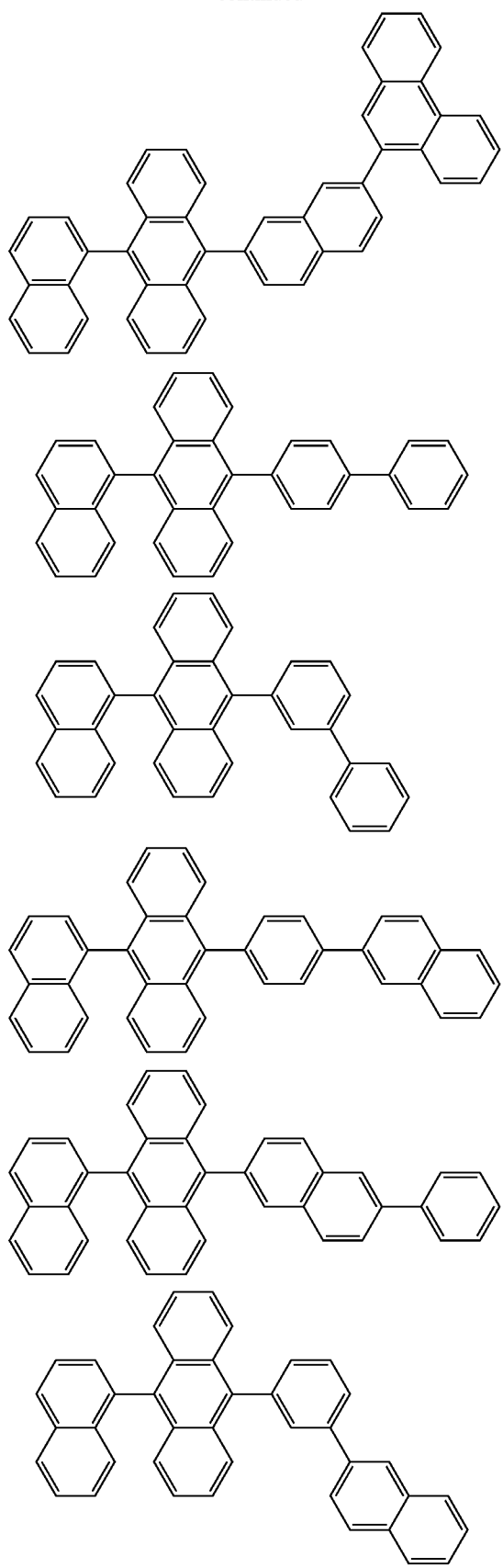
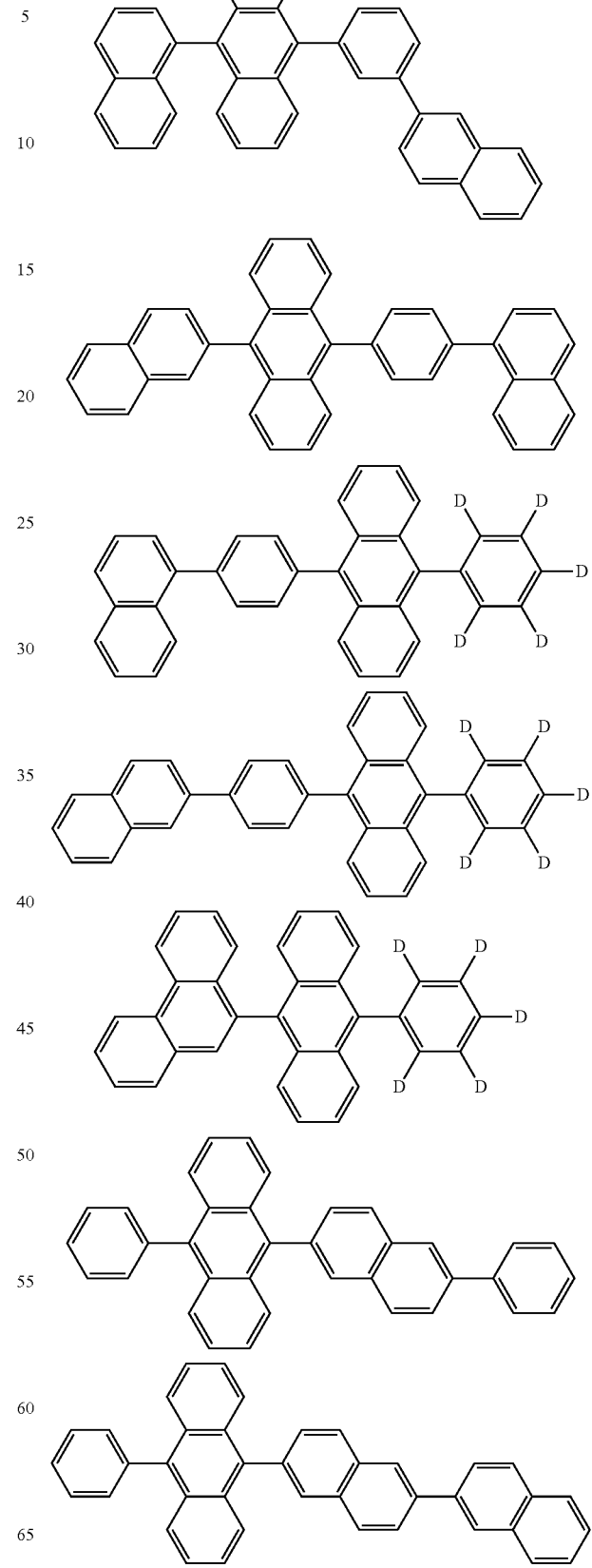

-continued
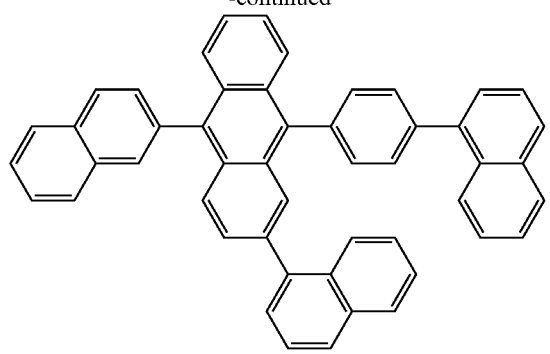
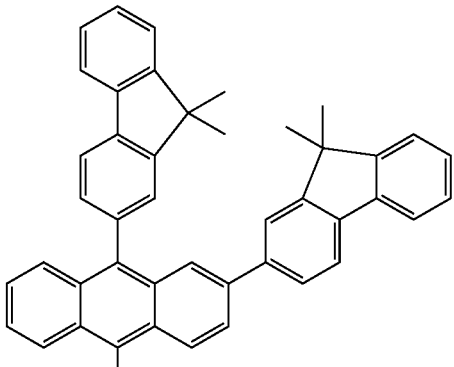
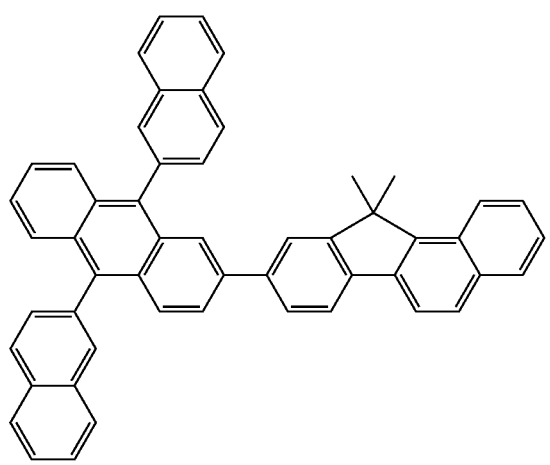
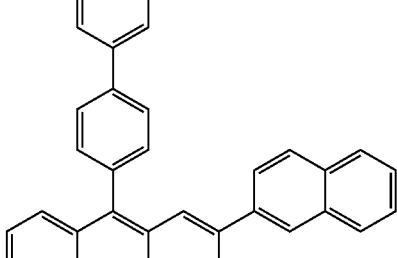
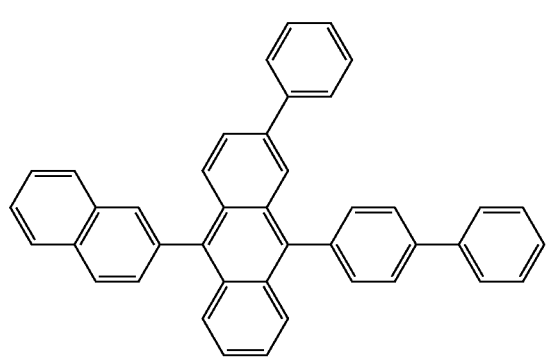
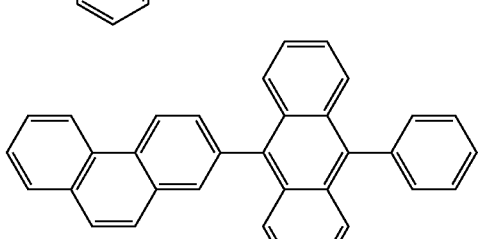
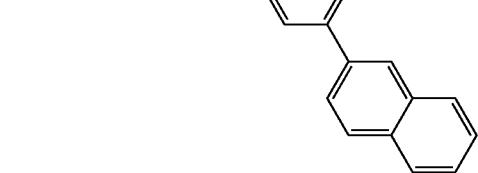
In another embodiment, an anthracene-based compound represented by Formula 401 below may be used as the host:

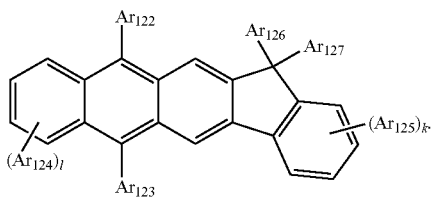

Formula 401

Detailed descriptions of groups represented by $Ar_{122}$ to $Ar_{125}$ in Formula 401 above are as described in the description of $Ar_{113}$ of Formula 400 above.

In Formula 401 above, each of $Ar_{126}$ and $Ar_{127}$ is independently a $C_1$-$C_{10}$ alkyl group (for example, a methyl group, an ethyl group, or a propyl group).

In Formula 401 above, k and l may each be independently an integer of 0 to 4. For example, k and l may be 0, 1, or 2.

For example, the anthracene-based compound represented by Formula 401 may be one of the compounds below, but is not limited thereto:

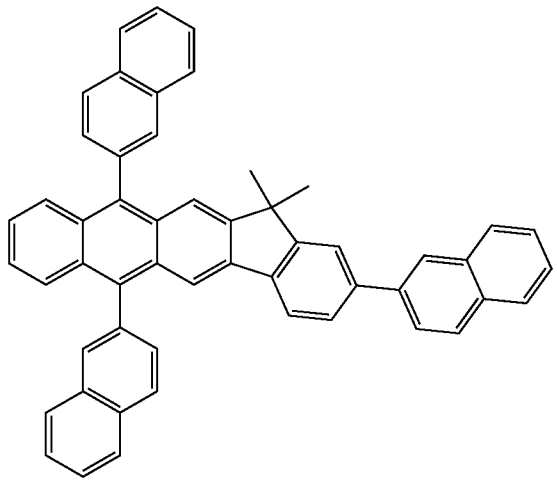

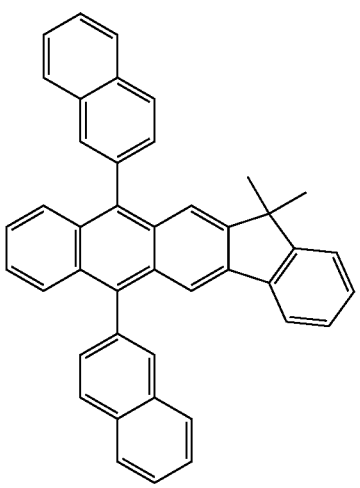

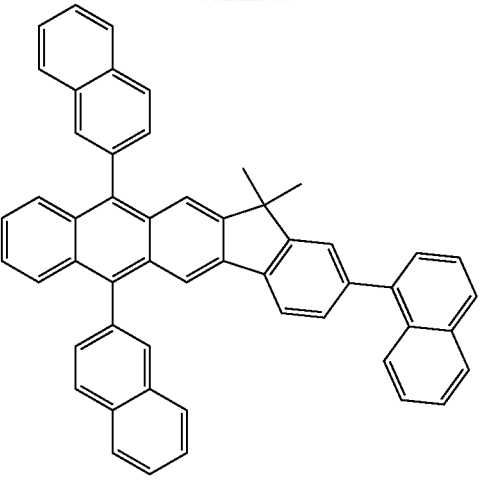

When the organic light-emitting device is a full color organic light-emitting device, the emission layer may be patterned into a red emission layer, a green emission layer, and a blue emission layer. In some embodiments, the emission layer may include at least two of the red emission layer, the green emission layer, and the blue emission layer that are stacked upon one another, or may emit white light, but is not limited thereto.

The dopant may be at least one of a fluorescent dopant and a phosphorescent dopant. The phosphorescent dopant may be an organic metal complex including a combination of two or more of Ir, Pt, Os, Re, Ti, Zr, and Hf, but is not limited thereto.

Non-limiting examples of suitable blue dopants are $F_2$Irpic, $(F_2\text{ppy})_2$Ir(tmd), Ir(dfppz)$_3$, ter-fluorene (fluorene), 4,4'-bis(4-diphenyl aminostyryl) biphenyl (DPAVBi), 2,5,8,11-tetra-tert-butyl perylene (TBPe), and DPVBi.

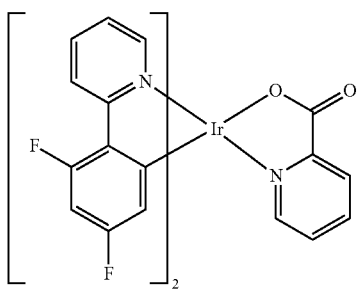
F₂Irpic
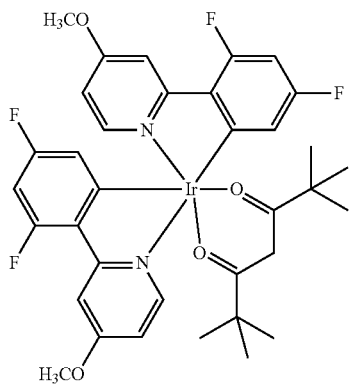
(F₂ppy)₂Ir(tmd)
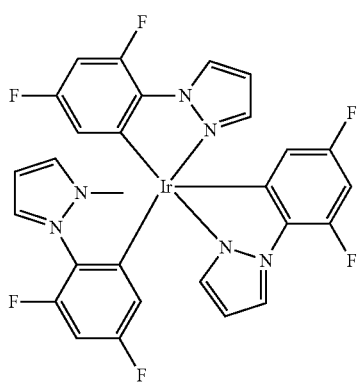
Ir(dfppz)₃
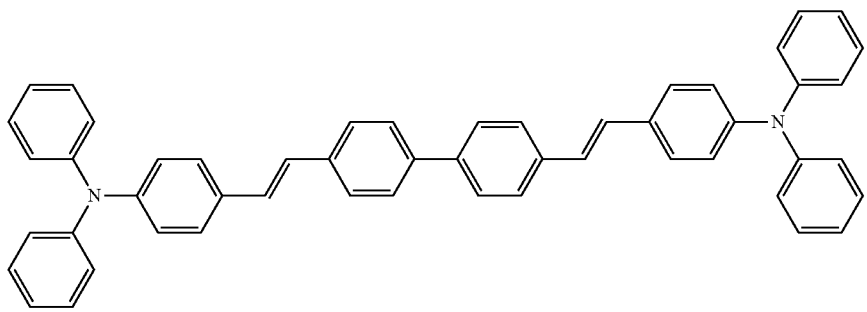
DPAVBi
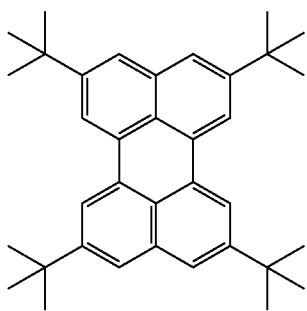
TBPe
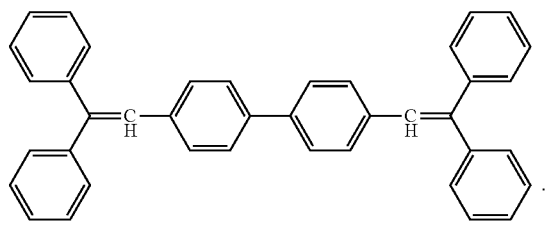
DPVBi Non-limiting examples of the green dopant include PtOEP, Ir(piq)₃, and BtpIr.

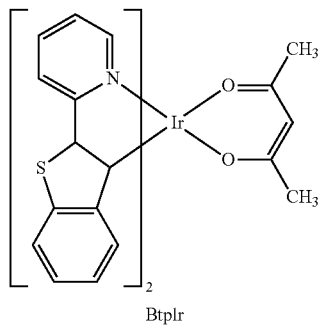

BtpIr

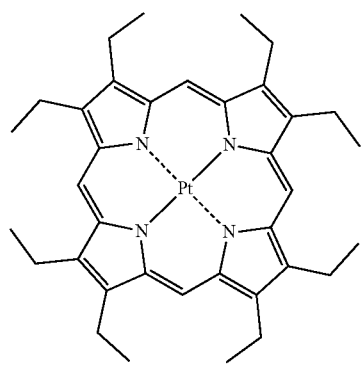

PtOEP

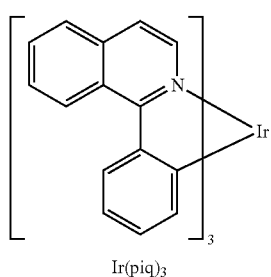

Ir(piq)₃

As a suitable green dopant, Ir(ppy)₃ (ppy=phenylpyridine), Ir(ppy)₂(acac), Ir(mpyp)₃, or the like may be used, but the green dopant is not limited thereto.

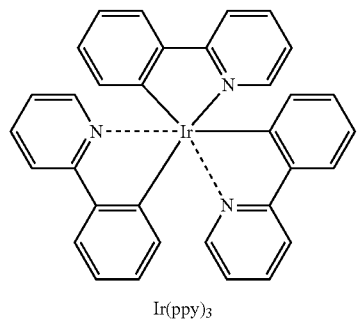

Ir(ppy)₃

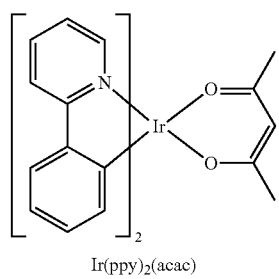

Ir(ppy)₂(acac)

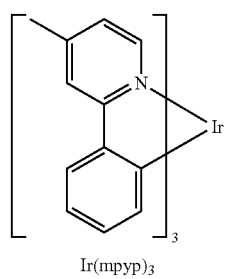

Ir(mpyp)₃

Meanwhile, the dopant that may be included in the EML 133 may be a Pt-complex as described below, but is not limited thereto:

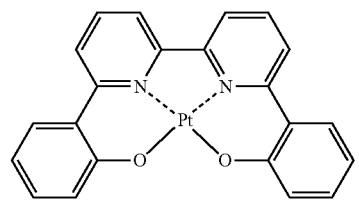

D1

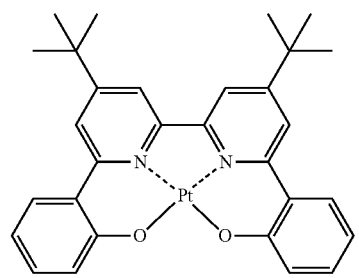

D2

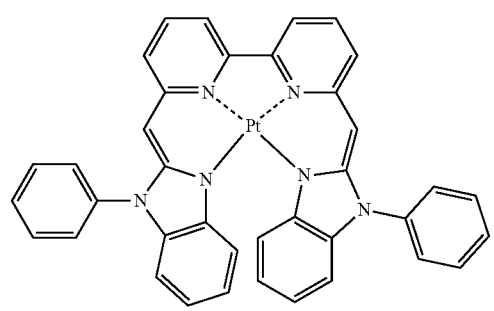

D3

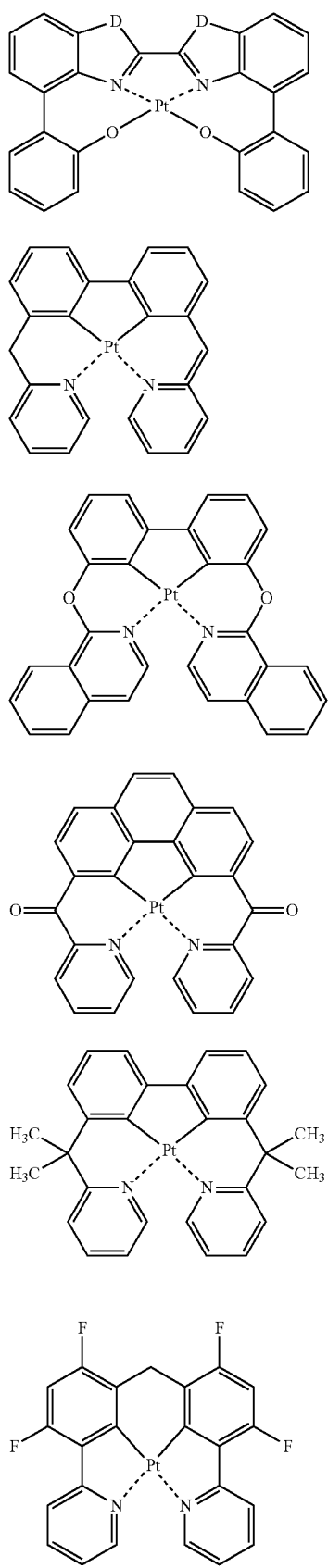
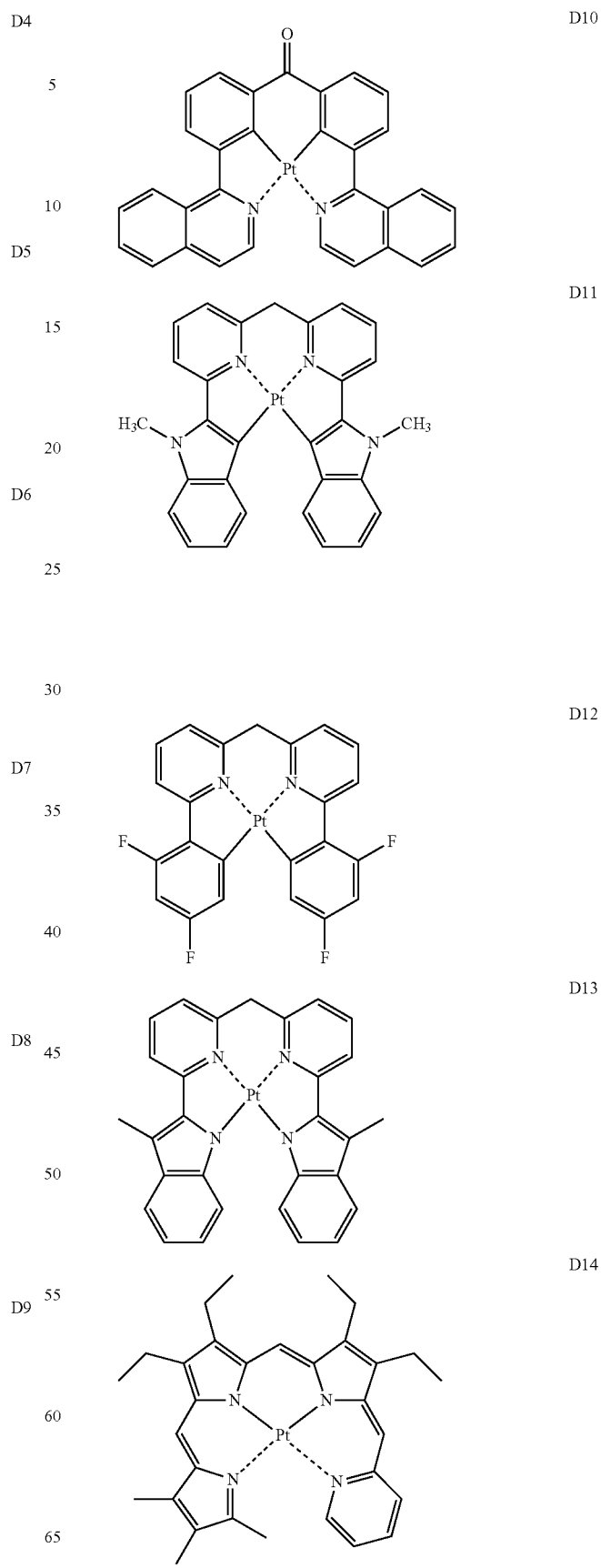

-continued
D15 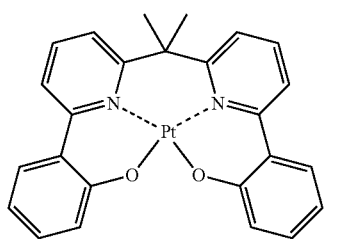
D16 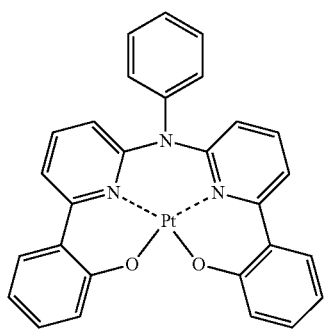
D17 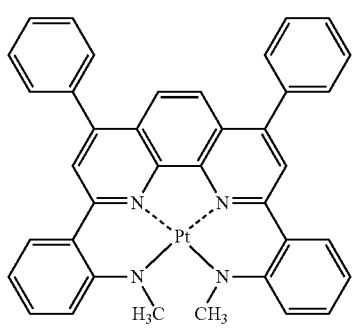
D18 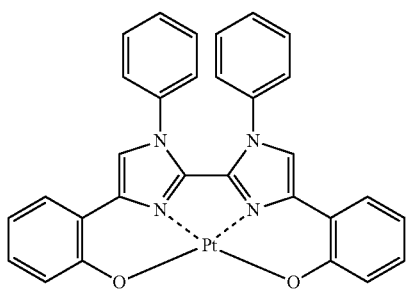
D19 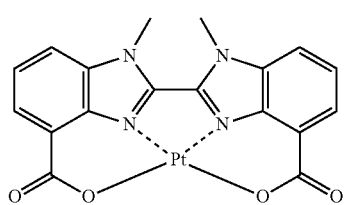
D20 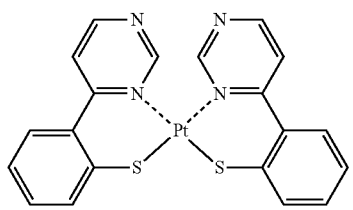
-continued
D21 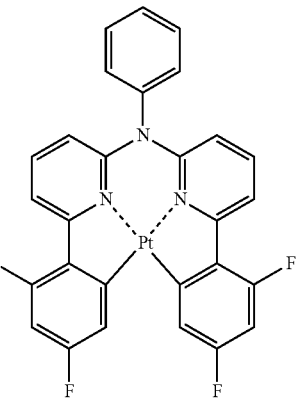
D22 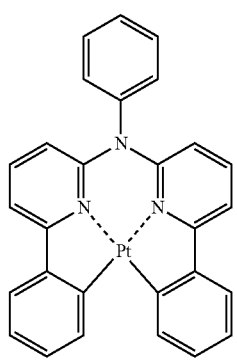
D23 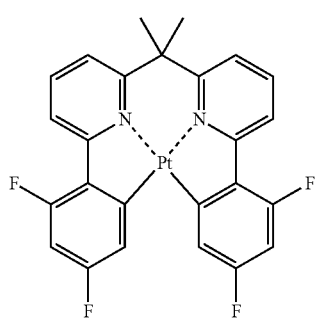
D24 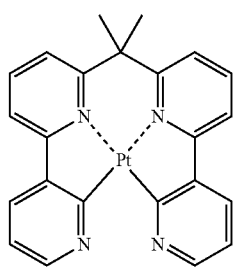
D25 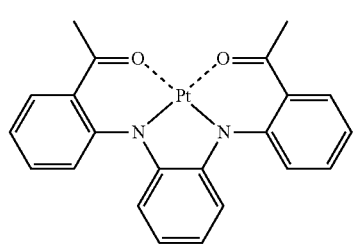

D26 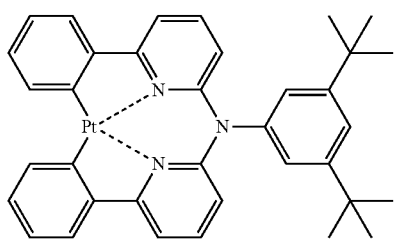
D27 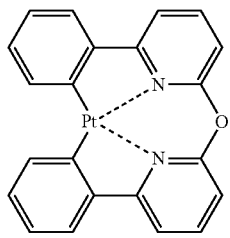
D28 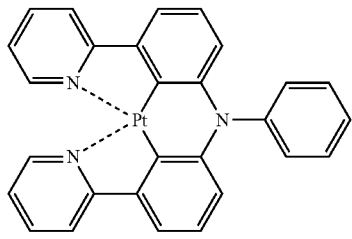
D29 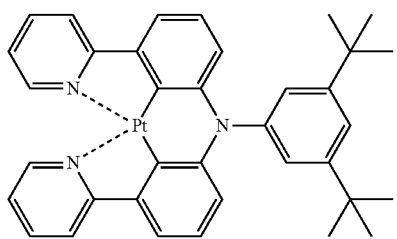
D30 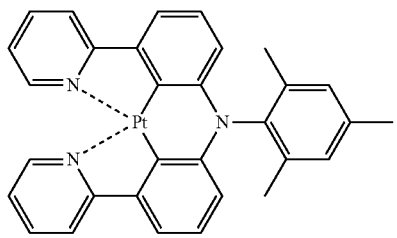
D31 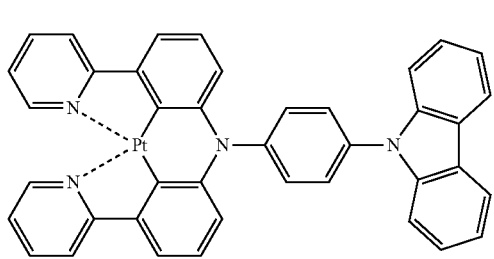
D32 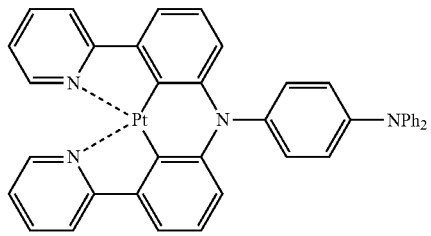
D33 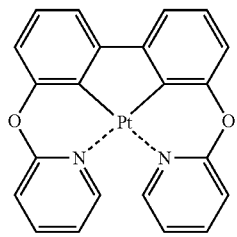
D34 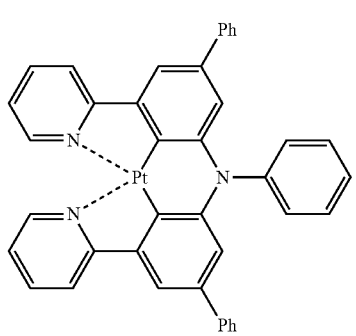
D35 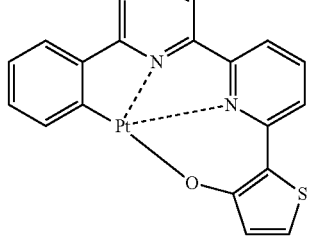
D36 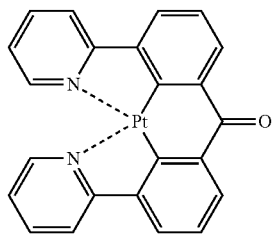

-continued
D37
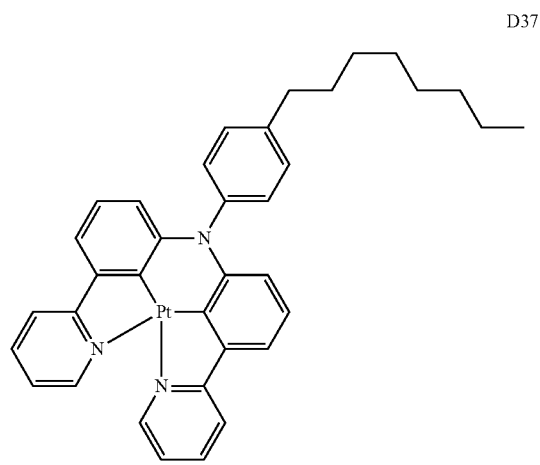
D38
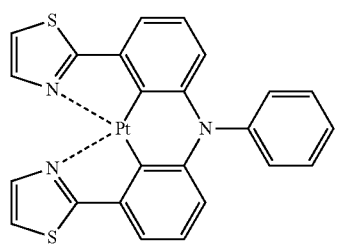
D39
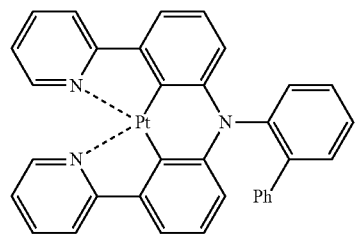
D40
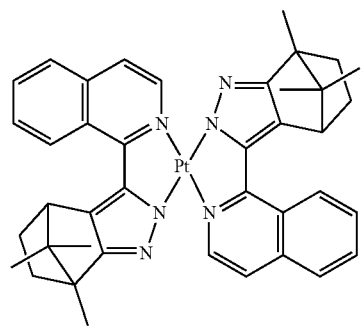
D41
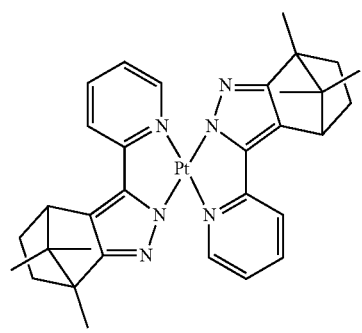
-continued
D42
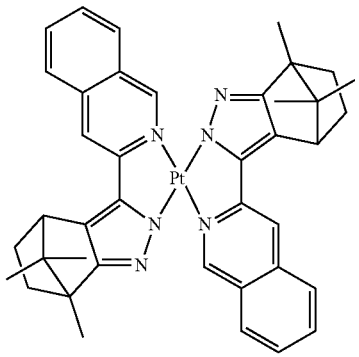
D43
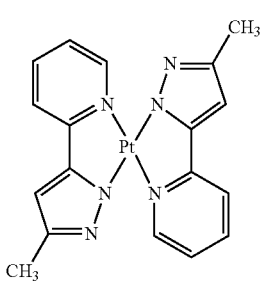
D44
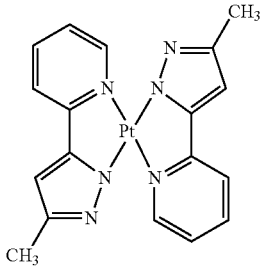
D45
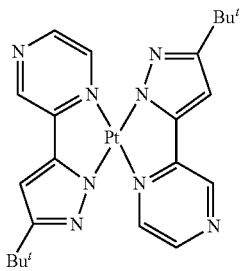
D46
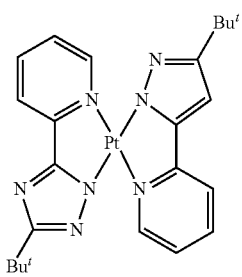

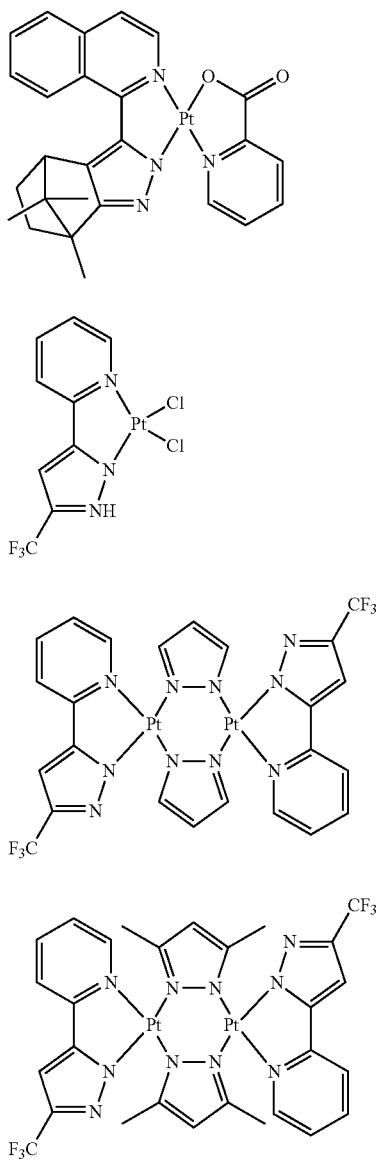

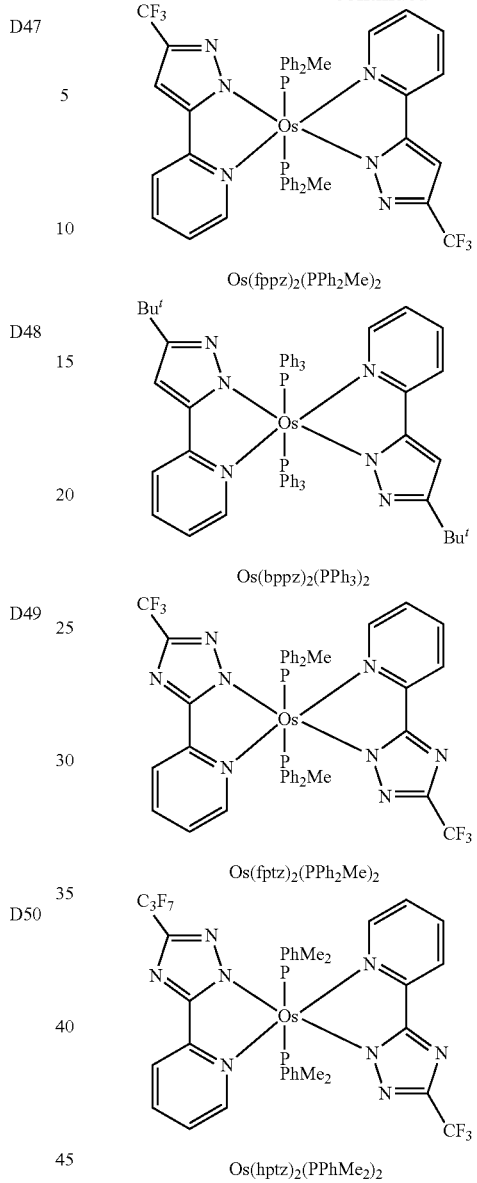

In some embodiments, the dopant that may be included in the EML 133 may be an Os-complex as described below, but is not limited thereto:

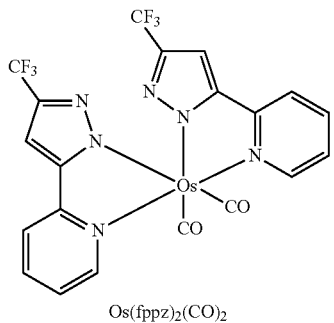

When the EML 133 includes a host and a dopant, the content of the dopant may generally be in a range of about 0.01 wt % to about 15 wt % of the total of 100 wt % of the EML 133, but the content is not limited thereto.

A thickness of the EML 133 may be about 200 Å to about 700 Å. In one embodiment, when the thickness of the EML 133 is within these ranges, the EML 133 has good light emitting ability without a substantial increase in driving voltage.

Then, an ETL 134 may be formed on the EML 133 by any of a variety of suitable methods, for example, vacuum deposition, spin coating, or casting. When the ETL 134 is formed using vacuum deposition or spin coating, the deposition or coating conditions may be similar to those for the formation of the HIL 131, though the deposition or coating conditions may vary according to a material that is used to form the ETL 134. Any suitable electron transporting material that may stably transport electrons injected from an electron injecting electrode (cathode) may be used as a material for the ETL 134. Non-limiting examples of materials suitable for forming the ETL 134 are quinoline derivatives such as tris(8-quinolinorate)aluminum (Alq$_3$), TAZ, BAlq, beryllium bis(benzoquinolin-10-olate (Bebq$_2$), 9,10-di(naphthalene-2-yl)anthracene (ADN), Compound 101, Compound 102, or Bphen, but are not limited thereto.

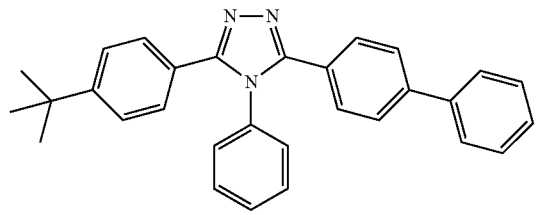

TAZ

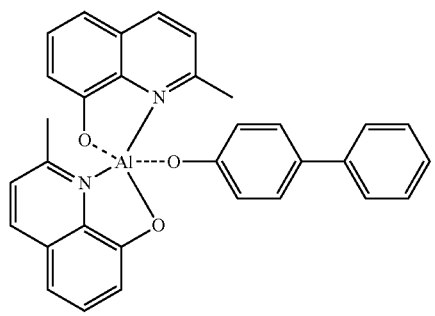

BAlq

Compound 101

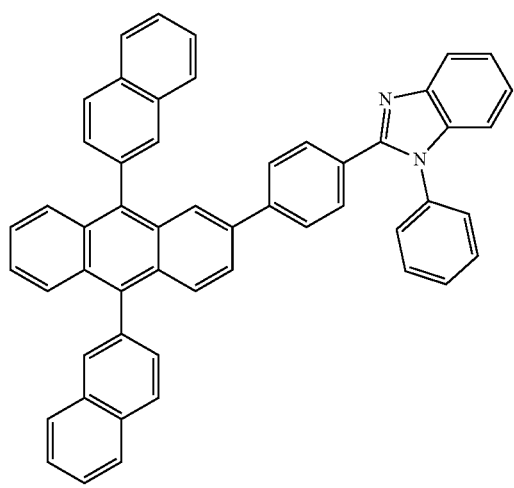

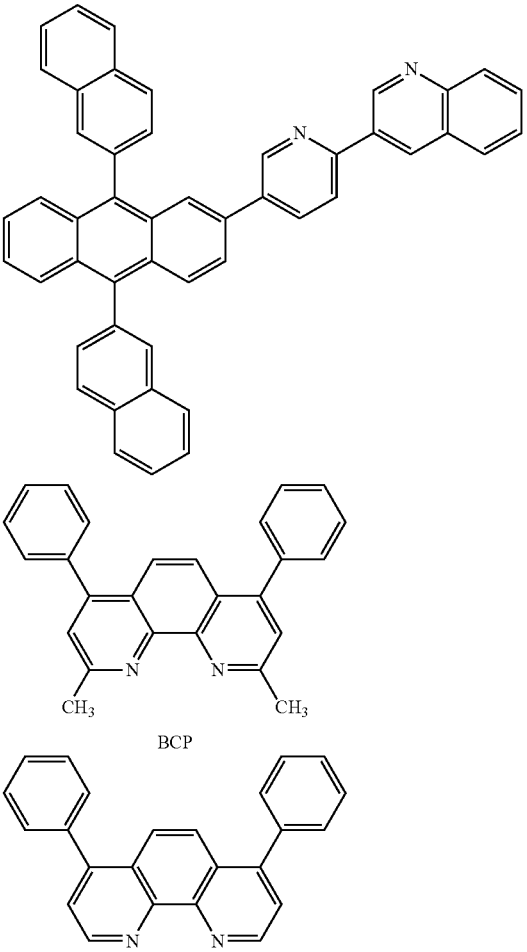

Compound 102

BCP

Bphen

A thickness of the ETL 134 may be from about 100 Å to about 1000 Å, for example from about 150 Å to about 500 Å. In one embodiment, when the ETL 134 is within the range above, the ETL 134 has good electron transporting ability without a substantial increase in driving voltage.

In some embodiments, the ETL 134 may further include a metal-containing material, in addition to any suitable electron transporting organic compound. The metal-containing material may include an Li complex. Non-limiting examples of the Li complex are lithium quinolate (LiQ) and Compound 203 below:

Compound 203

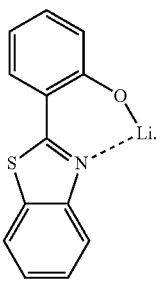

Then, an EIL 135, which facilitates injection of electrons from the cathode, may be formed on the ETL 134. Any suitable electron-injecting material may be used to form the EIL 135.

Non-limiting examples of suitable materials for forming the EIL 135 are LiF, NaCl, CsF, Li$_2$O, and BaO. The deposition or coating conditions when forming the EIL 135 may be similar to those for the formation of the HIL 131, though the deposition or coating conditions may vary according to the compound that is used to form the EIL 135.

A thickness of the EIL 135 may be from about 1 Å to about 100 Å, and in some embodiments, may be from about 3 Å to about 90 Å. In one embodiment, when the thickness of the EIL 135 is within these ranges, the EIL 135 has satisfactory electron injecting ability without a substantial increase in driving voltage.

The second electrode 140 is disposed on the organic layer 130. The second electrode 140 may be a cathode that is an electron injecting electrode. A suitable material for forming the second electrode 140 may be a metal, an alloy, an electro-conductive compound, which have a low work function, or a mixture thereof. In this regard, the second electrode 140 may be formed of lithium (Li), magnesium (Mg), aluminum (Al), aluminum-lithium (Al-lithium), calcium (Ca), magnesium-indium (Mg—In), magnesium-silver (Mg—Ag), or the like, and may be formed as a thin film transmission electrode. In some embodiments, to manufacture a top-emission light-emitting device, the transmission electrode may be formed of indium tin oxide (ITO) or indium zinc oxide (IZO).

When a phosphorescent dopant is used in the EML 133, a hole blocking layer (HBL) may be formed between the HTL 132 and the EML 133 or the H-functional layer and the EML 133 by using vacuum deposition, spin coating, casting, LB deposition, or the like, in order to prevent diffusion of triplet excitons or holes into the ETL 134. When the HBL is formed using vacuum deposition or spin coating, the conditions for deposition or coating may be similar to those for the formation of the HIL 131, although the conditions for deposition or coating may vary according to the material that is used to form the HBL. Suitable hole blocking materials may be used, and examples of suitable hole blocking materials include oxadiazole derivatives, triazole derivatives, and phenanthroline derivatives. For example, BCP, as shown below, may be used as a hole blocking layer material.

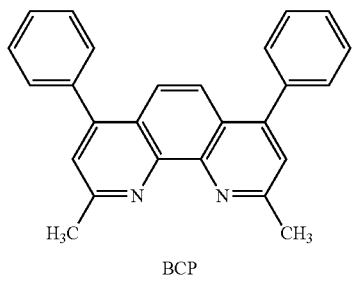 [SMILES: Cc1cc(-c2ccccc2)c2ccc3c(-c4ccccc4)cc(C)nc3c2n1 ; "BCP"]

BCP

A thickness of the HBL may be from about 20 Å to about 1000 Å, and in some embodiments, may be from about 30 Å to about 300 Å. In one embodiment, when the thickness of the HBL is within these ranges, the HBL has improved hole blocking ability without a substantial increase in driving voltage.

Figure 2:
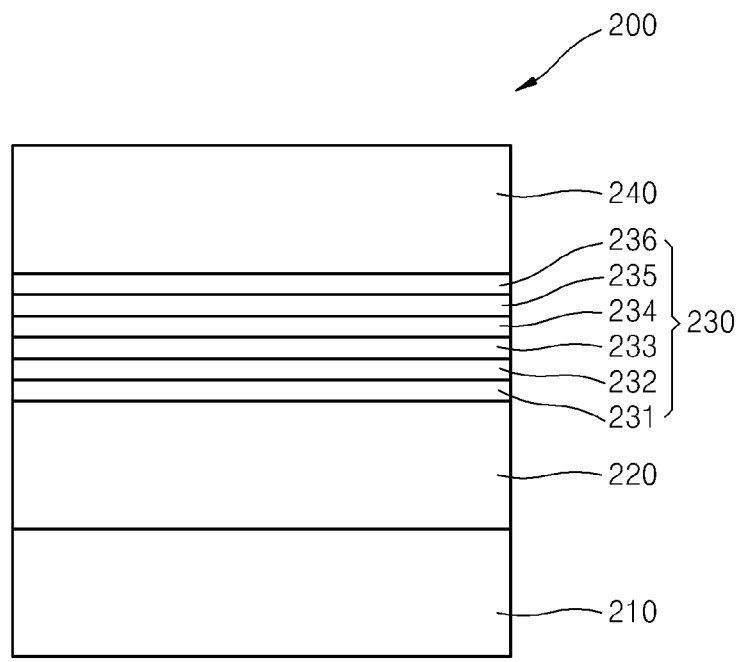
FIG. 2 is a schematic view illustrating a structure of an organic light emitting diode according to another embodiment.

FIG. 2 is a schematic view illustrating a structure of an organic light emitting diode 200 according to another embodiment. The organic light emitting diode 200 is the same as the organic light emitting diode 100, except that an HTL of the organic light emitting diode 200 includes a first hole transporting layer 232 and a second hole transporting layer 233.

The first hole transporting layer 232 may be deposited on the hole injecting layer 231 and the second hole transporting layer 233 may be deposited on the first hole transporting layer 232.

Materials included in the first hole transporting layer 232 and the second hole transporting layer 233 may be the same or different. However, at least one layer of the first hole transporting layer 232 and the second hole transporting layer 233 may include an arylamine-based compound of Formula 1.

Although the organic light-emitting devices 100 and 200 are described with references to FIGS. 1 and 2, the organic light emitting devices are not limited thereto.

As used herein, specific examples of an unsubstituted $C_1$-$C_{60}$ alkyl group (or a $C_1$-$C_{60}$ alkyl group) include a linear or a branched $C_1$-$C_{60}$ alkyl group such as methyl, ethyl, propyl, isobutyl, sec-butyl, pentyl, iso-amyl, or hexyl. A substituted $C_1$-$C_{60}$ alkyl group is the unsubstituted $C_1$-$C_{60}$ alkyl group wherein at least one hydrogen atom is substituted with one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, or a phosphoric acid group or a salt thereof; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridyl group, a pyrimidyl group, a pyrazinyl group, a pyridazinyl group, a triazinyl group, a quinolyl group, or an isoquinolyl group;

—N($Q_{11}$)($Q_{12}$); or

—Si($Q_{13}$)($Q_{14}$)($Q_{15}$) (where, $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

As used herein, an unsubstituted $C_1$-$C_{60}$ alkoxy group (or a $C_1$-$C_{60}$ alkoxy group) has a formula of —OA (wherein A is the unsubstituted $C_1$-$C_{60}$ alkyl group described above), and specific examples of the unsubstituted $C_1$-$C_{60}$ alkoxy group include methoxy, ethoxy, and isopropyloxy. At least one hydrogen atom of the unsubstituted $C_1$-$C_{60}$ alkoxy group may be substituted with those substituents described above in conjunction with the substituted $C_1$-$C_{60}$ alkyl group.

As used herein, an unsubstituted $C_2$-$C_{60}$ alkenyl group (or a $C_2$-$C_{60}$ alkenyl group) is a hydrocarbon chain having a carbon-carbon double bond in the center or at a terminal of an unsubstituted $C_2$-$C_{60}$ alkyl group. Examples of the unsubstituted $C_2$-$C_{60}$ alkenyl group are an ethenyl group, a propenyl group, and a butenyl group. At least one hydrogen atom in the unsubstituted $C_2$-$C_{60}$ alkenyl group may be substituted with those substituents described above in conjunction with the substituted $C_1$-$C_{60}$ alkyl group.

As used herein, an unsubstituted $C_2$-$C_{60}$ alkynyl group (or a $C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group are an ethynyl group, a propynyl group, and the like. At least one hydrogen atom in the unsubstituted $C_2$-$C_{60}$ alkynyl group may be substituted with those substituents described above in conjunction with the substituted $C_1$-$C_{60}$ alkyl group.

As used herein, an unsubstituted $C_3$-$C_{30}$ cycloalkyl group is a monovalent group having a saturated carbocyclic aromatic system having 3 to 30 carbon atoms. Examples of the unsubstituted $C_3$-$C_{30}$ cycloalkyl group include cyclopropyl, cyclobutyl, cyclopentyl, cyclohexyl, cyclooctyl, and the like. At least one hydrogen atom in the unsubstituted $C_3$-$C_{30}$ cycloalkyl group may be substituted with those substituents described above in conjunction with the substituted $C_1$-$C_{60}$ alkyl group.

As used herein, an unsubstituted $C_3$-$C_{30}$ cycloalkenyl group is an unsaturated hydrocarbon ring group that is not an aromatic ring, having at least one carbon-carbon double bond. Examples of the unsubstituted $C_3$-$C_{30}$ cycloalkenyl group include cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, a 1,5-cyclooctadienyl group, and the like. At least one hydrogen atom of the cycloalkenyl group may be substituted with those substituents described above in conjunction with the substituted $C_1$-$C_{60}$ alkyl group.

As used herein, an unsubstituted $C_6$-$C_{60}$ aryl group is a monovalent group having a carbocyclic aromatic system having 6 to 60 carbon atoms including at least one aromatic ring, and an unsubstituted $C_6$-$C_{60}$ arylene group is a divalent group having a carbocyclic aromatic system having 6 to 60 carbon atoms including at least one aromatic ring. When the unsubstituted $C_6$-$C_{60}$ aryl group and the unsubstituted $C_6$-$C_{60}$ arylene group include at least two rings, two or more rings may be fused to each other. At least one hydrogen atom of the unsubstituted $C_6$-$C_{60}$ aryl group and the unsubstituted $C_6$-$C_{60}$ arylene group may be substituted with those substituents described above in conjunction with the substituted $C_1$-$C_{60}$ alkyl group.

Examples of a substituted or unsubstituted $C_6$-$C_{60}$ aryl group include a phenyl group, a $C_1$-$C_{10}$ alkyl phenyl group (for example, an ethyl phenyl group), a $C_1$-$C_{10}$ alkyl biphenyl group (for example, an ethyl biphenyl group), a halophenyl group (for example, an o-, m- and p-fluorophenyl group, and a dichlorophenyl group), a dicyanophenyl group, a trifluoromethoxy phenyl group, an o-, m-, and p-tolyl group, an o-, m- and p-cumenyl group, a mesityl group, a phenoxy phenyl group, an ($\alpha,\alpha$-dimethyl benzene)phenyl group, an (N,N'-dimethyl)aminophenyl group, an (N,N'-diphenyl)aminophenyl group, a pentalenyl group, an indenyl group, a naphthyl group, a halonaphthyl group (for example, a fluoronaphthyl group), a $C_1$-$C_{10}$ alkyl naphthyl group (for example, a methyl naphthyl group), a $C_1$-$C_{10}$ alkoxy naphthyl group (for example, a methoxy naphthyl group), an anthracenyl group, an azulenyl group, a heptalenyl group, an acenaphthylenyl group, a phenalenyl group, a fluorenyl group, an anthraquinolyl group, a methyl anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group, and the like, and examples of the substituted $C_6$-$C_{60}$ aryl group may be inferred based on the examples of the unsubstituted $C_6$-$C_{60}$ aryl group and those substituents described above in conjunction with the substituted $C_1$-$C_{60}$ alkyl group. The substituted or unsubstituted $C_6$-$C_{60}$ arylene group may be inferred based on the examples of the substituted or unsubstituted $C_6$-$C_{60}$ aryl group.

As used herein, an unsubstituted $C_2$-$C_{60}$ heteroaryl group is a monovalent group having a system formed of at least one aromatic ring that includes at least one heteroatom selected from N, O, P, or S as ring-forming atoms and carbon atoms as other ring atoms, and an unsubstituted $C_2$-$C_{60}$ heteroarylene group is a divalent group having a system formed of at least one aromatic ring that includes at least one heteroatom selected from N, O, P, or S as ring-forming atoms and carbon atoms as other ring atoms. Here, when the unsubstituted $C_2$-$C_{60}$ heteroaryl group and the unsubstituted $C_2$-$C_{60}$ heteroarylene group include two or more rings, the two or more rings may be fused to each other. At least one hydrogen atom of the unsubstituted $C_2$-$C_{60}$ heteroaryl group and the unsubstituted $C_2$-$C_{60}$ heteroarylene group may be substituted with those substituents described above in conjunction with the substituted $C_1$-$C_{60}$ alkyl group.

Examples of the unsubstituted $C_2$-$C_{60}$ heteroaryl group include, a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, an imidazopyrimidinyl group, and the like. Examples of the unsubstituted $C_2$-$C_{60}$ heteroarylene group may be inferred based on the examples of a substituted or unsubstituted $C_2$-$C_{60}$ arylene group.

A substituted or unsubstituted $C_6$-$C_{60}$ aryloxy group is represented by —$OA_2$ (where, $A_2$ is a substituted or unsubstituted $C_6$-$C_{60}$ aryl group), and a substituted or unsubstituted $C_6$-$C_{60}$ arylthio group is represented by —$SA_3$ (where, $A_3$ is a substituted or unsubstituted $C_6$-$C_{60}$ aryl group).

Hereinafter, an organic light-emitting device according to an embodiment of the present inventive concept will be described in greater detail with references to Examples; however, the present inventive concept is not limited by the following Synthesis Examples and Examples.

SYNTHESIS EXAMPLES
Synthesis of Intermediate I-1 to I-10
Reaction Formula 1
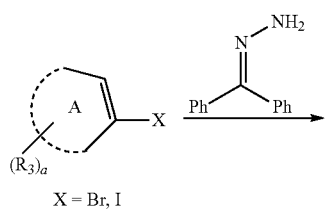
X = Br, I
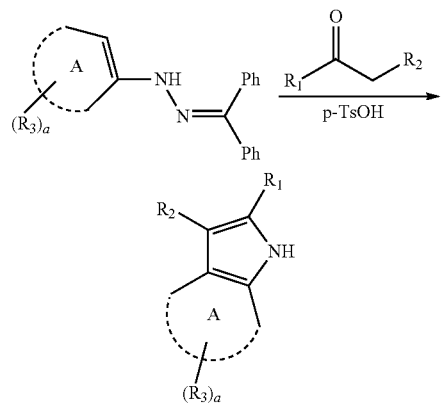
R$_1$, R$_2$ = Me or Ph
As shown in Reaction Formula 1 above, an aromatic halogen compound or a heteroaromatic halogen compound are reacted with benzophenone hydrazine to produce hydrazone, which is then condensed with ketone to synthesize the following Intermediates I-1 to I-10.
I-1
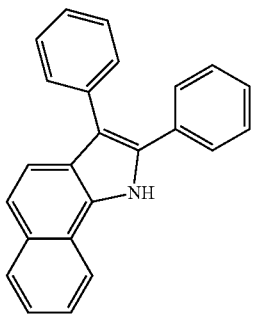
I-2
I-3
I-4
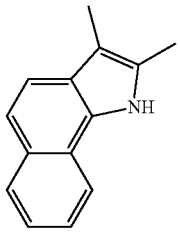
I-5
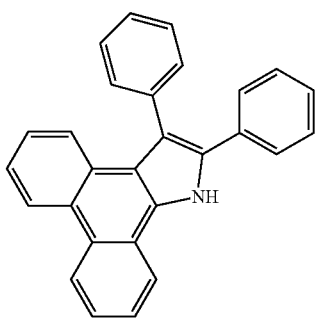
I-6
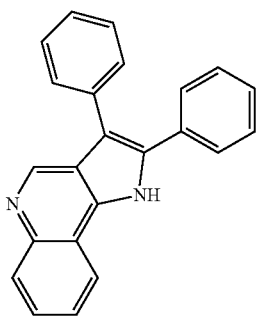
I-7
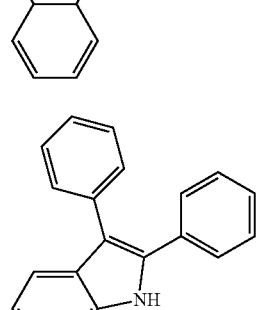

-continued

I-8

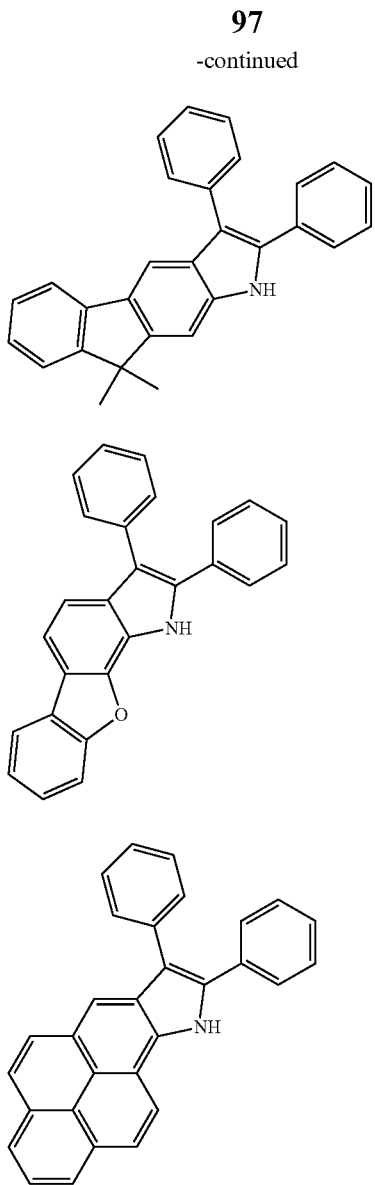

I-9

I-10

The synthesis of the Intermediate I-1 is described in greater detail as a representative Example of the Intermediates I-1 to I-10. One of ordinary skill in the art may easily synthesize the Intermediates I-2 to I-10 based on Reaction Formula 1 above and the synthesis of Intermediate I-1.

Synthesis of Intermediate I-1

Reaction Formula 2

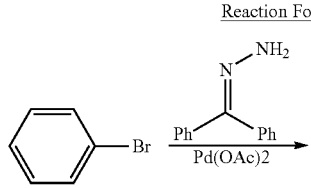

-continued

I-1(a)

I-1

(1) Synthesis of Intermediate I-1(a)

1.57 g (10.0 mmol) of bromobenzene, 2.35 g (12.0 mmol) of benzophenone hydrazone, 1.44 g (15.0 mmol) of t-BuONa, 0.05 g (0.2 mmol) of Pd(OAc)$_2$, and 0.01 g (0.2 mmol) of 2-dicyclohexylphosphino-2',4',6'-triisopropyl biphenyl were dissolved in 30 mL of toluene and then agitated at a temperature of 90° C. for 3 hours to prepare a reactant. The reactant was cooled to room temperature, distilled water was added to the reactant, the reactant was then extracted twice with 30 mL of diethylether, and then extracted once with 30 mL of dichloromethane to collect an organic layer. The collected organic layer was dried with magnesium sulfate and then filtered, and the solvent was evaporated from the organic layer. Obtained residues were isolated and purified using silica gel chromatography to obtain 2.56 g of Intermediate I-1 (a) (yield 94%) and the compound produced was characterized through liquid chromatography-mass spectrometry (LCMS).

(2) Synthesis of Intermediate I-1

40 mL of ethanol and 40 mL of toluene were added to a mixture of 2.56 g (9.4 mmol) of Intermediate I-1(a), 3.80 g (20.0 mmol) of p-toluene sulfonic acid monohydrate, and 2.74 g (38.0 mmol) of methyl ethyl ketone, and then agitated at a temperature of 110° C. for 24 hours to produce a reaction product. The reaction product was cooled to room temperature, distilled water was added to the reaction product, then the reaction product was extracted twice with 50 mL of diethylether, and extracted twice with 30 mL of dichloromethane to collect an organic phase. The collected organic phase was dried with magnesium sulfate, filtered, and then a solvent was evaporated from the organic phase. Obtained residues were isolated and purified using silica gel chromatography to obtain 1.16 g of Intermediate I-1 (yield 85%) and the compound produced was characterized through LCMS.

LCMS (C$_{10}$H$_{11}$N): calculated 145.1; actual 146.1

Synthesis of Intermediate A-1 to A-16

Reaction Formula 3

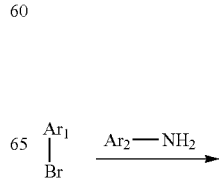

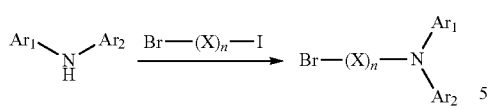
As shown in Reaction Formula 3, an amination reaction using a palladium catalyst between aromatic halogen compound and an aromatic amine compound may be used to synthesize Intermediates A-1 to A-16 below.
A-1
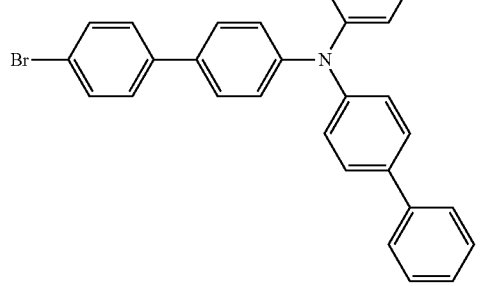
A-2
A-3
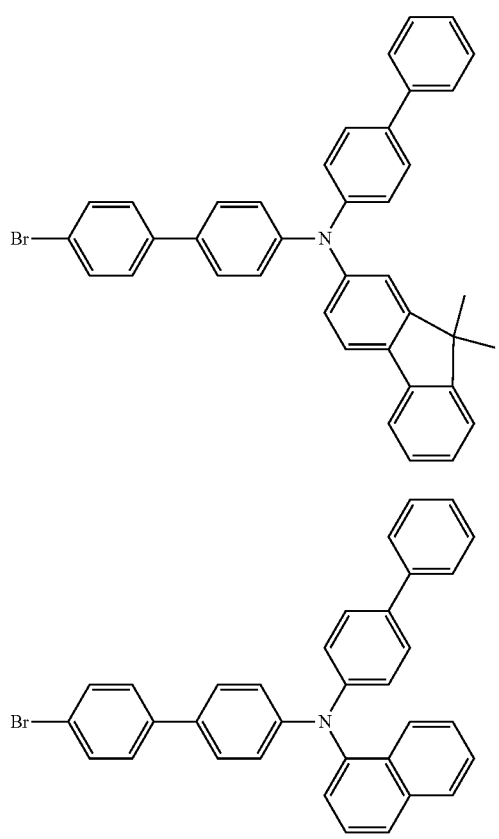
A-4
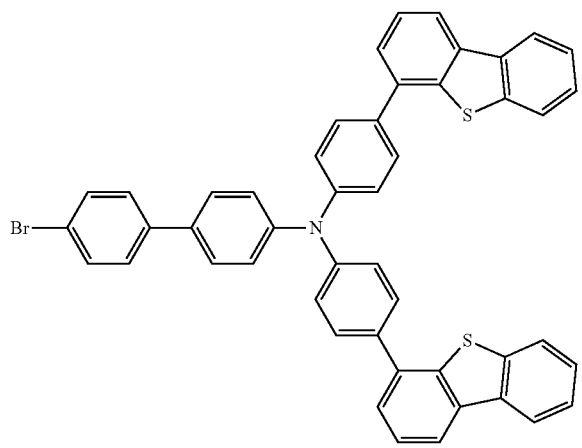
A-5
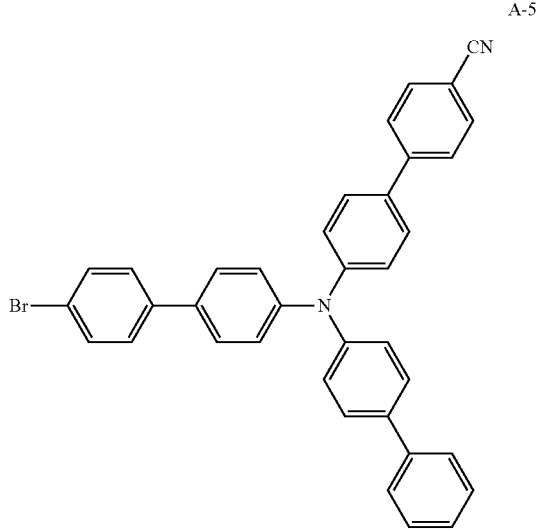
A-6
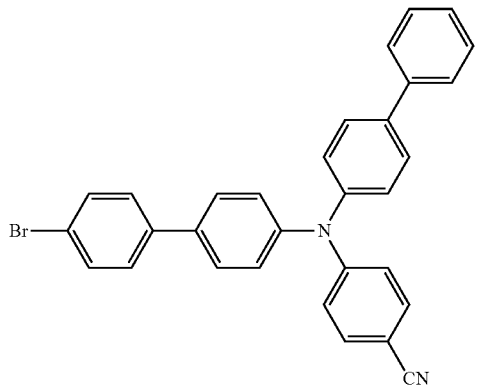

-continued
A-7
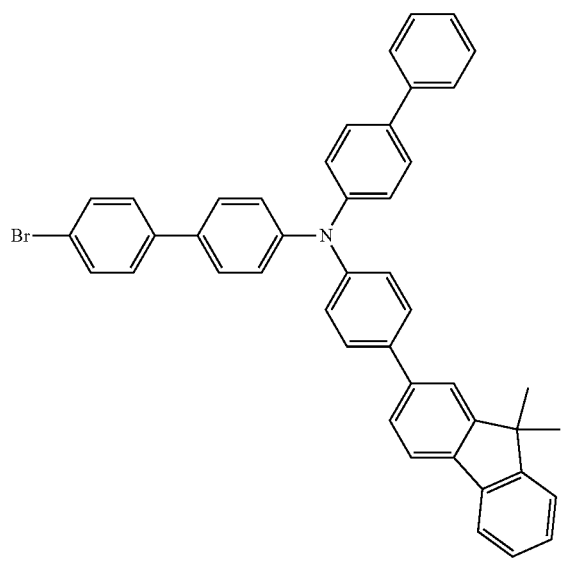
A-8
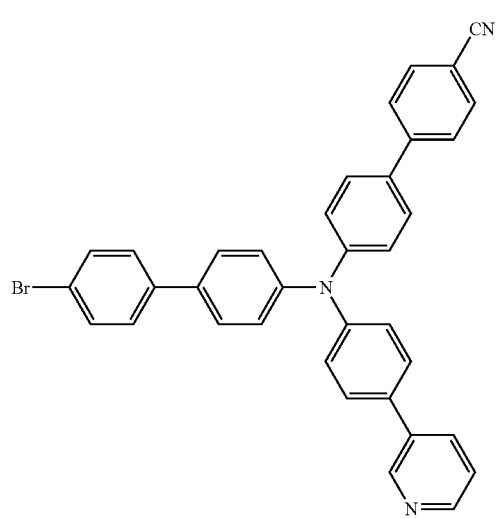
A-9
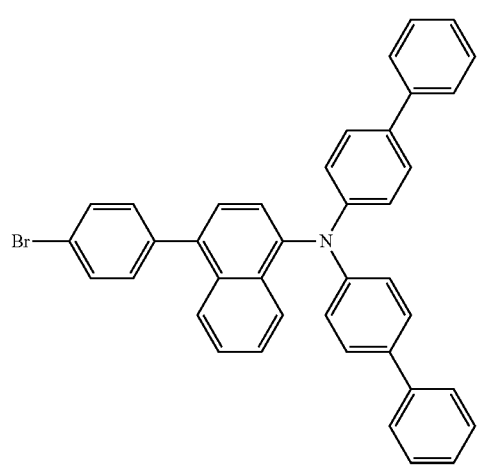
-continued
A-10
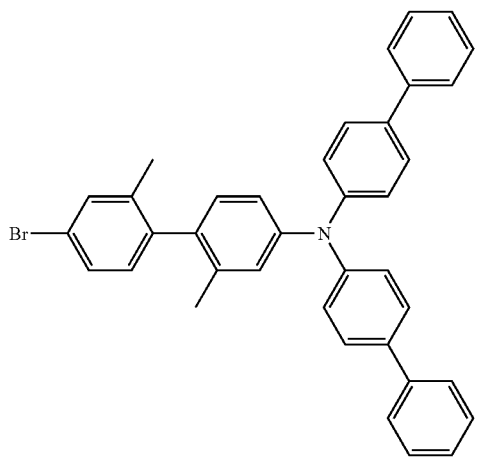
A-11
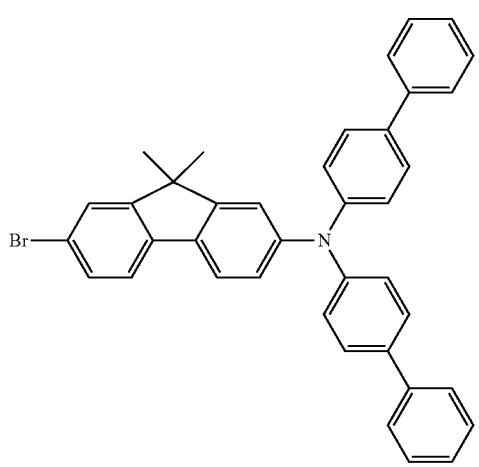
A-12
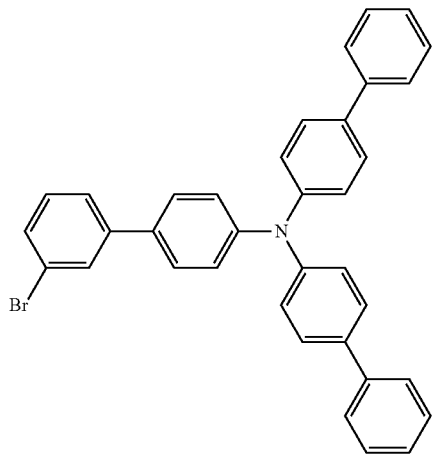

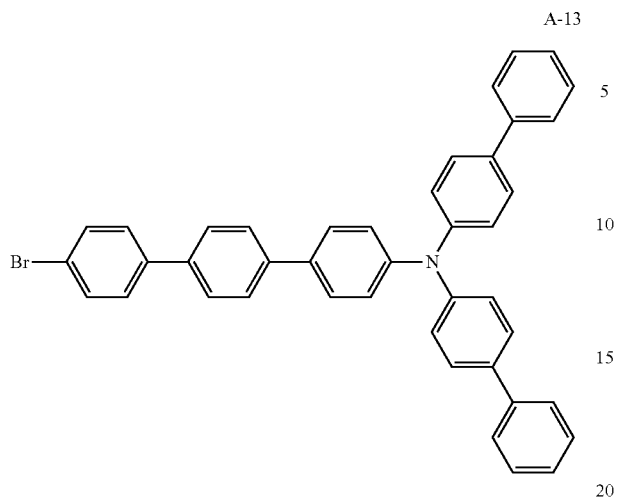
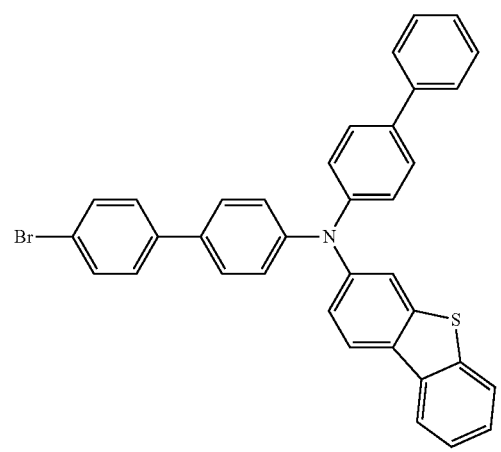
Synthesis of A-1 is described in greater detail as a representative Example of Intermediates A-1 to A-16. One of ordinary skill in the art may easily synthesize the Intermediates A-2 to A-16 based on Reaction Formula 4 above the synthesis of Intermediate A-1.
Synthesis of Intermediate A-1
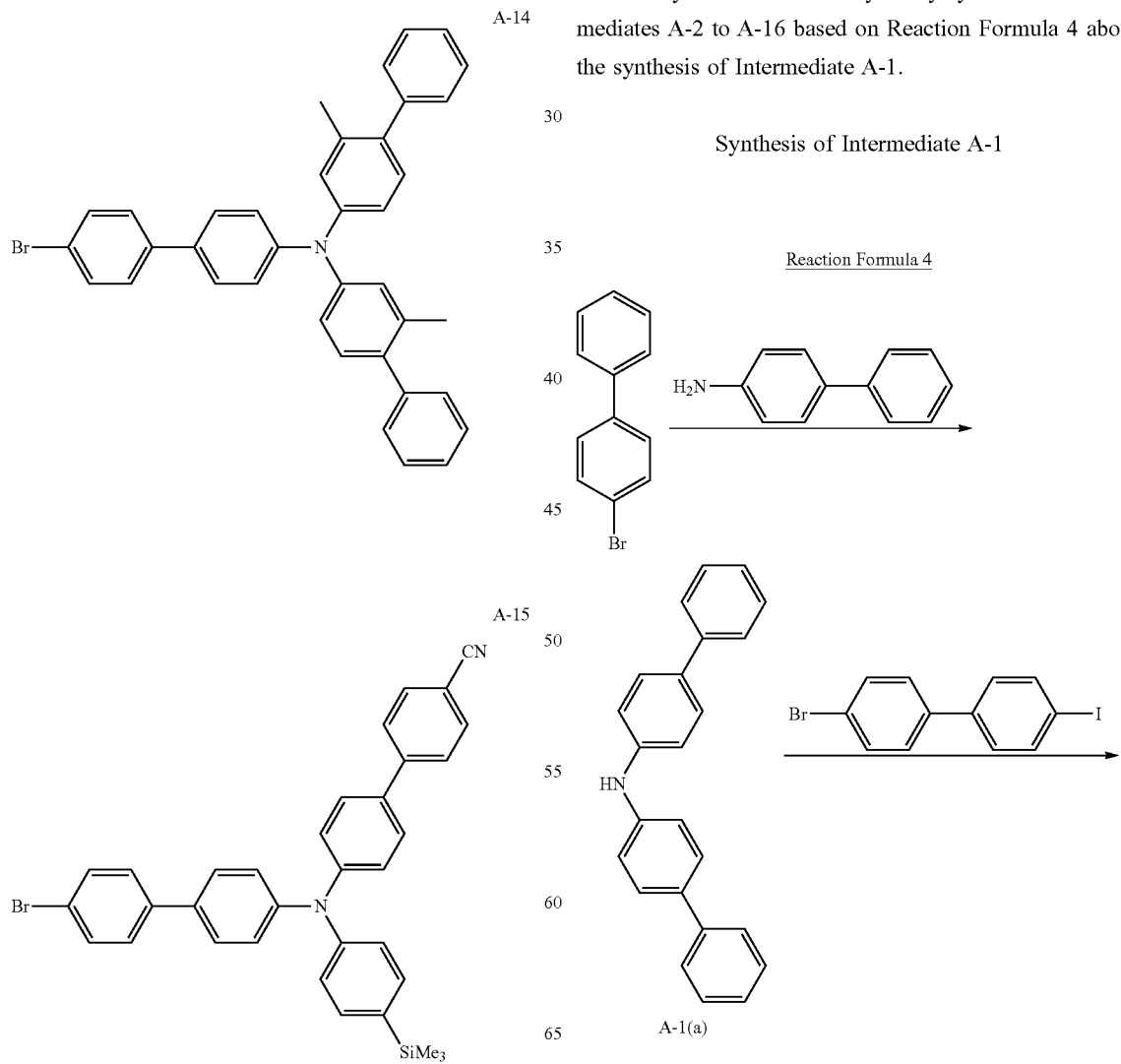

-continued

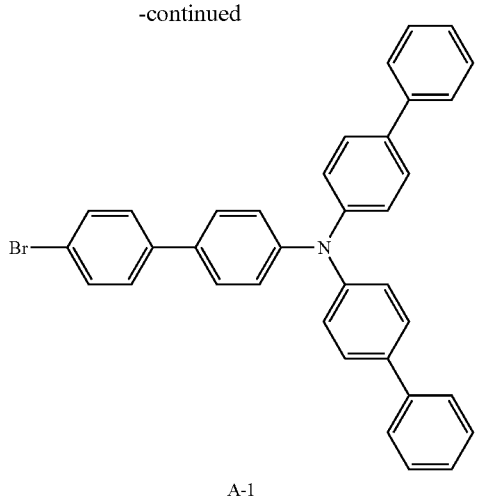

A-1

(1) Synthesis of Intermediate A-1(a)

7 g (30.0 mmol) of 2-bromobiphenyl, 7.62 g (45.0 mmol) of 4-aminobiphenyl, 4.3 g (45.0 mmol) of t-BuONa, 0.55 g (0.6 mmol) of $Pd_2(dba)_3$, and 0.12 g (0.6 mmol) of $(t-Bu)_3P$ were dissolved in 100 mL and then agitated at a temperature of 90° C. for three hours to produce a reaction product. After the reaction was completed, the reaction product was cooled to room temperature, distilled water was added to the reaction product, and then the reaction product was extracted three times with 100 mL of diethylether to collect an organic phase. The collected organic phase was dried with magnesium sulfate and then a solvent was evaporated from the organic phase. Obtained residues were isolated and purified using silica gel chromatography to obtain 8.77 g of Intermediate A-1(a)(yield 91%) and the compound produced was characterized through LCMS.

LCMS ($C_{24}H_{19}N$): calculated 321.1; actual 322.1

(2) Synthesis of Intermediate A-1

3.21 g (10.0 mmol) of Intermediate A-1(a), 17.9 g (50.0 mmol) 4-bromo-4'-iodidebiphenyl, 2.88 g (30.0 mmol) of t-BuONa, 0.28 g (0.3 mmol) of $Pd_2(dba)_3$, and 0.6 g (0.3 mmol) of $(t-Bu)_3P$ were dissolved in 100 mL of toluene and then agitated at a temperature of 90° C. for three hours. After the reaction was completed, the reaction product was cooled to room temperature, distilled water was added to the reaction product, and then the reaction product was extracted three times with 100 mL of diethylether to collect an organic phase. The collected organic phase was dried with magnesium sulfate and then a solvent was evaporated from the reaction product. Obtained residues were isolated and purified using silica gel chromatography to obtain 3.04 g of Intermediate A-1 (yield 55%) and the produced compound was characterized through LCMS.

LCMS ($C_{36}H_{26}BrN$): calculated 551.1; actual 552.1

Synthesis of Compound 1

Reaction Formula 5

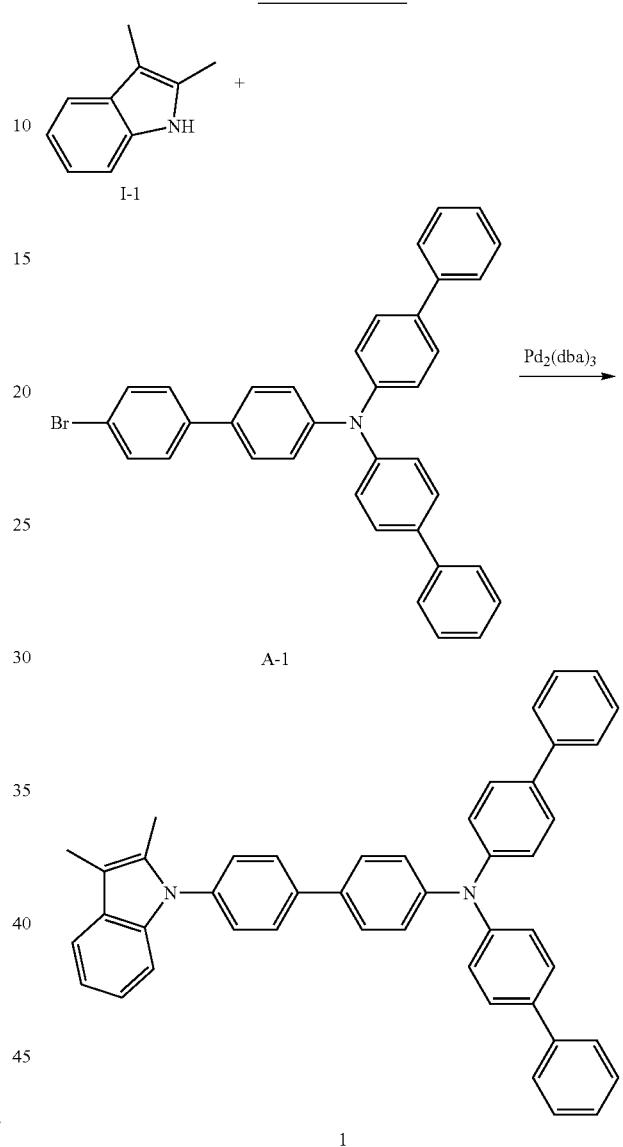

1.45 g (10.0 mmol) of Intermediate I-1, 5.52 g (10.0 mmol) of Intermediate A-1, 1.44 g (15.0 mmol) of t-BuONa, 0.14 g (0.15 mmol) of $Pd_2(dba)_3$, and 0.3 g (0.15 mmol) $(t-Bu)_3P$ were dissolved in 300 mL of toluene and then agitated at a temperature of 90° C. for three hours. After the reaction was completed, the reaction product was cooled to room temperature, distilled water was added to the reaction product, and the reaction product was extracted three times with 500 mL of diethylether to collect an organic phase. The collected organic phase was dried with magnesium sulfate and then a solvent was evaporated from the reaction product. Obtained residues were isolated and purified using silica gel chromatography to obtain 5.12 g of Intermediate Compound 1 (yield 83%) and the compound produced was characterized through LCMS and $^1$H-NMR.

LCMS ($C_{46}H_{36}N_2$): calculated 616.3; actual 617.3

¹H NMR (CDCl₃, 400 MHz) δ(ppm) 7.65-7.61 (m, 4H), 7.53-7.49 (m, 6H), 7.46-7.29 (m, 12H), 7.16 (dd, 1H), 7.13 (dd, 1H), 7.07-7.03 (m, 4H), 6.98-6.94 (m, 2H), 2.34 (s, 3H), 2.25 (s, 3H)

Synthesis of Compound 2

The same method as in the method of producing Compound 1 was used to synthesize 5.32 g of Compound 2 (yield 81%), except for using Intermediate A-2 instead of Intermediate A-1. The compound produced was characterized through LCMS and ¹H-NMR.

LCMS ($C_{49}H_{40}N_2$): calculated 656.3; actual 657.3

¹H NMR (CDCl₃, 400 MHz) δ(ppm) 7.78 (d, 1H), 7.65-7.62 (m, 2H), 7.56 (d, 1H), 7.53-7.49 (m, 4H), 7.46-7.29 (m, 10H), 7.21-7.12 (m, 3H), 7.09 (dd, 1H), 6.99 (d, 1H), 6.97-6.92 (m, 4H), 6.89 (d, 1H), 2.33 (s, 3H), 2.24 (s, 3H), 1.61 (s, 6H)

Synthesis of Compound 4

The same method as in the method of producing Compound 1 was used to synthesize 4.96 g of Compound 4 (yield 84%), except for using Intermediate A-3 instead of Intermediate A-1. The compound produced was characterized through LCMS and ¹H-NMR.

LCMS ($C_{44}H_{34}N_2$): calculated 590.3; actual 591.3

¹H NMR (CDCl₃, 400 MHz) δ(ppm) 8.17 (d, 1H), 7.87 (d, 1H), 7.64-7.61 (m, 2H), 7.56-7.29 (m, 16H), 7.23 (dd, 1H), 7.18 (dd, 1H), 7.07 (dd, 1H), 7.02-6.98 (m, 4H), 6.96 (d, 1H), 2.32 (s, 3H), 2.24 (s, 3H)

Synthesis of Compound 10

The same method as in the method of producing Compound 1 was used to synthesize 6.31 g of Compound 10 (yield 76%), except for using Intermediate A-4 instead of Intermediate A-1. The compound produced was characterized through LCMS and ¹H-NMR.

LCMS ($C_{58}H_{40}N_2S_2$): calculated 828.3; actual 829.3

¹H NMR (CDCl₃, 400 MHz) δ(ppm) 8.16 (d, 2H), 8.11 (d, 2H), 7.86 (d, 2H), 7.76 (d, 2H), 7.62-7.48 (m, 8H), 7.46-7.30 (m, 10H), 7.18 (dd, 1H), 7.09 (dd, 1H), 6.98-6.94 (m, 6H), 2.34 (s, 3H), 2.25 (s, 3H)

Synthesis of Compound 14

The same method as in the method of producing Compound 1 was used to synthesize 4.36 g of Compound 14 (yield 68%), except for using Intermediate A-5 instead of Intermediate A-1. The compound produced was characterized through LCMS and ¹H-NMR.

LCMS ($C_{47}H_{35}N_3$): calculated 641.3; actual 642.3

¹H NMR (CDCl₃, 400 MHz) δ(ppm) 7.67-7.61 (m, 6H), 7.55-7.48 (m, 6H), 7.46-7.31 (m, 9H), 7.19 (dd, 1H), 7.09 (dd, 1H), 7.02-6.98 (m, 2H), 6.92-6.88 (m, 4H), 2.33 (s, 3H), 2.24 (s, 3H)

Synthesis of Compound 16

The same method as in the method of producing Compound 1 was used to synthesize 5.85 g of Compound 16 (yield 79%), except for using Intermediate I-2 instead of Intermediate I-1. The compound produced was characterized through LCMS and ¹H-NMR.

LCMS ($C_{56}H_{40}N_2$): calculated 740.3; actual 741.3

¹H NMR (CDCl₃, 400 MHz) δ(ppm) 7.81 (d, 1H), 7.68 D, 1H), 7.65-7.61 (m, 4H), 7.57-7.49 (m, 8H), 7.47-7.27 (m, 16H), 7.20-7.16 (m, 2H), 7.08-7.02 (m, 6H), 6.96-6.92 (m, 2H)

Synthesis of Compound 17

The same method as in the method of producing Compound 1 was used to synthesize 6.41 g of Compound 17 (yield 82%), except for using Intermediate I-2 instead of Intermediate I-1 and Intermediate A-2 instead of Intermediate A-1. The compound produced was characterized through LCMS and ¹H-NMR.

LCMS ($C_{59}H_{44}N_2$): calculated 780.4; actual 781.4

¹H NMR (CDCl₃, 400 MHz) δ(ppm) 7.81 (d, 1H), 7.77 (d, 1H), 7.68 (d, 1H), 7.65-7.61 (m, 2H), 7.57-7.48 (m, 7H), 7.46-7.27 (m, 14H), 7.21-7.17 (m, 2H), 7.14-7.09 (m, 2H), 7.02-6.98 (m, 2H), 6.96 (d, 1H), 6.92-6.86 (m, 4H), 6.82 (s, 1H), 1.62 (s, 6H)

Synthesis of Compound 21

The same method as in the method of producing Compound 1 was used to synthesize 4.89 g of Compound 21 (yield 71%), except for using Intermediate I-2 instead of Intermediate I-1 and Intermediate A-6 instead of Intermediate A-1. The compound produced was characterized through LCMS and ¹H-NMR.

LCMS ($C_{51}H_{35}N_3$): calculated 689.3; actual 690.3

¹H NMR (CDCl₃, 400 MHz) δ(ppm) 7.82 (d, 1H), 7.69 (d, 1H), 7.66-7.62 (m, 2H), 7.59-7.50 (m, 6H), 7.48-7.29 (m, 15H), 7.22-7.17 (m, 2H), 7.08-7.01 (m, 6H), 6.98-6.93 (m, 2H)

Synthesis of Compound 23

The same method as in the method of producing Compound 1 was used to synthesize 6.94 g of Compound 23 (yield 81%), except for using Intermediate I-2 instead of Intermediate I-1 and Intermediate A-7 instead of Intermediate A-1. The compound produced was characterized through LCMS and ¹H-NMR.

LCMS ($C_{65}H_{48}N_2$): calculated 856.4; actual 857.4

¹H NMR (CDCl₃, 400 MHz) δ(ppm) 7.82-7.78 (m, 2H), 7.72 (d, 1H), 7.68-7.61 (m, 4H), 7.58-7.48 (m, 7H), 7.47-7.29 (m, 16H), 7.23-7.13 (m, 4H), 7.06-7.00 (m, 6H), 6.99-6.95 (m, 2H), 1.59 (s, 6H)

Synthesis of Compound 25

The same method as in the method of producing Compound 1 was used to synthesize 3.67 g of Compound 25 (yield 77%), except for using Intermediate I-2 instead of Intermediate I-1 and Intermediate A-4 instead of Intermediate A-1. The compound produced was characterized through LCMS and ¹H-NMR.

LCMS ($C_{68}H_{44}N_2S_2$): calculated 952.3; actual 953.3

¹H NMR (CDCl₃, 400 MHz) δ(ppm) 8.17 (d, 2H), 8.12 (d, 2H), 7.86 (d, 2H), 7.79 (d, 1H), 7.77 (d, 2H), 7.67 (d, 1H), 7.62-7.48 (m, 10H), 7.47-7.28 (m, 14H), 7.23-7.18 (m, 2H), 7.07-7.02 (m, 2H), 6.97-6.93 (m, 6H)

Synthesis of Compound 30

The same method as in the method of producing Compound 1 was used to synthesize 4.68 g of Compound 30 (yield 61%), except for using Intermediate I-2 instead of Intermediate I-1 and Intermediate A-8 instead of Intermediate A-1. The compound produced was characterized through LCMS and ¹H-NMR.

LCMS ($C_{56}H_{38}N_4$): calculated 766.3; actual 767.3

¹H NMR (CDCl₃, 400 MHz) δ(ppm) 8.90 (s, 1H), 8.60 (d, 1H), 7.93 (d, 1H), 7.81 (d, 1H), 7.68-7.62 (m, 5H), 7.57-7.40 (m, 12H), 7.38-7.24 (m, 7H), 7.22-7.18 (m, 2H), 7.08-7.04 (m, 2H), 7.01-6.97 (m, 2H), 6.96-6.92 (m, 4H)

Synthesis of Compound 31

The same method as in the method of producing Compound 1 was used to synthesize 3.16 g of Compound 31 (yield 80%), except for using Intermediate I-2 instead of Intermediate I-1 and Intermediate A-9 instead of Intermediate A-1. The compound produced was characterized through LCMS and ¹H-NMR.

LCMS ($C_{60}H_{42}N_2$): calculated 790.3; actual 791.3

¹H NMR (CDCl₃, 400 MHz) δ(ppm) 7.80 (d, 1H), 7.68 (d, 1H), 7.64-7.60 (m, 5H), 7.57-7.47 (m, 9H), 7.46-7.28 (m, 16H), 7.12 (d, 1H), 7.04-6.98 (m, 5H), 6.94-6.90 (m, 4H)

Synthesis of Compound 34

The same method as in the method of producing Compound 1 was used to synthesize 2.92 g of Compound 34 (yield 76%), except for using Intermediate I-2 instead of Intermediate I-1 and Intermediate A-10 instead of Intermediate A-1. The compound produced was characterized through LCMS and ¹H-NMR.

LCMS ($C_{58}H_{44}N_2$): calculated 768.4; actual 769.4

¹H NMR (CDCl₃, 400 MHz) δ(ppm) 7.69-7.60 (m, 6H), 7.58-7.49 (m, 6H), 7.46-7.26 (m, 14H), 7.21 (d, 1H), 7.16 (d, 1H), 7.09 (d, 1H), 7.04-7.00 (m, 2H), 6.98 (s, 1H), 6.96 (s, 1H), 6.94-6.90 (m, 4H), 6.86 (d, 1H), 2.38 (s, 3H), 2.26 (s, 3H)

Synthesis of Compound 36

The same method as in the method of producing Compound 1 was used to synthesize 3.01 g of Compound 36 (yield 77%), except for using Intermediate I-2 instead of Intermediate I-1 and Intermediate A-11 instead of Intermediate A-1. The compound produced was characterized through LCMS and ¹H-NMR.

LCMS ($C_{59}H_{44}N_2$): calculated 780.4; actual 781.4

¹H NMR (CDCl₃, 400 MHz) δ(ppm) 7.82 (d, 1H), 7.69 (d, 1H), 7.65-7.59 (m, 5H), 7.56-7.30 (m, 21H), 7.19 (d, 1H), 7.08-7.04 (m, 2H), 7.01 (d, 1H), 6.96-6.91 (m, 6H), 1.58 (s, 6H)

Synthesis of Compound 40

The same method as in the method of producing Compound 1 was used to synthesize 2.70 g of Compound 40 (yield 73%), except for using Intermediate I-2 instead of Intermediate I-1 and Intermediate A-12 instead of Intermediate A-1. The compound produced was characterized through LCMS and ¹H-NMR.

LCMS ($C_{56}H_{40}N_2$): calculated 740.3; actual 741.3

¹H NMR (CDCl₃, 400 MHz) δ(ppm) 7.80 (d, 1H), 7.70 (d, 1H), 7.67-7.63 (m, 4H), 7.59-7.25 (m, 25H), 7.21 (dd, 1H), 7.12-7.06 (m, 6H), 7.02-6.97 (m, 2H)

Synthesis of Compound 43

The same method as in the method of producing Compound 1 was used to synthesize 3.18 g of Compound 43 (yield 78%), except for using Intermediate I-2 instead of Intermediate I-1 and Intermediate A-13 instead of Intermediate A-1. The compound produced was characterized through LCMS and ¹H-NMR.

LCMS ($C_{62}H_{44}N_2$): calculated 816.4; actual 817.4

¹H NMR (CDCl₃, 400 MHz) δ(ppm) 7.81-7.74 (m, 3H), 7.68-7.61 (m, 7H), 7.57-7.48 (m, 6H), 7.46-7.27 (m, 18H), 7.24-7.19 (m, 2H), 7.09-7.04 (m, 6H), 6.99-6.95 (m, 2H)

Synthesis of Compound 46

The same method as in the method of producing Compound 1 was used to synthesize 3.32 g of Compound 46 (yield 84%), except for using Intermediate I-3 instead of Intermediate I-1. The compound produced was characterized through LCMS and ¹H-NMR.

LCMS ($C_{60}H_{42}N_2$): calculated 790.3; actual 791.3

¹H NMR (CDCl₃, 400 MHz) δ(ppm) 8.03 (d, 1H), 7.95 (d, 1H), 7.90 (d, 1H), 7.67-7.33 (m, 31H), 7.19-7.14 (m, 4H), 7.06-7.01 (m, 2H), 6.98-6.94 (m, 2H)

Synthesis of Compound 47

The same method as in the method of producing Compound 1 was used to synthesize 3.28 g of Compound 47 (yield 79%), except for using Intermediate I-3 instead of Intermediate I-1 and Intermediate A-2 instead of Intermediate A-1. The compound produced was characterized through LCMS and ¹H-NMR.

LCMS ($C_{63}H_{46}N_2$): calculated 830.4; actual 831.4

¹H NMR (CDCl₃, 400 MHz) δ(ppm) 8.03 (d, 1H), 7.95 (d, 1H), 7.91 (d, 1H), 7.78 (d, 1H), 7.64-7.30 (m, 26H), 7.19-7.14 (m, 2H), 7.04-7.00 (m, 3H), 6.96-6.91 (m, 4H), 6.87 (s, 1H), 1.63 (s, 6H)

Synthesis of Compound 49

The same method as in the method of producing Compound 1 was used to synthesize 3.14 g of Compound 49 (yield 82%), except for using Intermediate I-3 instead of Intermediate I-1 and Intermediate A-3 instead of Intermediate A-1. The compound produced was characterized through LCMS and ¹H-NMR.

LCMS ($C_{58}H_{40}N_2$): calculated 764.3; actual 765.3

¹H NMR (CDCl₃, 400 MHz) δ(ppm) 8.17 (d, 1H), 8.03 (d, 1H), 7.96 (d, 1H), 7.88 (d, 1H), 7.86 (d, 1H), 7.66-7.34 (m, 27H), 7.23 (dd, 1H), 7.13-7.09 (m, 4H), 7.03-6.96 (m, 3H)

Synthesis of Compound 51

The same method as in the method of producing Compound 1 was used to synthesize 3.15 g of Compound 51 (yield 77%), except for using Intermediate I-3 instead of Intermediate I-1 and Intermediate A-14 instead of Intermediate A-1. The compound produced was characterized through LCMS and ¹H-NMR.

LCMS ($C_{62}H_{46}N_2$): calculated 818.4; actual 819.4

¹H NMR (CDCl₃, 400 MHz) δ(ppm) 8.04 (d, 1H), 7.96 (d, 1H), 7.89 (d, 1H), 7.60-7.28 (m, 29H), 7.11-7.04 (m, 4H), 7.01 (s, 2H), 6.96 (d, 2H), 2.17 (s, 6H)

Synthesis of Compound 53

The same method as in the method of producing Compound 1 was used to synthesize 2.91 g of Compound 53 (yield 71%), except for using Intermediate I-3 instead of Intermediate I-1 and Intermediate A-10 instead of Intermediate A-1. The compound produced was characterized through LCMS and $^1$H-NMR.

LCMS ($C_{62}H_{46}N_2$): calculated 818.4; actual 819.4

$^1$H NMR (CDCl$_3$, 400 MHz) δ(ppm) 8.04-7.94 (m, 3H), 7.68-7.36 (m, 27H), 7.26 (d, 1H), 7.19 (d, 1H), 7.06 (s, 1H), 7.04 (d, 1H), 6.99-6.93 (m, 5H), 6.89 (dd, 1H), 2.28 (s, 3H), 2.21 (s, 3H)

Synthesis of Compound 55

The same method as in the method of producing Compound 1 was used to synthesize 3.52 g of Compound 55 (yield 80%), except for using Intermediate I-4 instead of Intermediate I-1 and Intermediate A-4 instead of Intermediate A-1. The compound produced was characterized through LCMS and $^1$H-NMR.

LCMS ($C_{62}H_{42}N_2S_2$): calculated 878.3; actual 879.3

$^1$H NMR (CDCl$_3$, 400 MHz) δ(ppm) 8.25 (d, 1H), 8.17 (d, 2H), 8.11 (d, 2H), 7.91-7.84 (m, 3H), 7.77 (d, 2H), 7.63-7.48 (m, 12H), 7.43-7.39 (m, 6H), 7.22-7.18 (m, 2H), 7.04-6.98 (m, 6H), 2.38 (s, 3H), 2.29 (s, 3H)

Synthesis of Compound 60

The same method as in the method of producing Compound 1 was used to synthesize 3.05 g of Compound 60 (yield 75%), except for using Intermediate I-3 instead of Intermediate I-1 and Intermediate A-15 instead of Intermediate A-1. The compound produced was characterized through LCMS and $^1$H-NMR.

LCMS ($C_{58}H_{45}N_3Si$): calculated 811.3; actual 812.3

$^1$H NMR (CDCl$_3$, 400 MHz) δ(ppm) 8.03 (d, 1H), 7.97 (d, 1H), 7.89 (d, 1H), 7.68-7.35 (m, 25H), 7.19-7.13 (m, 2H), 7.06-6.99 (m, 6H), 0.25 (s, 9H)

Synthesis of Compound 61

The same method as in the method of producing Compound 1 was used to synthesize 3.36 g of Compound 61 (yield 80%), except for using Intermediate I-5 instead of Intermediate I-1. The compound produced was characterized through LCMS and $^1$H-NMR.

LCMS ($C_{64}H_{44}N_2$): calculated 840.4; actual 841.4

$^1$H NMR (CDCl$_3$, 400 MHz) δ(ppm) 8.80 (d, 1H), 8.62 (d, 1H), 8.56 (d, 1H), 7.93 (d, 1H), 7.71-7.32 (m, 32H), 7.18-7.12 (m, 4H), 7.05-6.97 (m, 4H)

Synthesis of Compound 65

The same method as in the method of producing Compound 1 was used to synthesize 3.48 g of Compound 65 (yield 79%), except for using Intermediate I-5 instead of Intermediate I-1 and Intermediate A-11 instead of Intermediate A-1. The compound produced was characterized through LCMS and $^1$H-NMR.

LCMS ($C_{67}H_{48}N_2$): calculated 880.4; actual 881.4

$^1$H NMR (CDCl$_3$, 400 MHz) δ(ppm) 8.79 (d, 1H), 8.63 (d, 1H), 8.56 (d, 1H), 8.00 (d, 1H), 7.73-7.34 (m, 30H), 7.21 (s, 1H), 7.16 (d, 1H), 7.08 (s, 1H), 7.03-6.96 (m, 5H), 1.60 (s, 6H)

Synthesis of Compound 69

The same method as in the method of producing Compound 1 was used to synthesize 3.39 g of Compound 69 (yield 78%), except for using Intermediate I-5 instead of Intermediate I-1 and Intermediate A-16 instead of Intermediate A-1. The compound produced was characterized through LCMS and $^1$H-NMR.

LCMS ($C_{64}H_{42}N_2S$): calculated 870.3; actual 871.3

$^1$H NMR (CDCl$_3$, 400 MHz) δ(ppm) 8.80 (d, 1H), 8.63 (d, 1H), 8.55 (d, 1H), 8.19 (d, 1H), 8.11 (d, 1H), 7.92 (d, 1H), 7.83 (d, 1H), 7.72-7.32 (m, 27H), 7.23 (s, 1H), 7.16 (d, 1H), 7.06-6.98 (m, 4H), 6.93-6.88 (m, 2H)

Synthesis of Compound 75

The same method as in the method of producing Compound 1 was used to synthesize 2.85 g of Compound 75 (yield 72%), except for using Intermediate I-6 instead of Intermediate I-1. The compound produced was characterized through LCMS and $^1$H-NMR.

LCMS ($C_{59}H_{41}N_3$): calculated 791.3; actual 792.3

$^1$H NMR (CDCl$_3$, 400 MHz) δ(ppm) 9.02 (s, 1H), 8.42 (d, 1H), 8.13 (d, 1H), 7.82-7.74 (m, 2H), 7.67-7.61 (m, 6H), 7.57-7.31 (m, 20H), 7.19-7.06 (m, 8H), 6.99-6.92 (m, 2H)

Synthesis of Compound 77

The same method as in the method of producing Compound 1 was used to synthesize 2.89 g of Compound 77 (yield 73%), except for using Intermediate I-7 instead of Intermediate I-1. The compound produced was characterized through LCMS and $^1$H-NMR.

LCMS ($C_{59}H_{41}N_3$): calculated 791.3; actual 792.3

$^1$H NMR (CDCl$_3$, 400 MHz) δ(ppm) 8.97-8.94 (m, 2H), 8.10 (d, 1H), 7.96 (d, 1H), 7.64-7.61 (m, 4H), 7.58-7.32 (m, 25H), 7.19-7.13 (m, 6H), 7.04-6.98 (m, 2H)

Synthesis of Compound 79

The same method as in the method of producing Compound 1 was used to synthesize 3.29 g of Compound 79 (yield 77%), except for using Intermediate I-8 instead of Intermediate I-1. The compound produced was characterized through LCMS and $^1$H-NMR.

LCMS ($C_{65}H_{48}N_2$): calculated 856.4; actual 857.4

$^1$H NMR (CDCl$_3$, 400 MHz) δ(ppm) 8.19 (s, 1H), 7.94 (d, 1H), 7.65-7.62 (m, 4H), 7.53-7.35 (m, 18H), 7.33-7.20 (m, 10H), 7.12-7.04 (m, 6H), 6.99-6.92 (m, 2H), 1.62 (s, 6H)

Synthesis of Compound 81

The same method as in the method of producing Compound 1 was used to synthesize 3.16 g of Compound 81 (yield 76%), except for using Intermediate I-9 instead of Intermediate I-1. The compound produced was characterized through LCMS and $^1$H-NMR.

LCMS ($C_{62}H_{42}N_2O$): calculated 830.3; actual 831.3

$^1$H NMR (CDCl$_3$, 400 MHz) δ(ppm) 7.90 (d, 1H) 7.78-7.75 (m, 2H), 7.68-7.58 (m, 6H), 7.56-7.31 (m, 23H), 7.18-7.14 (m, 2H), 7.06-6.98 (m, 6H), 6.92-6.86 (m, 2H)

Synthesis of Compound 83

The same method as in the method of producing Compound 1 was used to synthesize 3.07 g of Compound 83 (yield 71%), except for using Intermediate I-10 instead of Intermediate I-1. The compound produced was characterized through LCMS and $^1$H-NMR.

LCMS ($C_{66}H_{44}N_2$): calculated 864.4; actual 865.4

$^1$H NMR (CDCl$_3$, 400 MHz) δ(ppm) 8.46 (d, 1H), 8.27-8.23 (m, 2H), 8.17-8.11 (m, 3H), 8.02-7.98 (m, 2H), 7.65-

7.56 (m, 6H), 7.53-7.47 (m, 10H), 7.44-7.29 (m, 12H), 7.12-7.04 (m, 4H), 7.01-6.96 (m, 2H), 6.92-6.86 (m, 2H)

Example 1

As an anode, a Corning 15 Ω/cm² (1200 Å) ITO glass substrate was cut into a size of 50 mm×50 mm×0.7 mm, and the ITO glass substrate was ultrasonically washed using isopropyl alcohol and distilled water for 5 minutes, followed by irradiation of UV and exposure to ozone for cleaning for about 30 minutes. The ITO glass substrate was then loaded onto a vacuum deposition device.

4,4',4''-tris(2-naphthyl(phenyl)amino)triphenylamine (2-TNATA) was vacuum deposited on the ITO glass substrate to form an HIL having a thickness of 600 Å, and Compound 10 was vacuum deposited on the HIL to form an HTL having a thickness of 300 Å.

9,10-di-naphthalene-2-yl-anthracene (ADN, fluorescent host) and 4,4'-bis[2-(4-N,N-diphenylamino)phenyl]vinyl]biphenyl (DPABVi, dopant) were vacuum co-deposited in a weight ratio of 98:2 to form an EML having a thickness of 300 Å.

Alq₃ was vacuum deposited on the EML to form an ETL having a thickness of 300 Å, LiF was vacuum deposited on the ETL to form an EIL having a thickness of 10 Å, and Al was vacuum deposited on the EIL to form a second electrode (cathode) having a thickness of 3000 Å to manufacture an organic light emitting diode.

Example 2

An organic light emitting diode was manufactured in the same manner as in Example 1, except for using Compound 16 instead of Compound 10 when forming an HTL.

Example 3

An organic light emitting diode was manufactured in the same manner as in Example 1, except for using Compound 30 instead of Compound 10 when forming an HTL.

Example 4

An organic light emitting diode was manufactured in the same manner as in Example 1, except for using Compound 43 instead of Compound 10 when forming an HTL.

Example 5

An organic light emitting diode was manufactured in the same manner as in Example 1, except for using Compound 47 instead of Compound 10 when forming an HTL.

Example 6

An organic light emitting diode was manufactured in the same manner as in Example 1, except for using Compound 51 instead of Compound 10 when forming an HTL.

Example 7

An organic light emitting diode was manufactured in the same manner as in Example 1, except for using Compound 53 instead of Compound 10 when forming an HTL.

Example 8

An organic light emitting diode was manufactured in the same manner as in Example 1, except for using Compound 69 instead of Compound 10 when forming an HTL.

Example 9

An organic light emitting diode was manufactured in the same manner as in Example 1, except for using Compound 77 instead of Compound 10 when forming an HTL.

Example 10

An organic light emitting diode was manufactured in the same manner as in Example 1, except for using Compound 81 instead of Compound 10 when forming an HTL.

Example 11

As an anode, a Corning 15 Ω/cm² (1200 Å) ITO glass substrate was cut into a size of 50 mm×50 mm×0.7 mm, and the ITO glass substrate was ultrasonically washed using isopropyl alcohol and distilled water for 5 minutes, followed by irradiation of UV and exposure to ozone for cleaning for about 30 minutes. The ITO glass substrate was then loaded onto a vacuum deposition device.

4,4',4''-tris(2-naphthyl(phenyl)amino)triphenylamine (2-TNATA) was vacuum deposited on the ITO glass substrate to form an HIL having a thickness of 550 Å, and 4,4'-bis[N-(1-naphthyl)-N-phenyl amino]biphenyl (NPB) was vacuum deposited on the HIL when forming a first hole transporting layer having a thickness of 250 Å. Compound 10 was vacuum deposited on the first hole transporting layer to form a second hole transporting layer having a thickness of 100 Å. 9,10-di-naphthalene-2-yl-anthracene (ADN, a fluorescent host) and 4,4'-bis[2-(4-N,N-diphenylamino)phenyl]vinyl]biphenyl (DPABVi, a dopant) were vacuum co-deposited in a weight ratio of 98:2 to form an EML having a thickness of 300 Å. Alq₃ was vacuum deposited on the EML to form an ETL having a thickness of 300 Å, LiF was vacuum deposited on the ETL to form an EIL having a thickness of 10 Å, and Al was vacuum deposited on the EIL to form a second electrode (cathode) having a thickness of 3000 Å to manufacture an organic light emitting diode.

Example 12

An organic light emitting diode was manufactured in the same manner as in Example 11, except for using Compound 16 instead of Compound 10 when forming the second hole transporting layer.

Example 13

An organic light emitting diode was manufactured in the same manner as in Example 11, except for using Compound 30 instead of Compound 10 when forming the second hole transporting layer.

Example 14

An organic light emitting diode was manufactured in the same manner as in Example 11, except for using Compound 43 instead of Compound 10 when forming the second hole transporting layer.

Example 15

An organic light emitting diode was manufactured in the same manner as in Example 11, except for using Compound 47 instead of Compound 10 when forming the second hole transporting layer.

Example 16

An organic light emitting diode was manufactured in the same manner as in Example 11, except for using Compound 51 instead of Compound 10 when forming the second hole transporting layer.

Example 17

An organic light emitting diode was manufactured in the same manner as in Example 11, except for using Compound 53 instead of Compound 10 when forming the second hole transporting layer.

Example 18

An organic light emitting diode was manufactured in the same manner as in Example 11, except for using Compound 69 instead of Compound 10 when forming the second hole transporting layer.

Example 19

An organic light emitting diode was manufactured in the same manner as in Example 11, except for using Compound 77 instead of Compound 10 when forming the second hole transporting layer.

Example 20

An organic light emitting diode was manufactured in the same manner as in Example 11, except for using Compound 81 instead of Compound 10 when forming the second hole transporting layer.

Example 21

As an anode, a Corning 15 Ω/cm² (1200 Å) ITO glass substrate was cut into a size of 50 mm×50 mm×0.7 mm, and the ITO glass substrate was ultrasonically washed using isopropyl alcohol and distilled water for 5 minutes, followed by irradiation of UV and exposure to ozone for cleaning for about 30 minutes. The ITO glass substrate was then loaded onto a vacuum deposition device.

4,4',4"-tris(2-naphthyl(phenyl)amino)triphenylamine (2-TNATA) was vacuum deposited on the ITO glass substrate to form an HIL having a thickness of 550 Å, and Compound 47 was vacuum deposited on the HIL to form a first hole transporting layer in a thickness of 250 Å. Compound 16 was vacuum deposited on the first hole transporting layer to form a second hole transporting layer having a thickness of 100 Å.

9,10-di-naphthalene-2-yl-anthracene (ADN, a fluorescent host) and 4,4'-bis[2-(4-N,N-diphenylamino)phenyl]vinyl]biphenyl (DPABVi, a dopant) were vacuum co-deposited in a weight ratio of 98:2 to form an EML having a thickness of 300 Å.

Alq₃ was vacuum deposited on the EML to form an ETL having a thickness of 300 Å, LiF was vacuum deposited on the ETL to form an EIL having a thickness of 10 Å, and Al was vacuum deposited on the EIL to form a second electrode (cathode) having a thickness of 3000 Å to manufacture an organic light emitting diode.

Example 22

An organic light emitting diode was manufactured in the same manner as in Example 21, except for using Compound 43 instead of Compound 16 when forming a second hole transporting layer.

Example 23

An organic light emitting diode was manufactured in the same manner as in Example 21, except for using Compound 53 instead of Compound 16 when forming a second hole transporting layer.

Example 24

An organic light emitting diode was manufactured in the same manner as in Example 21, except for using Compound 69 instead of Compound 16 when forming a second hole transporting layer.

Example 25

An organic light emitting diode was manufactured in the same manner as in Example 21, except for using Compound 81 instead of Compound 47 when forming a first hole transporting layer and using Compound 81 instead of Compound 16 when forming a second hole transporting layer.

Example 26

An organic light emitting diode was manufactured in the same manner as in Example 21, except for using Compound 81 instead of Compound 47 when forming a first hole transporting layer and using Compound 43 instead of Compound 16 when forming a second hole transporting layer.

Example 27

An organic light emitting diode was manufactured in the same manner as in Example 21, except for using Compound 81 instead of Compound 47 when forming a first hole transporting layer and using Compound 53 instead of Compound 16 when forming a second hole transporting layer.

Example 28

An organic light emitting diode was manufactured in the same manner as in Example 21, except for using Compound 81 instead of Compound 47 when forming a first hole transporting layer and using Compound 69 instead of Compound 16 when forming a second hole transporting layer.

Comparative Example 1

An organic light emitting diode was manufactured in the same manner as in Example 1, except for using NPB instead of Compound 10 when forming an HTL.

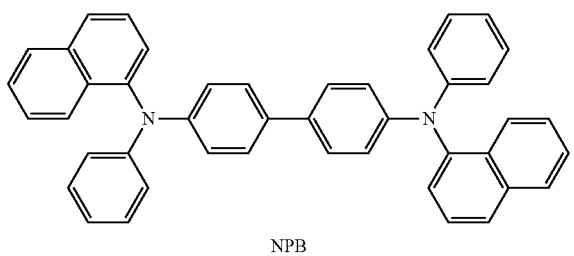 [SMILES: c1ccc(N(c2ccc(-c3ccc(N(c4ccccc4)c4cccc5ccccc45)cc3)cc2)c2cccc3ccccc23)cc1 ; "NPB"]

NPB

Comparative Example 2

An organic light emitting diode was manufactured in the same manner as in Example 1, except for using Compound A instead of Compound 10 when forming an HTL.

Comparative Example 3

An organic light emitting diode was manufactured in the same manner as in Example 1, except for using Compound B instead of Compound 10 when forming an HTL.

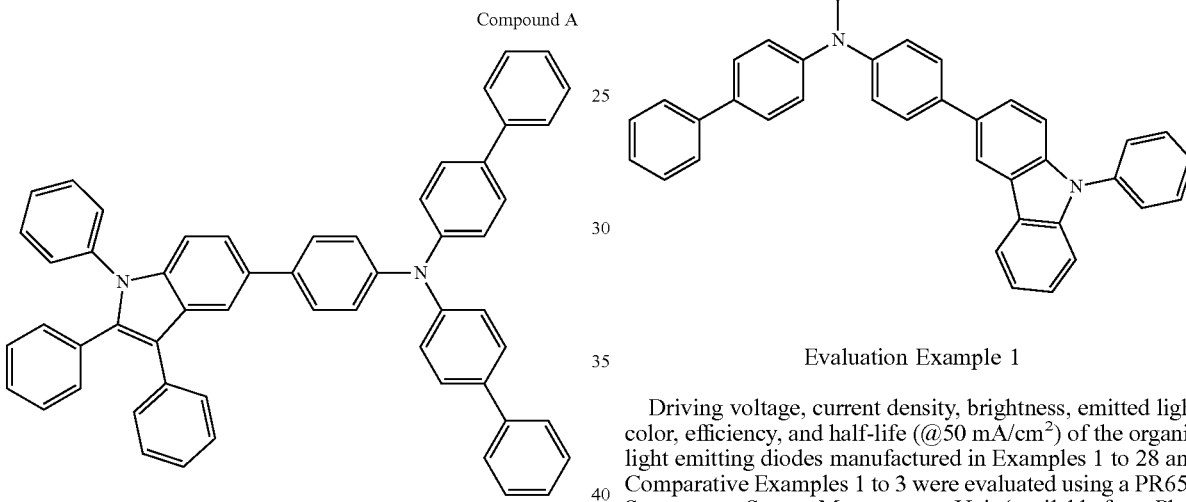

Compound A

Compound B

Evaluation Example 1

Driving voltage, current density, brightness, emitted light color, efficiency, and half-life (@50 mA/cm$^2$) of the organic light emitting diodes manufactured in Examples 1 to 28 and Comparative Examples 1 to 3 were evaluated using a PR650 Spectroscan Source Measurement Unit (available from PhotoResearch). The results are as shown in Tables 2 to 4 below:

TABLE 2

| | Hole transporting layer material | Driving voltage (V) | Current density (mA/cm$^2$) | Brightness (cd/m$^2$) | Efficiency (cd/A) | Emitted light color | Half life (hr @ 50 mA/cm$^2$) |
|---|---|---|---|---|---|---|---|
| Comparative Example 1 | NPB | 7.35 | 50 | 2065 | 4.13 | Blue | 145 |
| Comparative Example 2 | Compound A | 6.46 | 50 | 2485 | 4.97 | Blue | 212 |
| Comparative Example 3 | Compound B | 6.63 | 50 | 2185 | 4.37 | Blue | 194 |
| Example 1 | Compound 10 | 6.26 | 50 | 2620 | 5.24 | Blue | 207 |
| Example 2 | Compound 16 | 6.44 | 50 | 2595 | 5.19 | Blue | 226 |
| Example 3 | Compound 30 | 6.12 | 50 | 2535 | 5.07 | Blue | 267 |
| Example 4 | Compound 43 | 6.27 | 50 | 2610 | 5.22 | Blue | 245 |
| Example 5 | Compound 47 | 5.67 | 50 | 2710 | 5.42 | Blue | 292 |
| Example 6 | Compound 51 | 5.88 | 50 | 2560 | 5.12 | Blue | 254 |
| Example 7 | Compound 53 | 5.89 | 50 | 2570 | 5.14 | Blue | 266 |

TABLE 2-continued

|  | Hole transporting layer material | Driving voltage (V) | Current density (mA/cm$^2$) | Brightness (cd/m$^2$) | Efficiency (cd/A) | Emitted light color | Half life (hr @ 50 mA/cm$^2$) |
|---|---|---|---|---|---|---|---|
| Example 8 | Compound 69 | 6.48 | 50 | 2605 | 5.21 | Blue | 243 |
| Example 9 | Compound 77 | 6.29 | 50 | 2495 | 4.99 | Blue | 227 |
| Example 10 | Compound 81 | 5.71 | 50 | 2675 | 5.35 | Blue | 296 |

TABLE 3

|  | Second hole transporting layer material | Driving voltage (V) | Current density (mA/cm$^2$) | Brightness (cd/m$^2$) | Efficiency (cd/A) | Emitted light color | Half life (hr @ 50 mA/cm$^2$) |
|---|---|---|---|---|---|---|---|
| Example 11 | Compound 10 | 6.46 | 50 | 2995 | 5.99 | Blue | 221 |
| Example 12 | Compound 16 | 6.64 | 50 | 3145 | 6.29 | Blue | 217 |
| Example 13 | Compound 30 | 6.52 | 50 | 2845 | 5.69 | Blue | 235 |
| Example 14 | Compound 43 | 6.47 | 50 | 8160 | 6.32 | Blue | 236 |
| Example 15 | Compound 47 | 6.37 | 50 | 2925 | 5.85 | Blue | 261 |
| Example 16 | Compound 51 | 6.68 | 50 | 2865 | 5.73 | Blue | 235 |
| Example 17 | Compound 53 | 6.69 | 50 | 3210 | 6.42 | Blue | 242 |
| Example 18 | Compound 69 | 6.58 | 50 | 3170 | 6.34 | Blue | 219 |
| Example 19 | Compound 77 | 6.69 | 50 | 2945 | 5.89 | Blue | 226 |
| Example 20 | Compound 81 | 6.31 | 50 | 2830 | 5.66 | Blue | 274 |

TABLE 4

|  | First hole transporting layer Second hole transporting layer | Driving voltage (V) | Current density (mA/cm$^2$) | brightness (cd/m$^2$) | Efficiency (cd/A) | Emitted light color | Half life (hr @ 50 mA/cm$^2$) |
|---|---|---|---|---|---|---|---|
| Example 21 | Compound 47 Compound 16 | 5.46 | 50 | 3410 | 6.82 | Blue | 289 |
| Example 22 | Compound 47 Compound 43 | 5.47 | 50 | 3395 | 6.79 | Blue | 294 |
| Example 23 | Compound 47 Compound 53 | 5.52 | 50 | 3425 | 6.85 | Blue | 308 |
| Example 24 | Compound 47 Compound 69 | 5.57 | 50 | 3360 | 6.72 | Blue | 263 |
| Example 25 | Compound 81 Compound 16 | 5.53 | 50 | 3440 | 6.88 | Blue | 321 |

TABLE 4-continued

| | First hole transporting layer Second hole transporting layer | Driving voltage (V) | Current density (mA/cm$^2$) | brightness (cd/m$^2$) | Efficiency (cd/A) | Emitted light color | Half life (hr @ 50 mA/cm$^2$) |
|---|---|---|---|---|---|---|---|
| Example 26 | Compound 81 Compound 43 | 5.61 | 50 | 3480 | 6.96 | Blue | 341 |
| Example 27 | Compound 81 Compound 53 | 5.49 | 50 | 3415 | 6.83 | Blue | 317 |
| Example 28 | Compound 81 Compound 69 | 5.48 | 50 | 3395 | 6.79 | Blue | 266 |

According to Tables 2 to 4 above, the organic light emitting diodes in Examples 1 to 28 showed improved driving voltage, excellent I-V-L characteristics and improved efficiencies than the organic light emitting diodes of Comparative Examples 1 to 3.

More specifically, the organic light emitting diodes of Examples 11 to 20 showed a substantial improvement in efficiency compared to the organic light emitting diodes of Comparative Examples 1 to 3 in which the second hole transporting layers were not used.

The arylamine-based compound represented by Formula 1 above lowers a hole transport barrier to decrease the driving voltage of an organic light emitting diode and has greater triplet energy than an EML material, thereby preventing diffusion of excitons produced in the EML into other layers and therefore increases the efficiency of the organic light emitting diode.

While the present invention has been particularly shown and described with reference to exemplary embodiments thereof, it will be understood by those of ordinary skill in the art that various changes in form and details may be made therein without departing from the spirit and scope of the present invention as defined by the following claims, and equivalents thereof.

What is claimed is:

1. An arylamine-based compound represented by Formula 1 below:

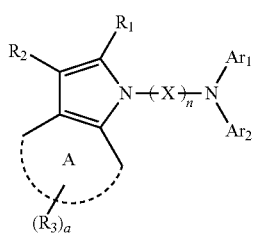

Formula 1 wherein in Formula 1,
ring A is selected from: benzene, naphthalene, anthracene, fluorene, spiro-fluorene, phenanthrene, triphenylene, chrysene, naphthacene, perylene, pyrrole, imidazole, pyrazole, pyridine, pyrazine, pyrimidine, pyridazine, isoindole, indole, quinoline, isoquinoline, benzoquinoline, naphthyridine, quinoxaline, quinazoline, cinnoline, carbazole, phenanthridine, acridine, phenanthroline, phenazine, benzoxazole, benzimidazole, furan, benzofuran, thiophene, benzothiophene, thiazole, isothiazole, benzothiazole, isoxazole, oxazole, triazole, tetrazole, oxadiazole, triazine, dibenzofuran, dibenzothiophene, or benzocarbazole;

$(X)_n$ is selected from Formulae 3a to 3n below:

<3a>

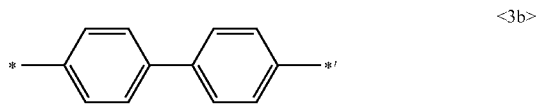
<3b>

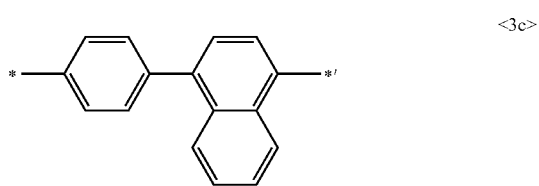
<3c>

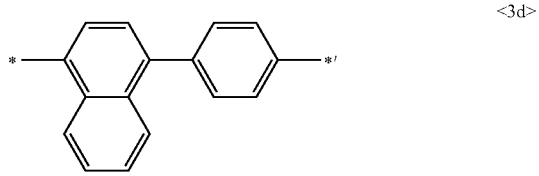
<3d>

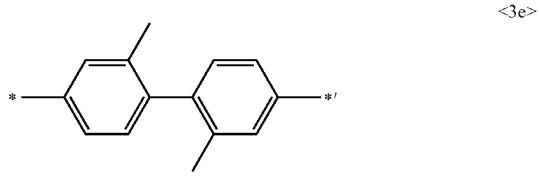
<3e>

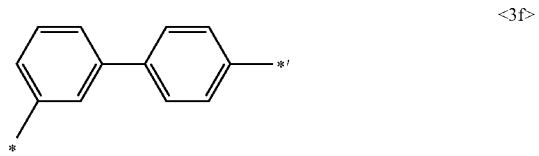
<3f>

-continued

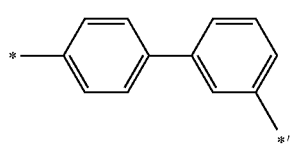
<3g>

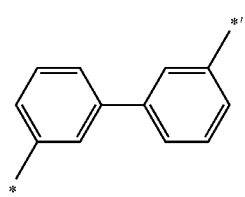
<3h>

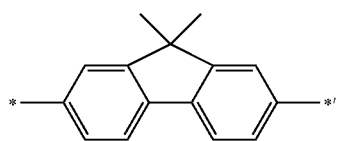
<3i>

<3j>

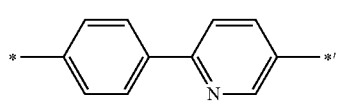
<3k>

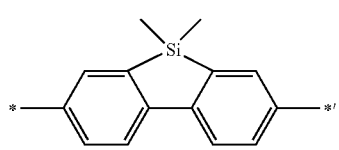
<3l>

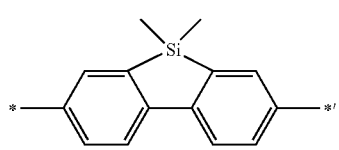
<3m>

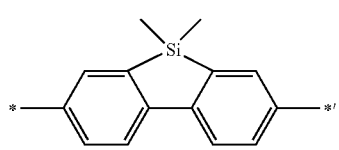
<3n> wherein in Formulae 3a to 3n, * is a binding site to the nitrogen atom of a pyrrole ring in Formula 1 and *' is a binding site to the other nitrogen atom;

each of $Ar_1$ and $Ar_2$ is independently selected from: a substituted or unsubstituted $C_6$-$C_{30}$ aryl group or a substituted or unsubstituted $C_2$-$C_{30}$ heteroaryl group;

each of $R_1$, and $R_2$ is independently selected from: a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or a substituted or unsubstituted $C_2$-$C_{30}$ heteroaryl group;

each of $R_3$ is independently a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or an unsubstituted $C_2$-$C_{30}$ heteroaryl group; and a is an integer of 0 to 4.

2. The arylamine-based compound of claim 1, wherein the ring A is selected from: benzene, naphthylene, fluorene, phenanthrene, chrysene, perylene, pyridine, pyrazine, pyrimidine, quinoline, isoquinoline, benzoquinoline, carbazole, phenanthroline, dibenzofuran, or dibenzothiophene.

3. The arylamine-based compound of claim 1, wherein the ring A is any one of Formulae 2a to 2m below:

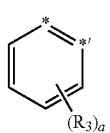
<2a>

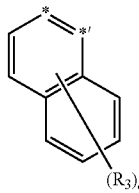
<2b>

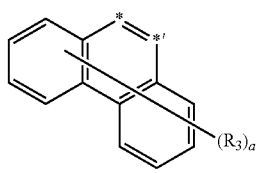
<2c>

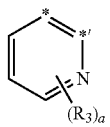
<2d>

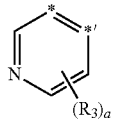
<2e>

-continued

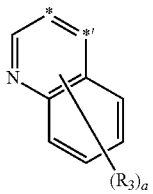 <2f>

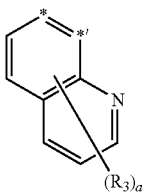 <2g>

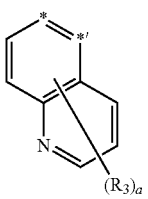 <2h>

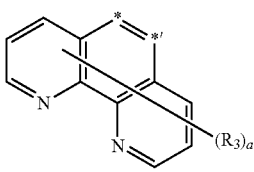 <2i>

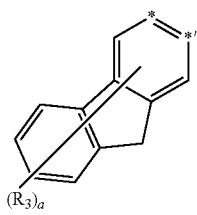 <2j>

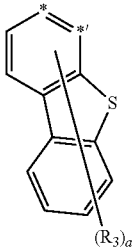 <2k>

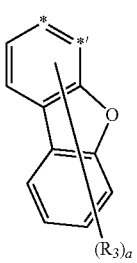 <2l>

-continued

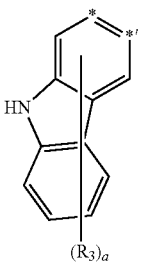 <2m>

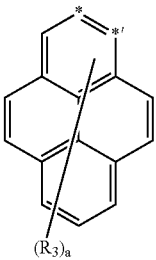 <2n>

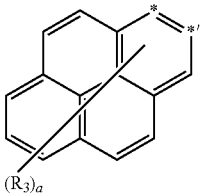 <2o> wherein in Formulae 2a to 2m,
* corresponds to carbon number 4 of a pyrrole ring in Formula 1 and *' corresponds to carbon number 5 of a pyrrole ring in Formula 1.

4. The arylamine-based compound of claim 1, wherein each of $Ar_1$ and $Ar_2$ is independently selected from:
   i) a phenyl group, a naphthyl group, an anthryl group, a fluorenyl group, a benzofuranyl group, a benzothienyl group, a benzosilolyl group, a dibenzofuranyl group, a dibenzothienyl group, or a dibenzosilolyl group; or
   ii) a phenyl group, a naphthyl group, an anthryl group, a fluorenyl group, a benzofuranyl group, a benzothienyl group, a benzosilolyl group, a dibenzofuranyl group, a dibenzothienyl group, or a dibenzosilolyl group, each substituted with at least one of:
      a deuterium atom; a halogen atom; a hydroxyl group; a cyano group; a nitro group; an amino group; an amidino group; a hydrazine group; a hydrazone group; a carboxylic acid group or a salt thereof; a sulfonic acid group or a salt thereof; a phosphoric acid group or a salt thereof; a $C_1$-$C_{10}$ alkyl group; —Si($Q_3$)($Q_4$)($Q_5$) wherein each of $Q_3$ to $Q_5$ is independently a $C_1$-$C_{10}$ alkyl group; a $C_1$-$C_{10}$ alkyl group substituted with at least one of: a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or —Si($Q_3$)($Q_4$)($Q_5$) wherein each of $Q_3$ to $Q_5$ is independently a $C_1$-$C_{10}$ alkyl group; a $C_6$-$C_{16}$ aryl group; a $C_2$-$C_{16}$ heteroaryl group; or a $C_6$-$C_{16}$ aryl group or a $C_2$-$C_{16}$ heteroaryl group, each substituted with a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, a $C_2$-$C_{16}$ heteroaryl group, or $Si(Q_3)(Q_4)(Q_5)$ wherein each of $Q_3$ to $Q_5$ is independently a $C_1$-$C_{10}$ alkyl group.

5. The arylamine-based compound of claim 1, wherein each of $Ar_1$ and $Ar_2$ is independently selected from:
i) a phenyl group, a naphthyl group, a fluorenyl group, a dibenzothienyl group, or a dibenzosilolyl group; or
ii) a phenyl group, a naphthyl group, a fluorenyl group, a dibenzothienyl group, or a dibenzosilolyl group, each substituted with at least one of: a deuterium atom; a fluorine atom; a cyano group; a nitro group; a methyl group; an ethyl group; an n-propyl group; an iso-propyl group; an n-butyl group; a sec-butyl group; an iso-butyl group; a tert-butyl group; —$Si(Q_3)(Q_4)(Q_5)$ wherein each of $Q_3$ to $Q_5$ is independently a methyl group, an ethyl group, an n-propyl group, an iso-propyl group, an n-butyl group, a sec-butyl group, an iso-butyl group, or a tert-butyl group; a methyl group, an ethyl group, an n-propyl group, an iso-propyl group, an n-butyl group, a sec-butyl group, an iso-butyl group, or a tert-butyl group, each substituted with at least one of: a deuterium atom, a fluorine atom, a cyano group, a nitro group, or —$Si(Q_3)(Q_4)(Q_5)$ wherein each of $Q_3$ to $Q_5$ is independently a methyl group, an ethyl group, an n-propyl group, an iso-propyl group, an n-butyl group, a sec-butyl group, an iso-butyl group, or a tert-butyl group; a phenyl group; a naphthyl group; an anthracenyl group; a fluorenyl group; a benzothienyl group; a dibenzothienyl group; a pyridyl group; a pyrimidyl group; a triazinyl group; a carbazolyl group; or a phenyl group, a naphthyl group, an anthracenyl group, a fluorenyl group, a benzothienyl group, a dibenzothienyl group, a pyridyl group, a pyrimidyl group, a triazinyl group, or a carbazolyl group, each substituted with a deuterium atom, a fluorine atom, a cyano group, a nitro group, a methyl group, an ethyl group, an n-propyl group, an iso-propyl group, an n-butyl group, a sec-butyl group, an iso-butyl group, a tert-butyl group, a phenyl group, a naphthyl group, an anthracenyl group, a fluorenyl group, a benzothienyl group, a dibenzothienyl group, a pyridyl group, a pyrimidyl group, a triazinyl group, a carbazolyl group, or —$Si(Q_3)(Q_4)(Q_5)$ wherein each of $Q_3$ to $Q_5$ is independently a methyl group, an ethyl group, an n-propyl group, an iso-propyl group, an n-butyl group, a sec-butyl group, an iso-butyl group, or a tert-butyl group.

6. The arylamine-based compound of claim 1, wherein each of $Ar_1$ and $Ar_2$ is independently selected from:
i) a phenyl group, a naphthyl group, a fluorenyl group, a dibenzothienyl group, or a dibenzosilolyl group; or
ii) a phenyl group, a naphthyl group, a fluorenyl group, a dibenzothienyl group, or a dibenzosilolyl group, each substituted with at least one of: a deuterium atom; a fluorine atom; a cyano group; a nitro group; —$Si(CH_3)_3$; a methyl group; a methyl group substituted with at least one of: a deuterium atom, a fluorine atom, a cyano group, a nitro group or —$Si(CH_3)_3$; a phenyl group; a fluorenyl group; a dibenzothienyl group; a pyridyl group; or a phenyl group, a fluorenyl group, a dibenzothienyl group, or a pyridyl group, each substituted with at least one of: a deuterium atom, a fluorine atom, a cyano group, a nitro group, —$Si(CH_3)_3$, a methyl group, or a phenyl group.

7. The arylamine-based compound of claim 1, wherein each of $Ar_1$ and $Ar_2$ is independently any one of Formulae 4a to 4s:

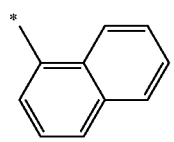
<4a>

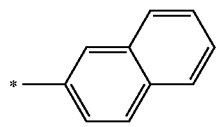
<4b>

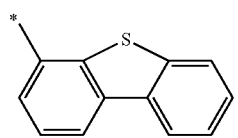
<4c>

<4d>

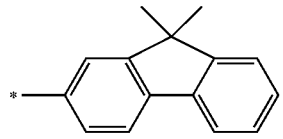
<4e>

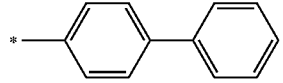
<4f>

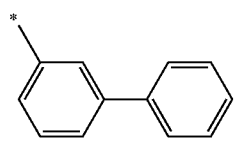
<4g>

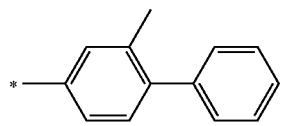
<4h>

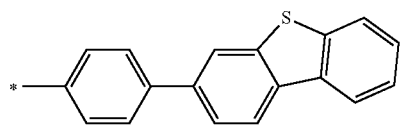
<4i>

-continued

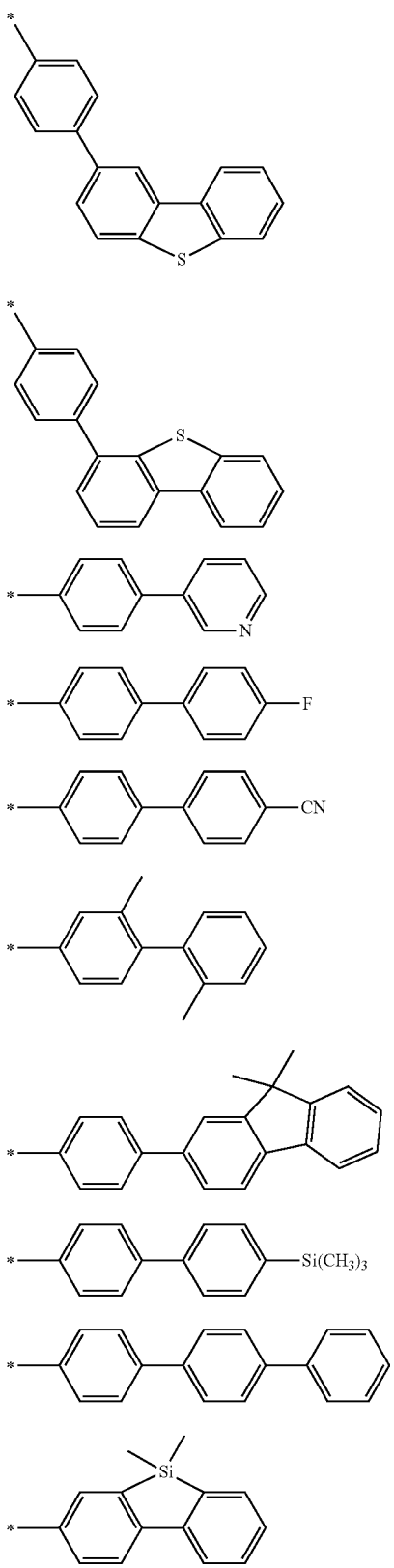

wherein in Formulae 4a to 4s,
is a binding site to the nitrogen atom.

8. The arylamine-based compound of claim 1, wherein each of $R_1$, $R_2$ and each of $R_3$ is independently selected from:

a methyl group, an ethyl group, an n-propyl group, an iso-propyl group, an n-butyl group, a sec-butyl group, an iso-butyl group, a tert-butyl group, a phenyl group, a naphthyl group, an anthracenyl group, or a fluorenyl group.

9. An organic light emitting diode comprising: a first electrode;
a second electrode facing the first electrode; and an organic layer between the first electrode and the second electrode, and comprising an emission layer;
wherein the organic layer comprises a hole transporting layer between the first electrode and the emission layer; wherein the hole transporting layer between the first electrode and the emission layer comprises a first hole transporting layer and a second hole transporting layer, wherein the second hole transporting layer is between the first hole transporting layer and the emission layer, and the second hole transporting layer comprises the arylamine-based compound of Formula 1.

10. The organic light emitting diode of claim 9, wherein the second hole transporting layer comprises a first arylamine-based compound of Formula 1 and the first hole transporting layer comprises a second arylamine-based compound of Formula 1, and
the first arylamine-based compound of Formula 1 is the same as or different from the second arylamine-based compound of Formula 1.

11. The arylamine-based compound of claim 1, wherein the arylamine-based compound of Formula 1 is a compound selected from the group consisting of Compounds 1 to 82 below:

1

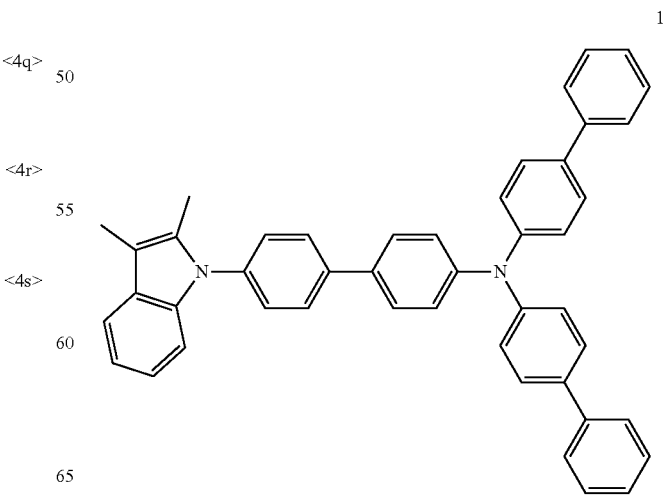

-continued
2
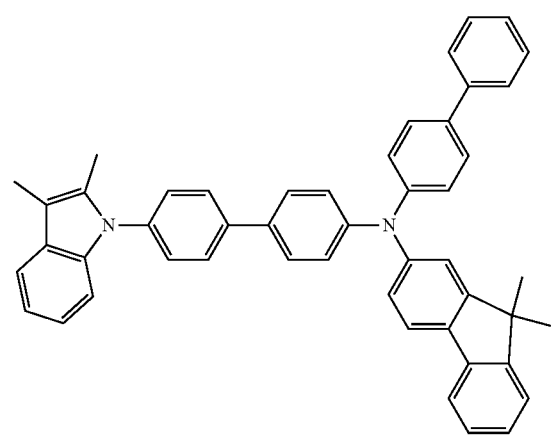
3
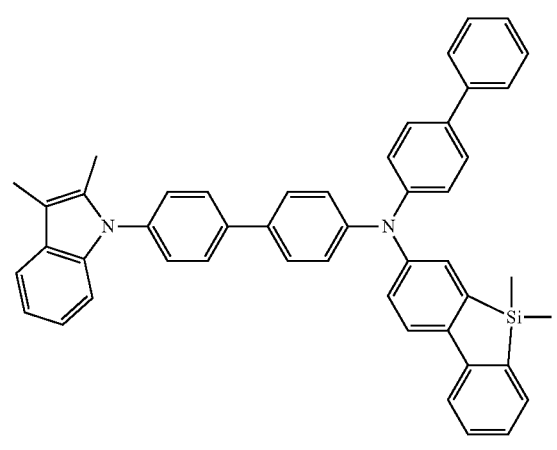
4
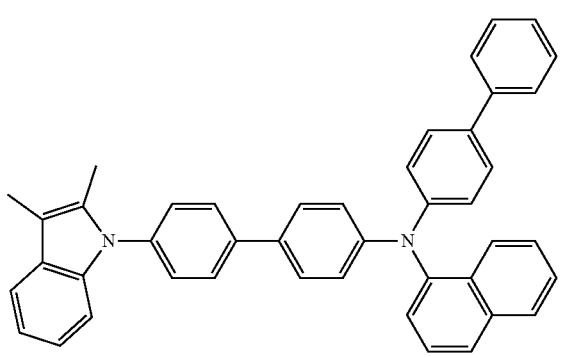
5
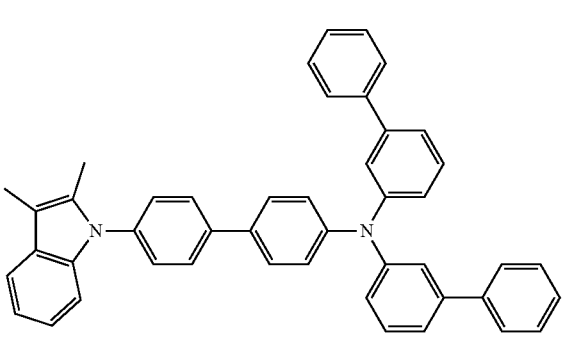
-continued
6
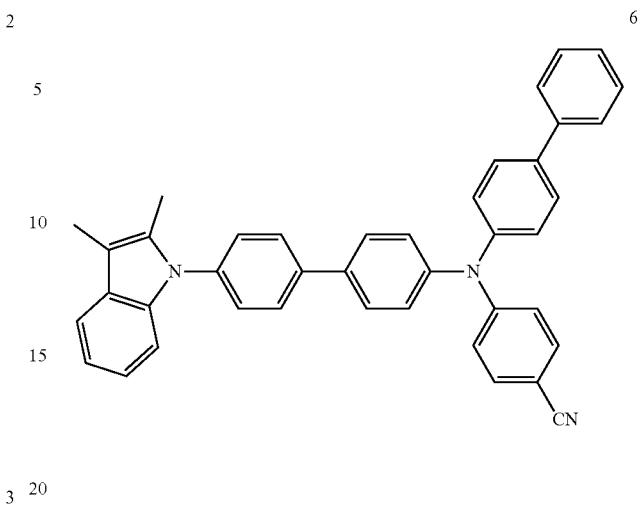
7
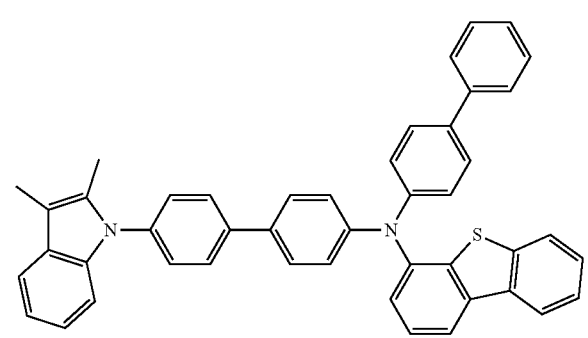
8
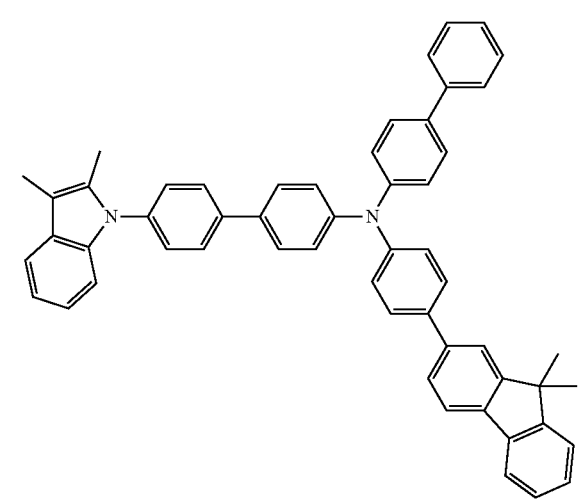

-continued
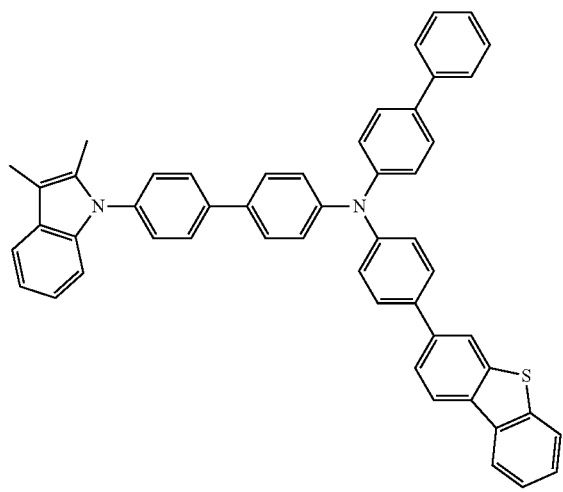
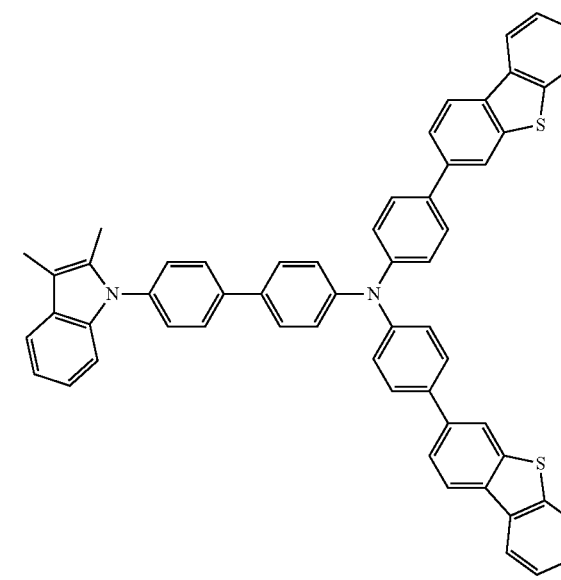
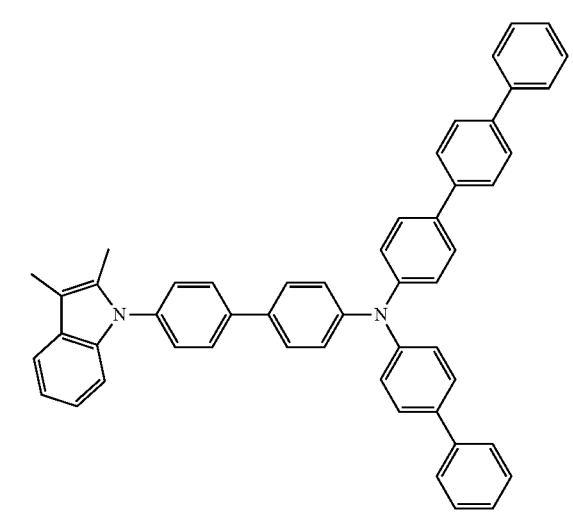
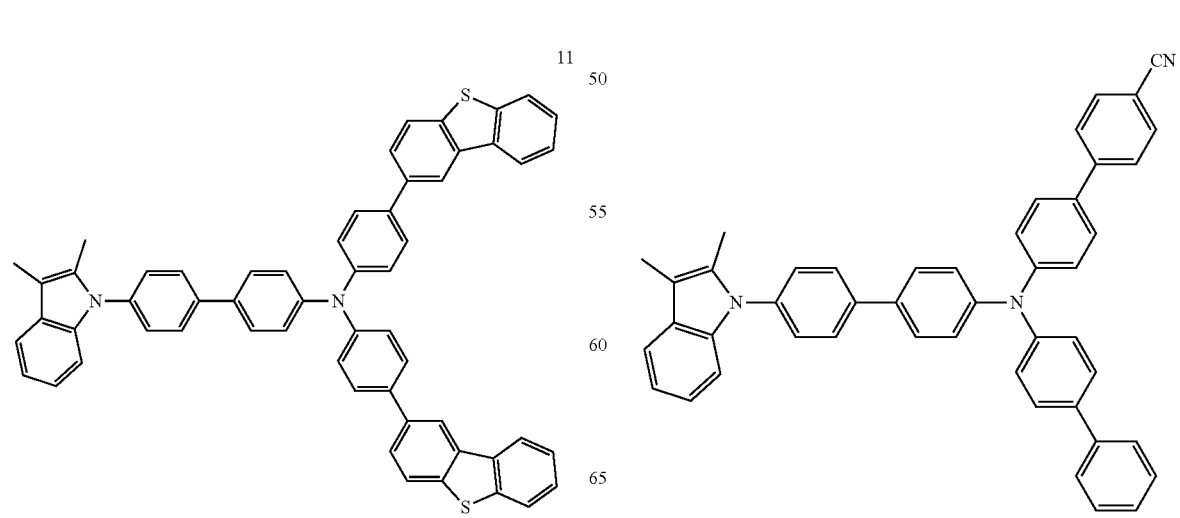

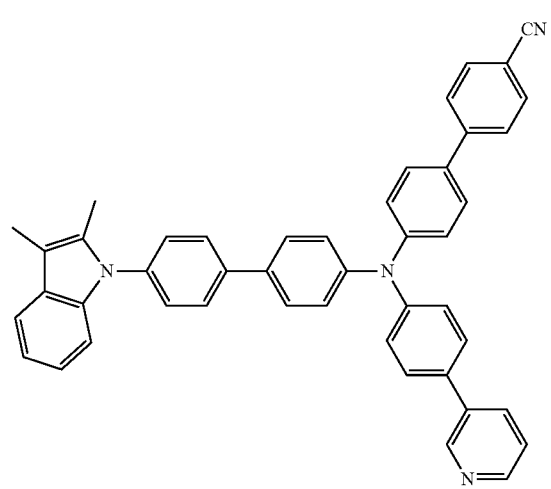
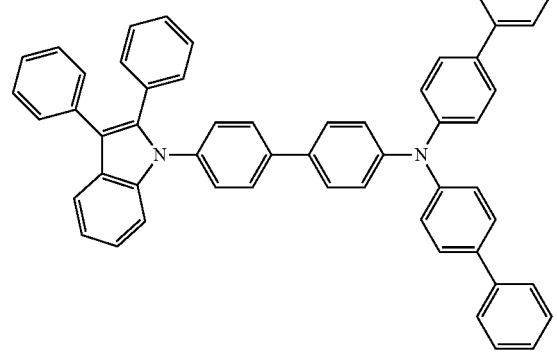
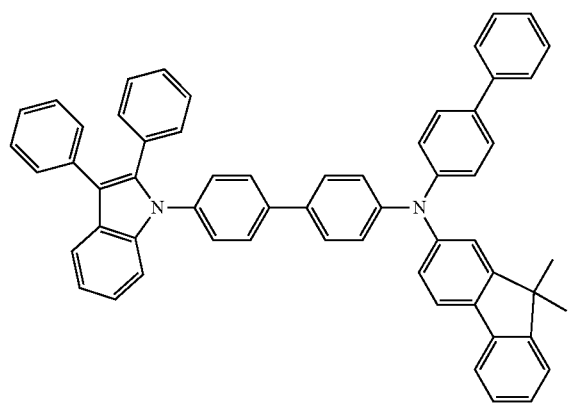
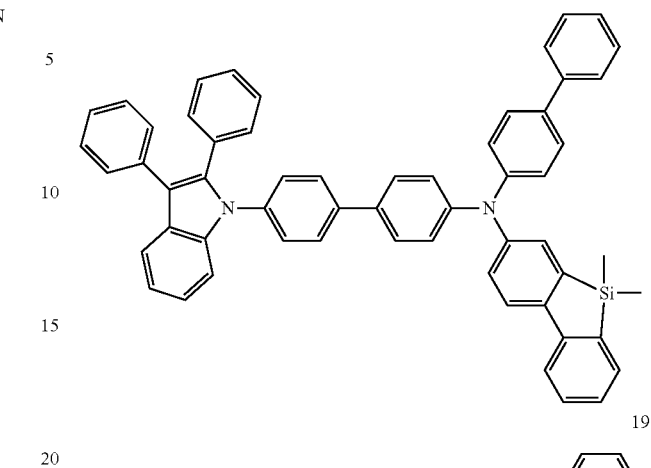
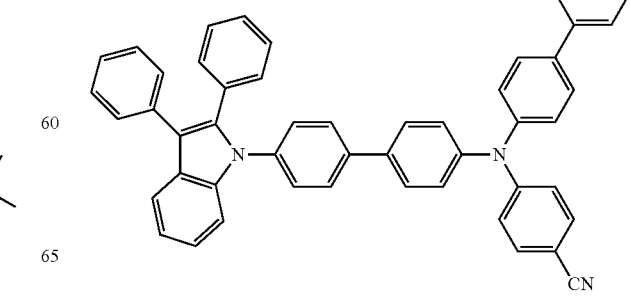

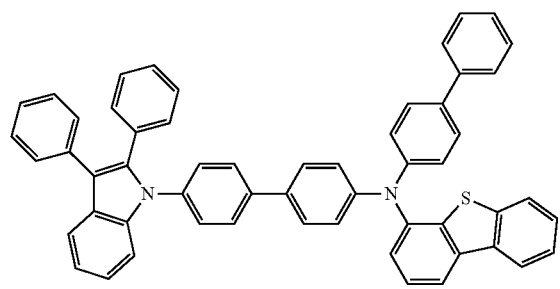
22
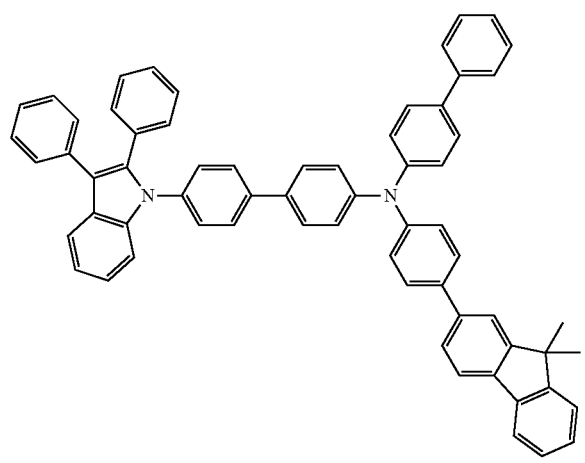
23
24
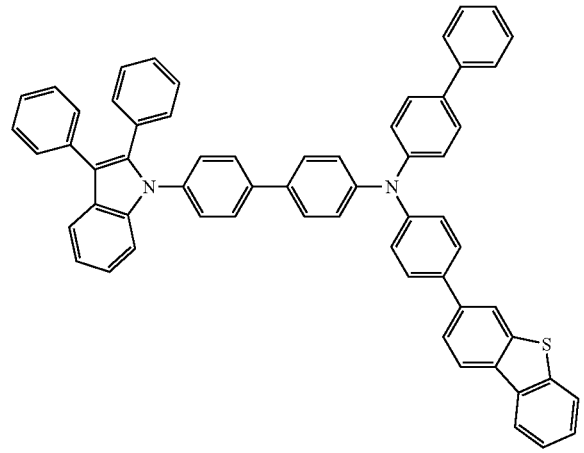
25
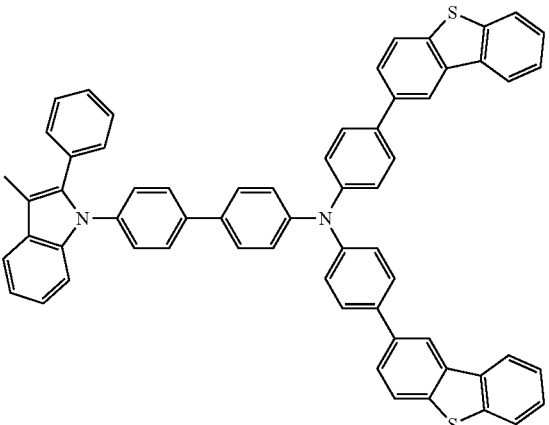
26
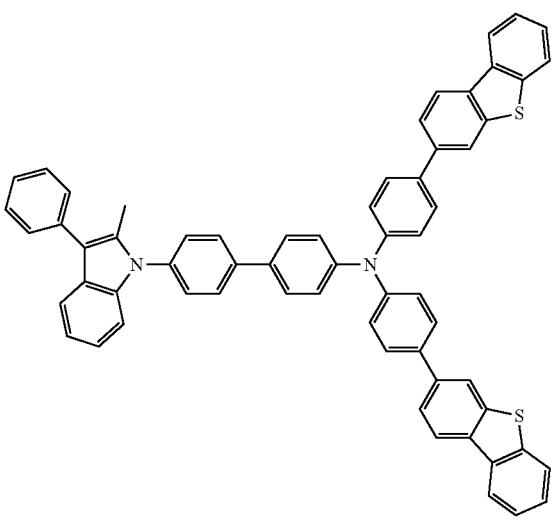
27
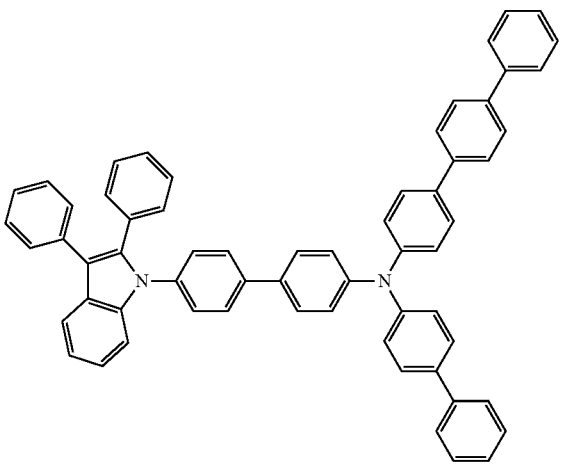
28

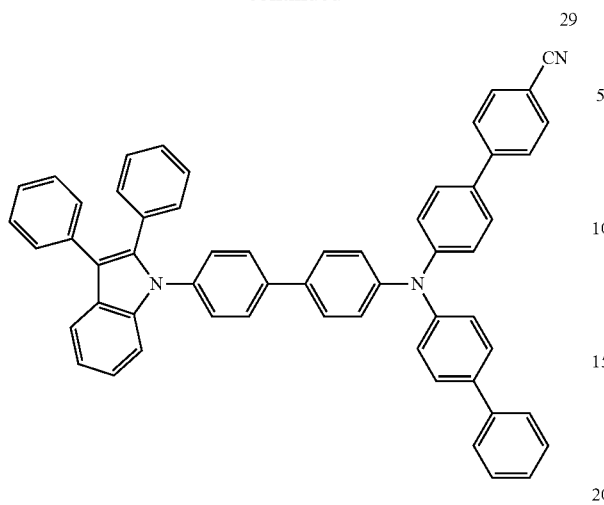
29
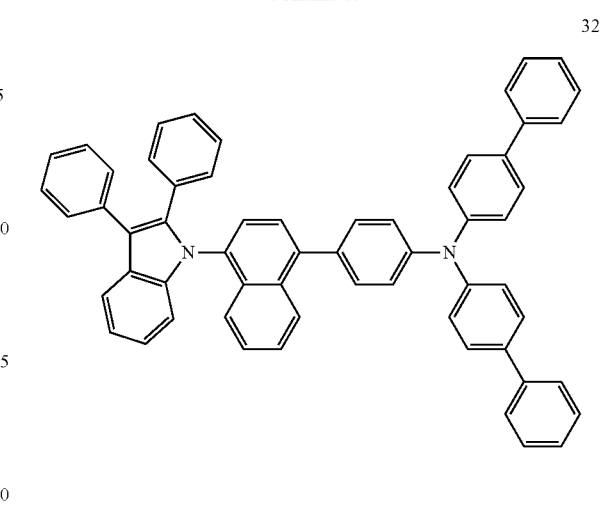
32
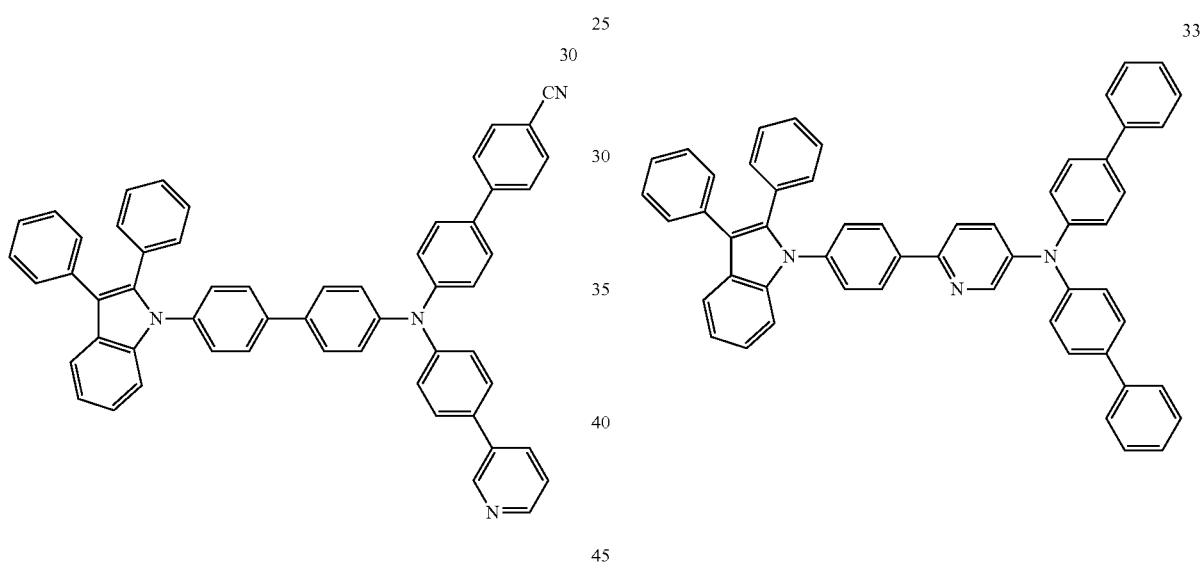
30
31
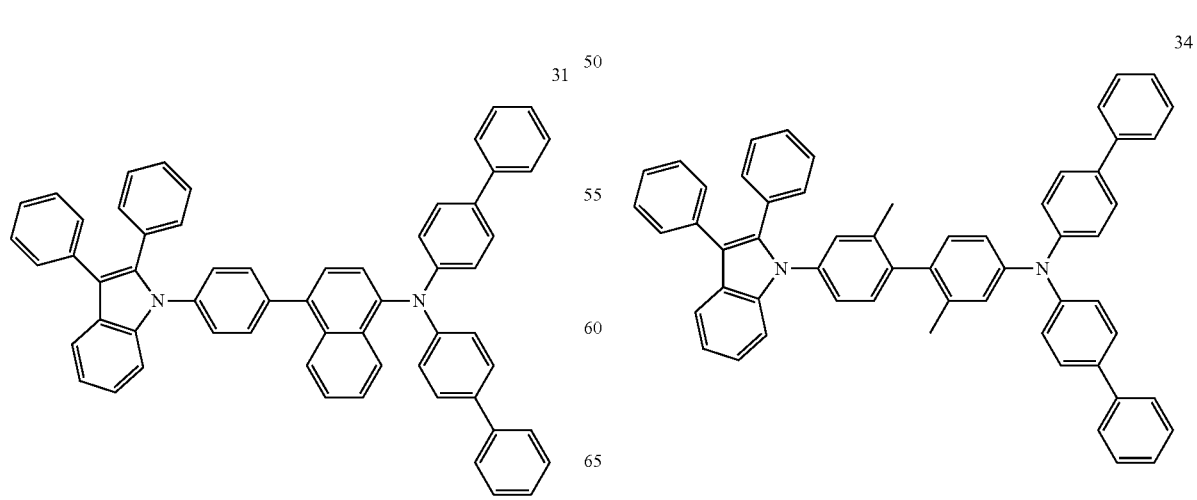
33
34

-continued
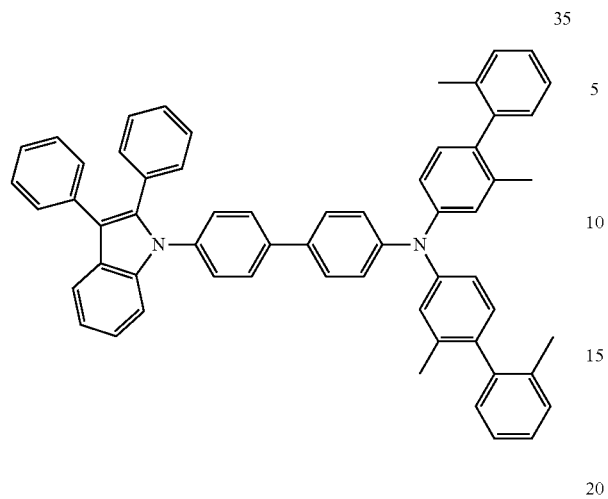
35
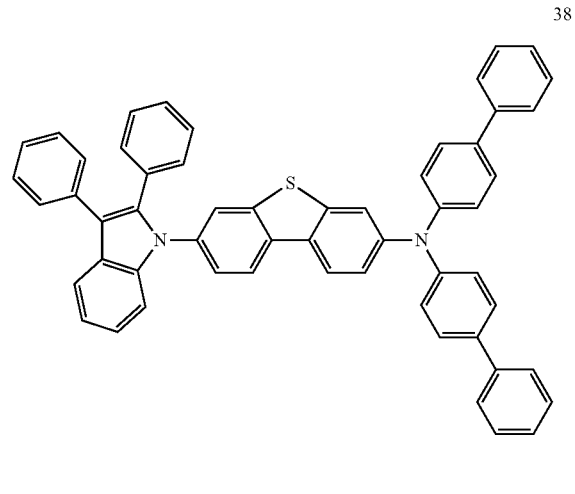
38
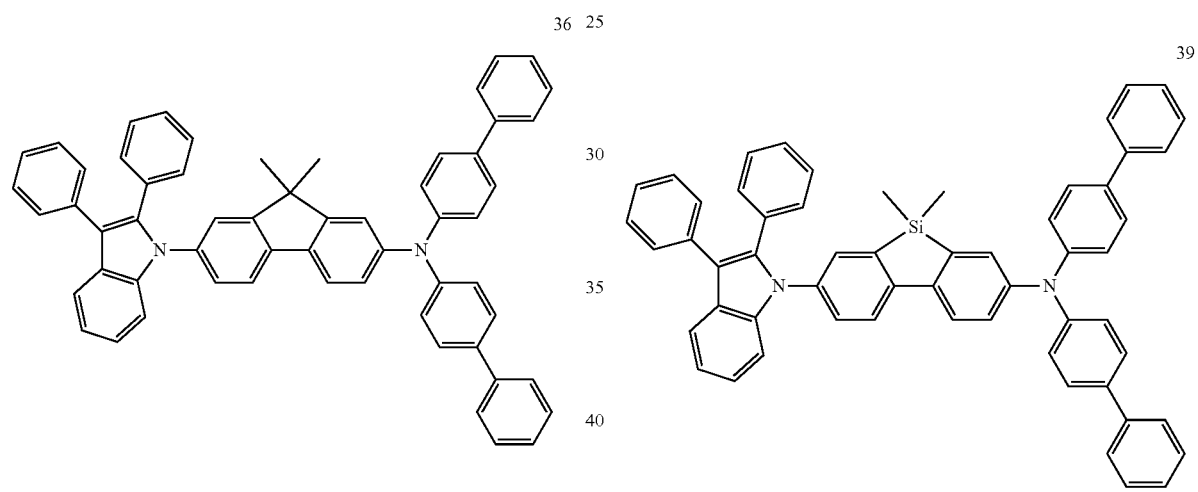
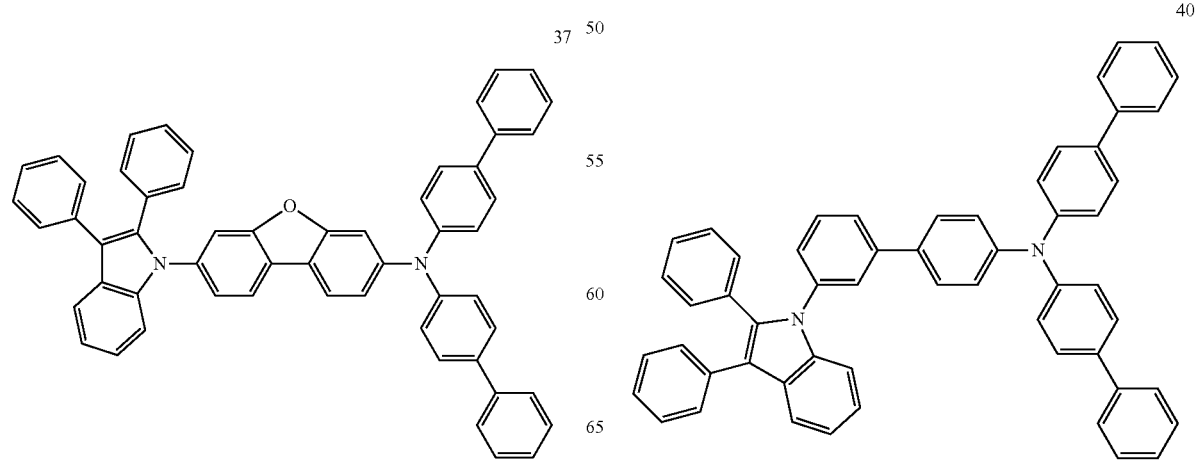

41
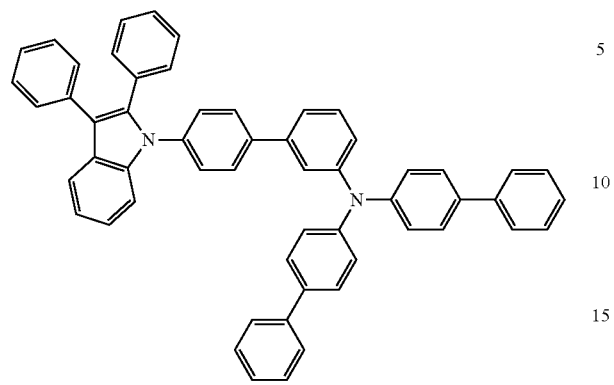
42
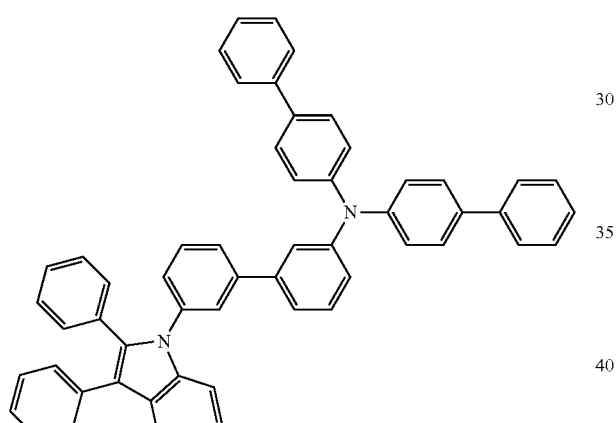
43
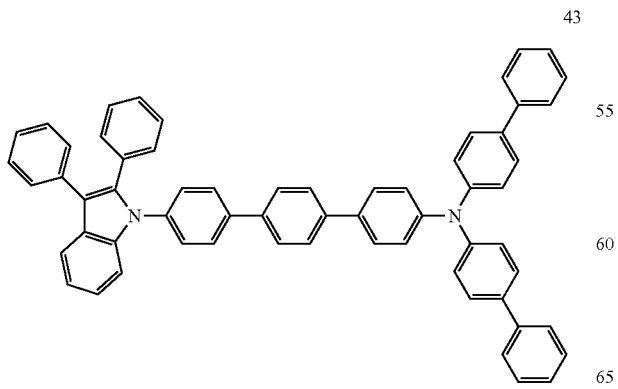
44
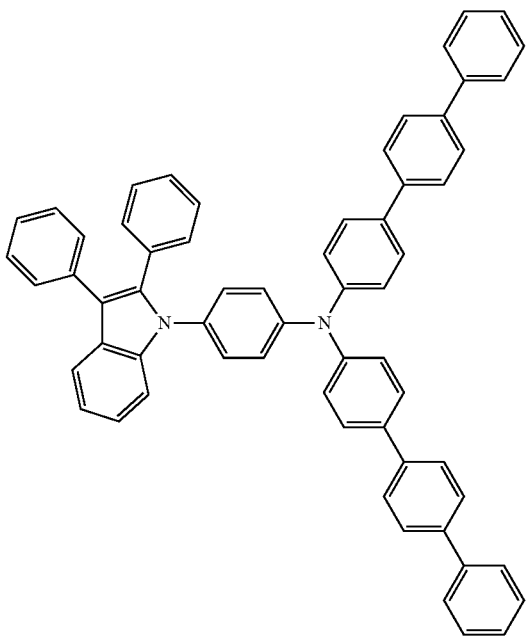
45
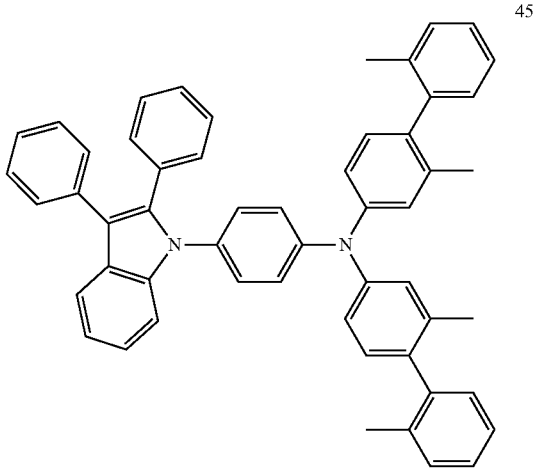
46
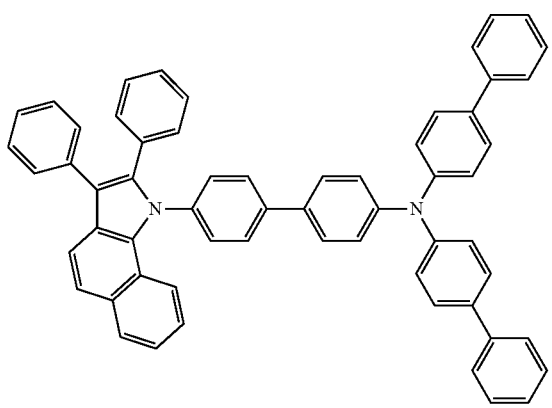

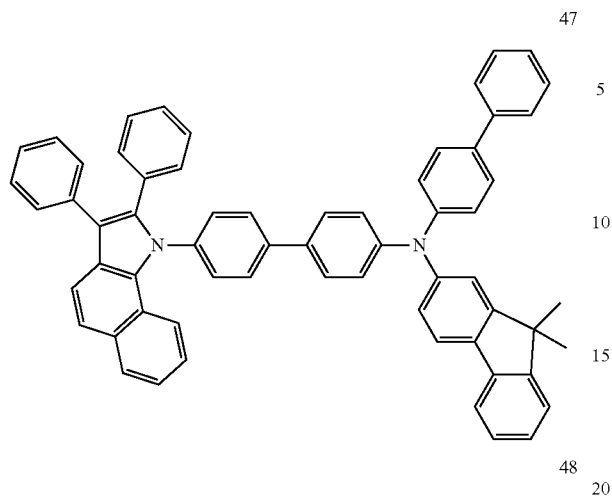
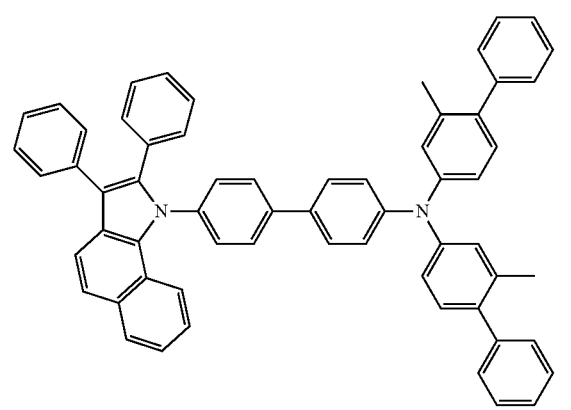
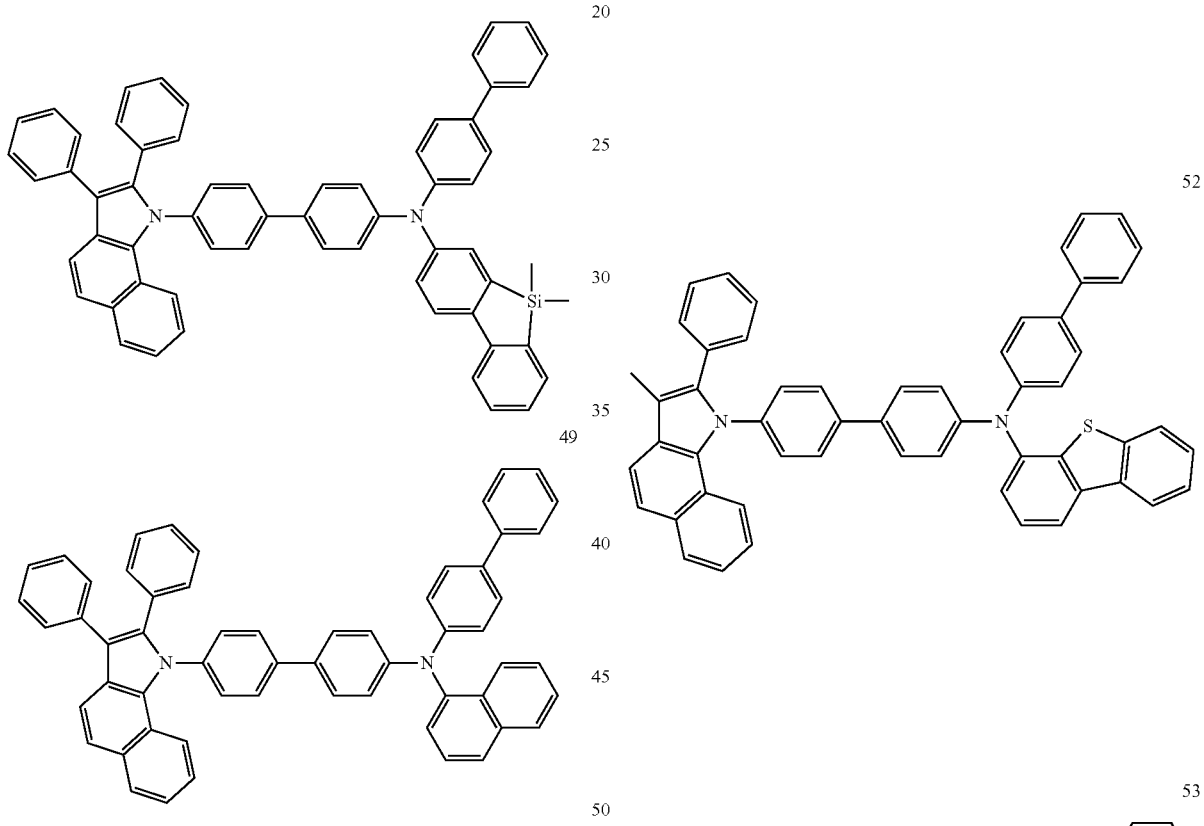
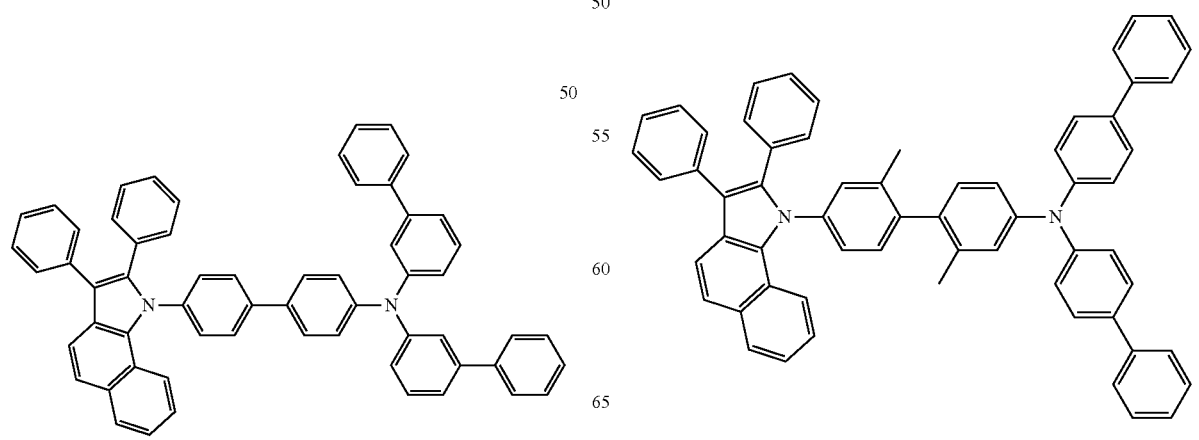

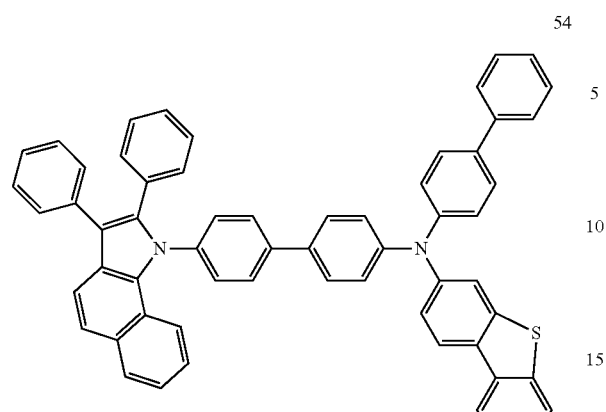
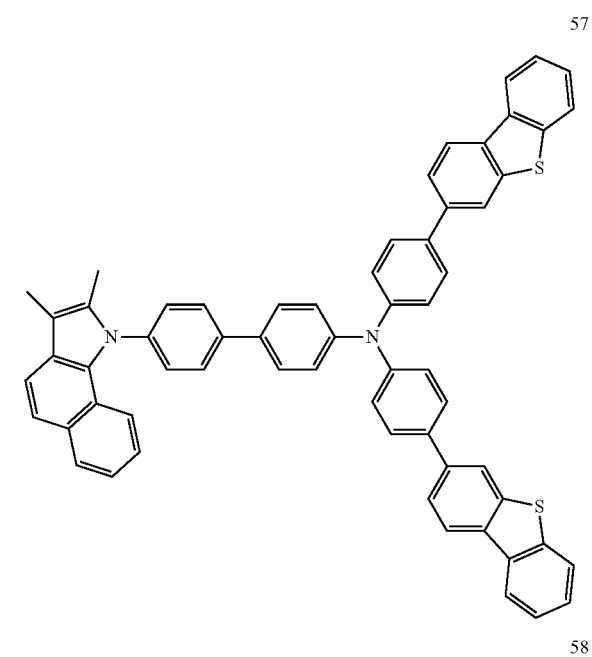
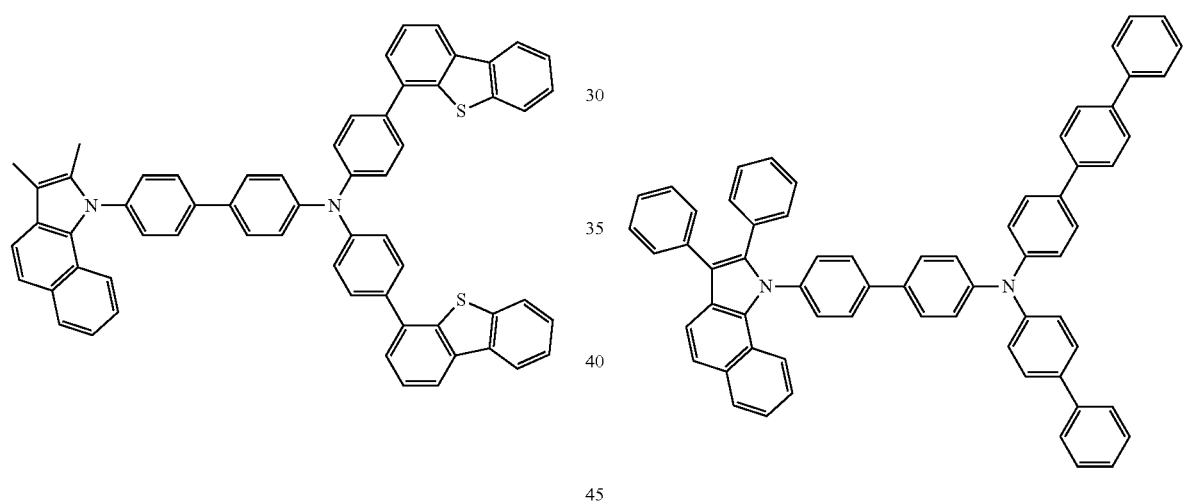
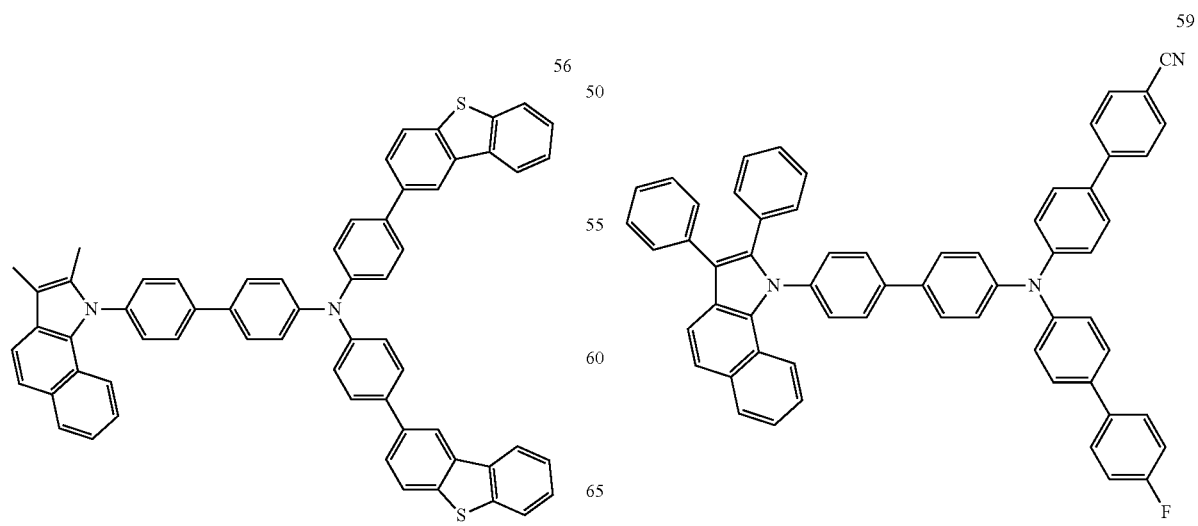

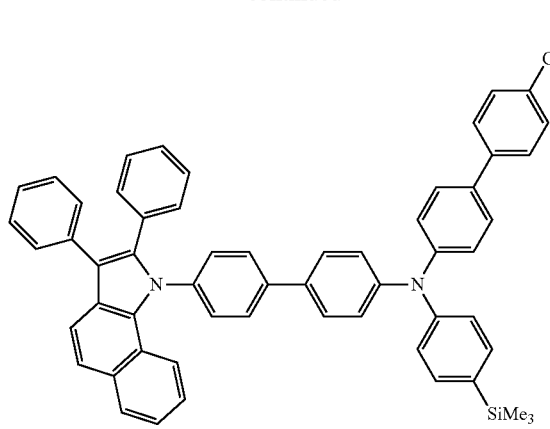
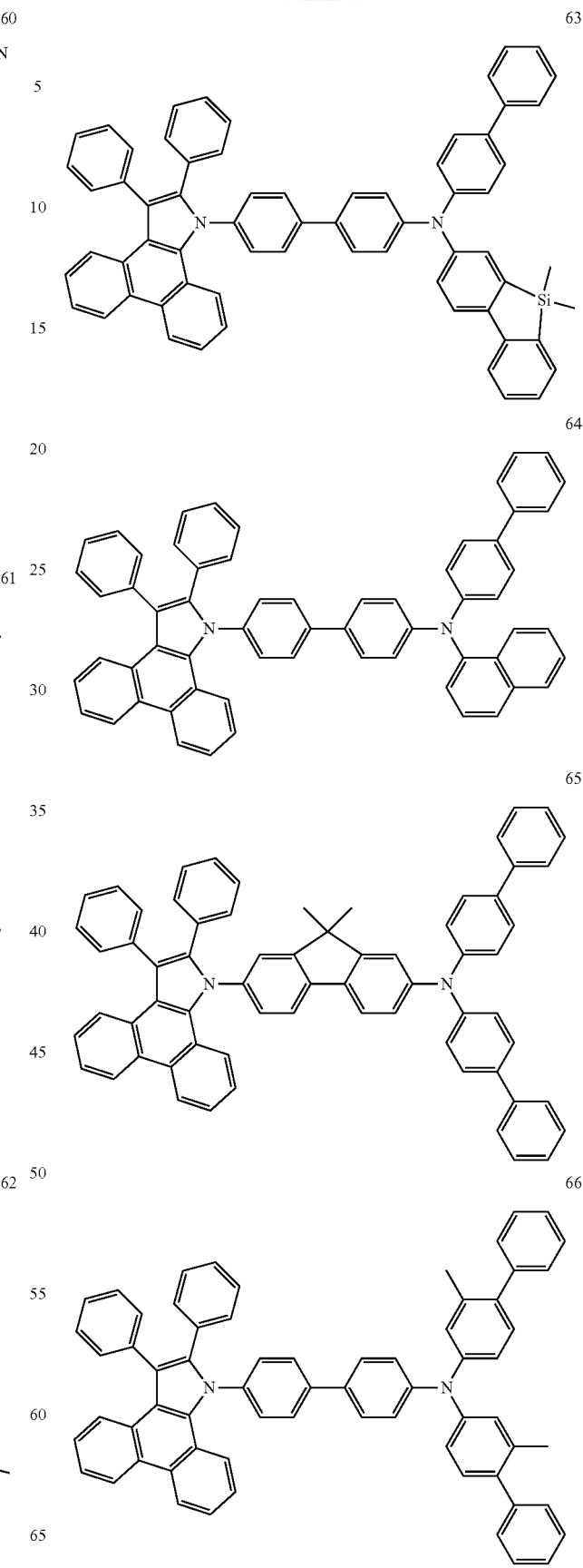

67
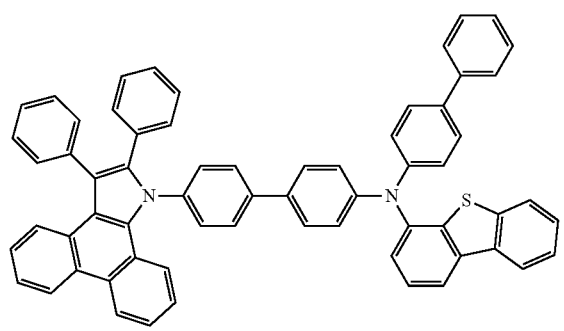
68
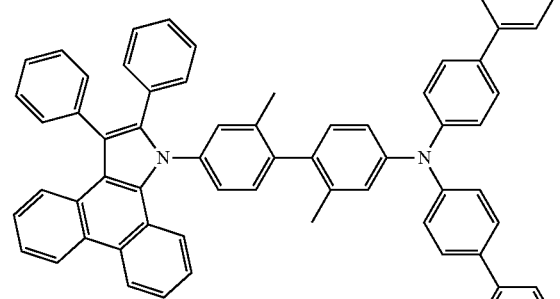
69
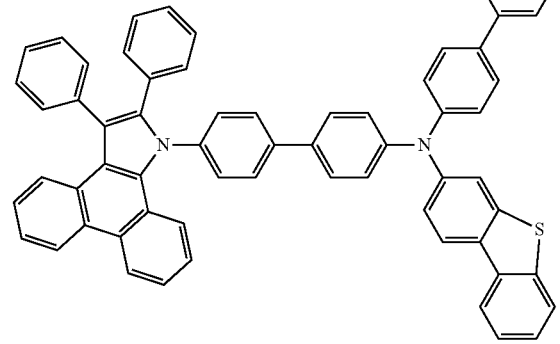
70
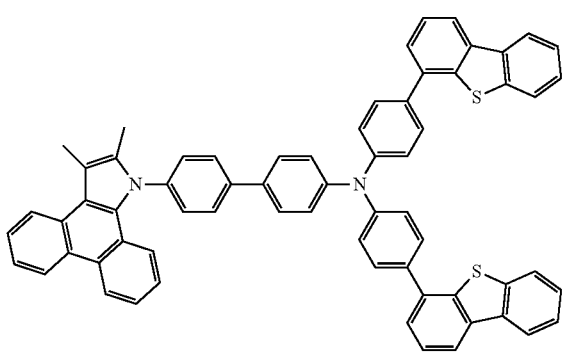
71
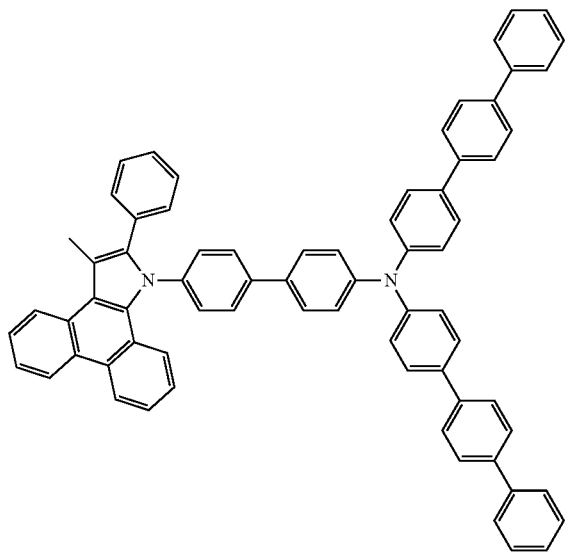
72
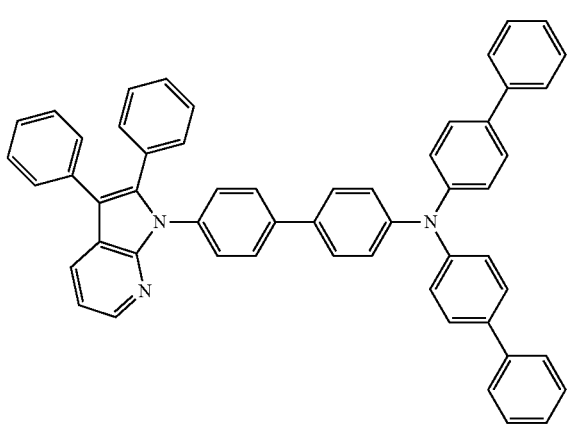
73
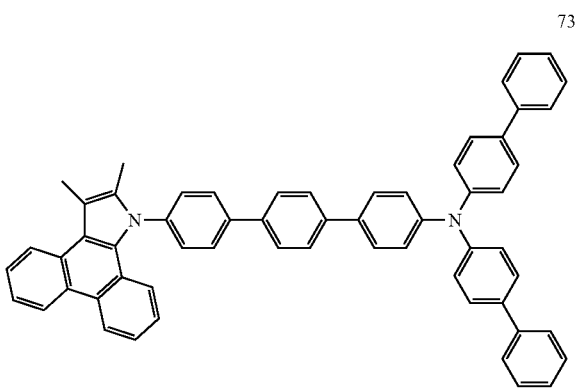

74
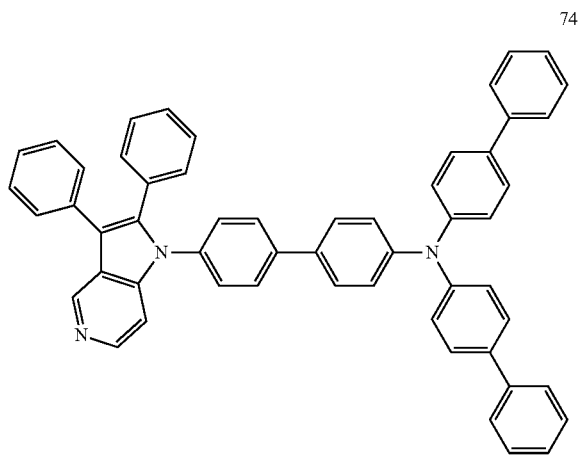
75
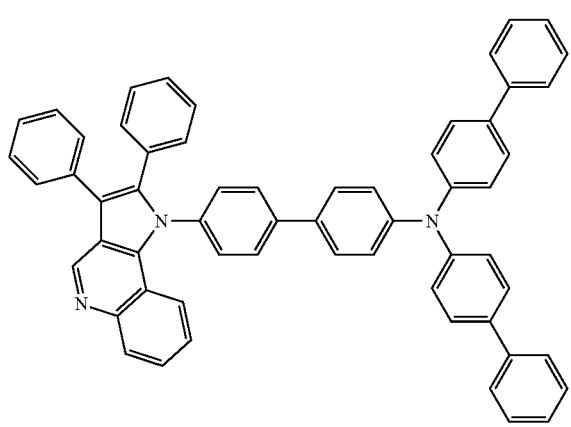
76
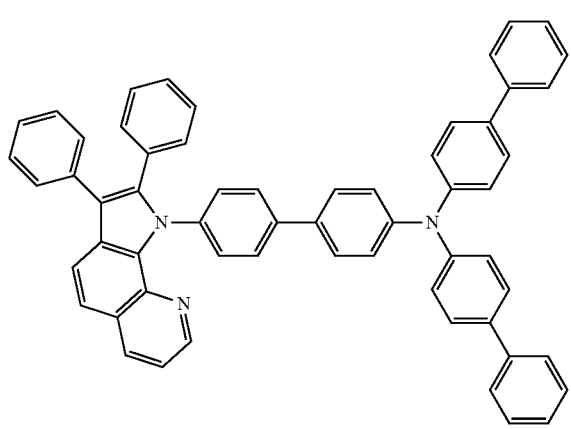
77
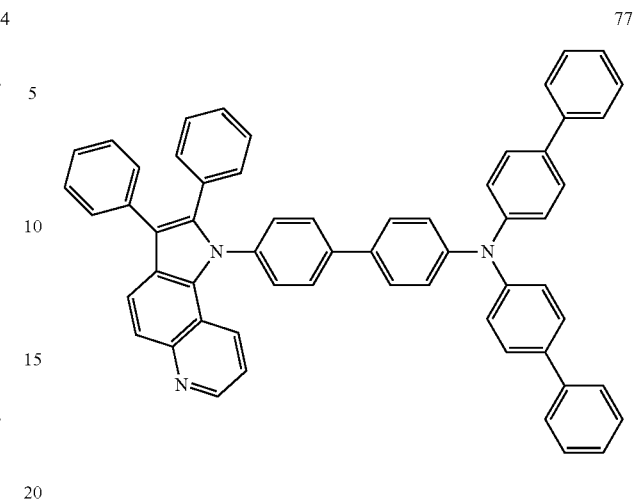
78
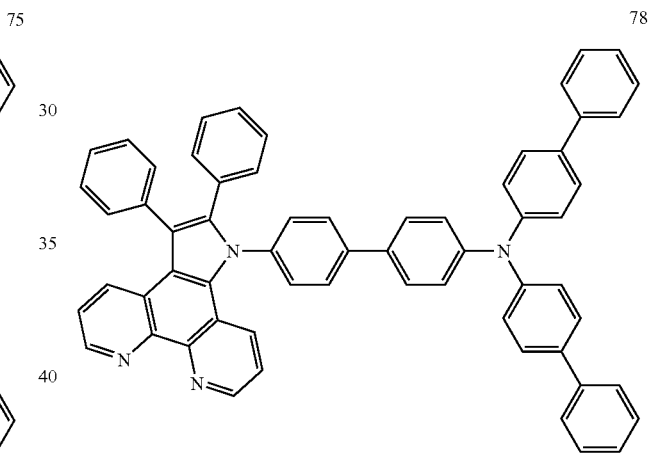
79
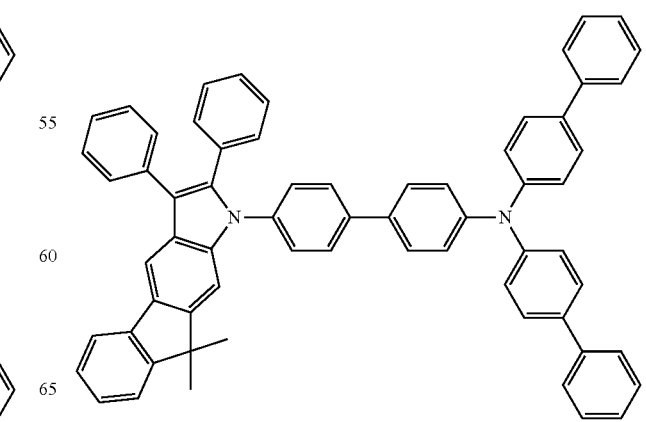

-continued

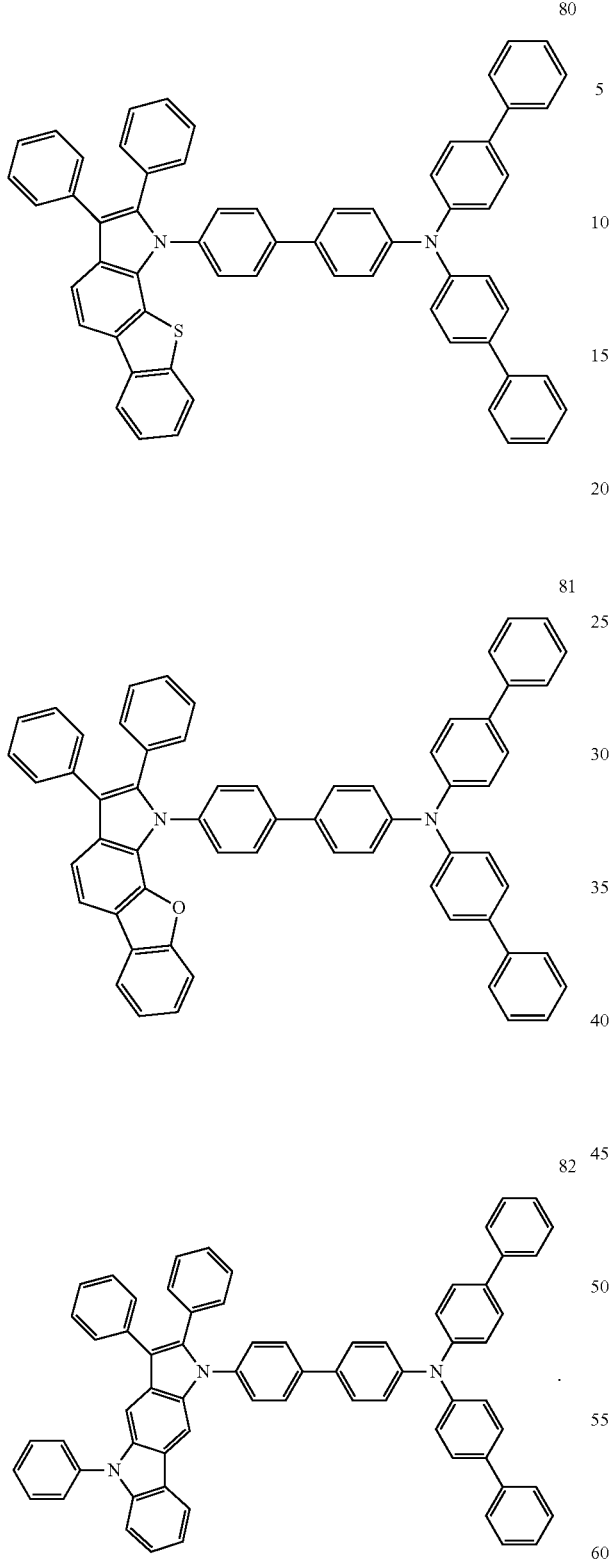

12. An organic light emitting diode comprising:
a first electrode;
a second electrode facing the first electrode; and
an organic layer between the first electrode and the second electrode, and comprising an emission layer,
wherein the organic layer comprises an arylamine-based compound represented by Formula 1 below, Formula 1

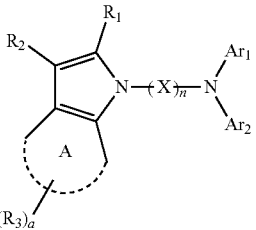

wherein in Formula 1,
ring A is selected from: a $C_6$-$C_{20}$ aromatic ring or a $C_2$-$C_{20}$ heteroaromatic ring;
each X is independently selected from: a substituted or unsubstituted $C_6$-$C_{30}$ arylene group, or a substituted or unsubstituted $C_2$-$C_{30}$ heteroarylene group, and two or more Xs are optionally connected to each other to form a substituted or unsubstituted saturated ring or a substituted or unsubstituted unsaturated ring;
n is an integer of 1 to 5;
each of $Ar_1$ and $Ar_2$ is independently selected from: a substituted or unsubstituted $C_6$-$C_{30}$ aryl group or a substituted or unsubstituted $C_2$-$C_{30}$ heteroaryl group;
each of $R_1$, $R_2$ and each of $R_3$ is independently selected from: a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or a substituted or unsubstituted $C_2$-$C_{30}$ heteroaryl group; and
a is an integer of 0 to 4,
wherein the organic layer comprises:
a hole transporting region between the first electrode and the emission layer, the hole transporting region further comprising at least one of: a hole injecting layer, a hole transporting layer, a functional layer having both hole injecting and hole transporting capabilities, a buffer layer, or an electron blocking layer, and
an electron transporting region between the emission layer and the second electrode, the electron transporting region further comprising at least one of: a hole blocking layer, an electron transporting layer, or an electron injecting layer,
wherein the hole transporting layer comprises a first hole transporting layer and a second hole transporting layer,
wherein the second hole transporting layer is between the first hole transporting layer and the emission layer, and
the second hole transporting layer comprises the arylamine-based compound of Formula 1.

13. The organic light emitting diode of claim 12, wherein the second hole transporting layer comprises a first arylamine-based compound of Formula 1 and the first hole transporting layer comprises a second arylamine-based compound of Formula 1, and the first arylamine-based compound of Formula 1 is the same as or different from the second arylamine-based compound of Formula 1.

14. An arylamine-based compound represented by Formula 1 below:

Formula 1

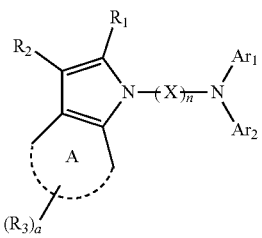

wherein in Formula 1, ring A is selected from: benzene, naphthalene, anthracene, fluorene, spiro-fluorene, phenanthrene, triphenylene, chrysene, naphthacene, perylene, pyrrole, imidazole, pyrazole, pyridine, pyrazine, pyrimidine, pyridazine, isoindole, indole, quinoline, isoquinoline, benzoquinoline, naphthyridine, quinoxaline, quinazoline, cinnoline, carbazole, phenanthridine, acridine, phenanthroline, phenazine, benzoxazole, benzimidazole, furan, benzofuran, thiophene, benzothiophene, thiazole, isothiazole, benzothiazole, isoxazole, oxazole, triazole, tetrazole, oxadiazole, triazine, dibenzofuran, dibenzothiophene, or benzocarbazole;

each X is independently selected from: a substituted or unsubstituted $C_6$-$C_{30}$ arylene group or a substituted or unsubstituted $C_2$-$C_{30}$ heteroarylene group, and two or more Xs are optionally connected to each other to form a substituted or unsubstituted saturated ring or a substituted or unsubstituted unsaturated ring;

n is an integer of 1 to 5;

each of $Ar_1$ and $Ar_2$ is independently any one of Formulae 4a to 4s:

<4a>
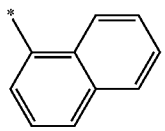

<4b>
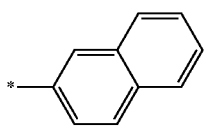

<4c>
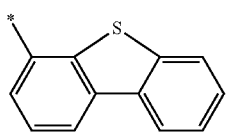

<4d>
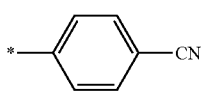

<4e>
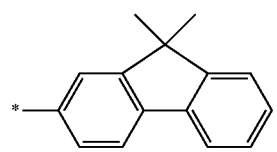

<4f>
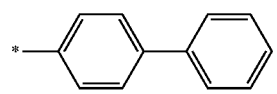

<4g>
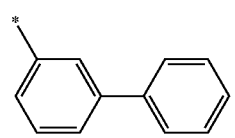

<4h>
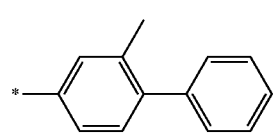

<4i>
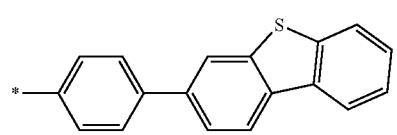

<4j>
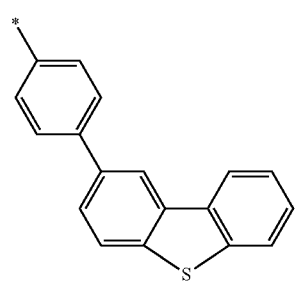

<4k>
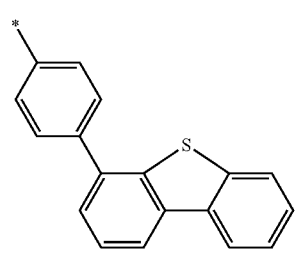

<4l>
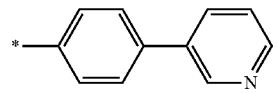

<4m>
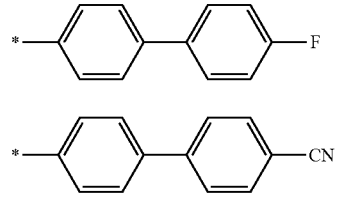

<4n>

-continued

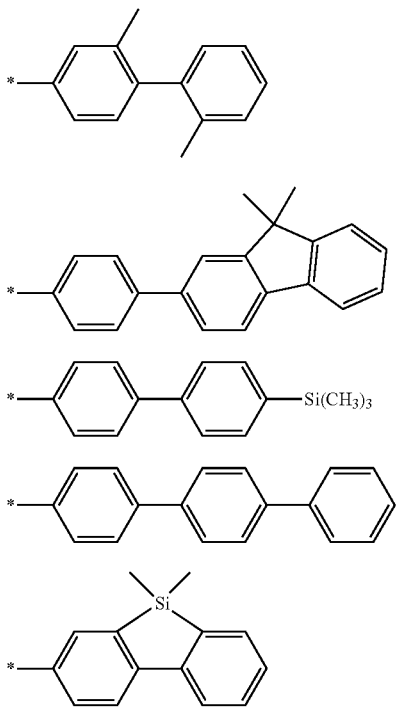

wherein in Formulae 4a to 4s,
is a binding site to the nitrogen atom;
each of $Ar_1$ and $Ar_2$ is independently selected from: a substituted or unsubstituted $C_6$-$C_{30}$ aryl group or a substituted or unsubstituted $C_2$-$C_{30}$ heteroaryl group;

each of $R_1$, and $R_2$ is independently selected from: a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or a substituted or unsubstituted $C_2$-$C_{30}$ heteroaryl group;

each of $R_3$ is independently a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, or an unsubstituted $C_2$-$C_{30}$ heteroaryl group; and
a is an integer of 0 to 4.

* * * * *